(12) United States Patent
Rubin et al.

(10) Patent No.: US 8,247,451 B2
(45) Date of Patent: Aug. 21, 2012

(54) ADAM10 AND ITS USES RELATED TO INFECTION

(75) Inventors: Donald H. Rubin, Nashville, TN (US); Thomas Hodge, Athens, GA (US); James Murray, Bogart, GA (US)

(73) Assignees: Vanderbilt University, Nashville, TN (US); University of Georgia Research Foundation, Athens, GA (US); The United States of America as represented by the Department of Veterans Affairs, Washington, DC (US)

( * ) Notice: Subject to any disclaimer, the term of this patent is extended or adjusted under 35 U.S.C. 154(b) by 385 days.

(21) Appl. No.: 12/160,862

(22) PCT Filed: Jan. 16, 2007

(86) PCT No.: PCT/US2007/001108
§ 371 (c)(1),
(2), (4) Date: Nov. 18, 2008

(87) PCT Pub. No.: WO2007/084488
PCT Pub. Date: Jul. 26, 2007

(65) Prior Publication Data
US 2009/0220514 A1    Sep. 3, 2009

Related U.S. Application Data

(60) Provisional application No. 60/847,072, filed on Sep. 25, 2006, provisional application No. 60/758,887, filed on Jan. 13, 2006, provisional application No. 60/832,019, filed on Jul. 20, 2006.

(51) Int. Cl.
*A61K 31/19* (2006.01)
*A61K 31/18* (2006.01)
*A61K 31/155* (2006.01)

(52) U.S. Cl. .......... 514/575; 514/601; 514/602; 514/634

(58) Field of Classification Search .................. 514/575, 514/601, 602, 634
See application file for complete search history.

(56) References Cited

U.S. PATENT DOCUMENTS

| | | | |
|---|---|---|---|
| 4,704,692 A | 11/1987 | Ladner | 340/711 |
| 6,172,064 B1 | 1/2001 | Andrews | 514/237.8 |
| 6,191,150 B1 | 2/2001 | Andrews | 514/352 |
| 6,228,648 B1 | 5/2001 | Condon | 435/455 |
| 6,329,400 B1 | 12/2001 | Andrews | 514/336 |
| 6,867,349 B2 | 3/2005 | Ekker | 800/21 |
| 2003/0211610 A1 | 11/2003 | Condon | 435/375 |
| 2004/0247602 A1 | 12/2004 | Friedan | 424/155.1 |
| 2005/0227973 A1 | 10/2005 | Brown | 514/227.5 |
| 2006/0199820 A1 | 9/2006 | Bannen | 514/235.5 |

OTHER PUBLICATIONS

Lemjabbar et al., Platelet-activating factor receptor and ADAM10 mediate responses to *Staphylococcus aureus* in epithelial cells, 2002, Nature Medicine, vol. 8, pp. 41-46.*
GenBank Accession No. NM_007399 (mRNA sequence).
GenBank Accession No. NP_031425 (protein).

(Continued)

*Primary Examiner* — Shengjun Wang
(74) *Attorney, Agent, or Firm* — Ballard Spahr LLP

(57) ABSTRACT

The present invention relates to a protein, ADAM10, ADAM10 nucleic acid sequences and ADAM10 proteins encoded by these sequences that are involved in infection by one or more pathogen such as a virus, a parasite, a bacteria or a fungus or are otherwise associated with the life cycle of a pathogen.

4 Claims, 4 Drawing Sheets

OTHER PUBLICATIONS

GenBank Accession No. Z48444 (mRNA sequence).
GenBank Accession No. XM_217197 (mRNA sequence).
GenBank Accession No. XP_217197 (protein).
GenBank Accession No. CAA88359 (protein).
GenBank Accession No. NM_204261 (mRNA sequence).
GenBank Accession No. NP_989592 (protein sequence).
Baggiolini M, Clark-Lewis I. "Interleukin-8, a chemotactic and inflammatory cytokine." FEBS Lett. 307(1):97-101 (Jul. 1992).
Clark-Lewis I, Dewald B, Loetscher M, Mosert B, Baggiolini M. "Structural requirements for Interleukin-8 function identified by design of analogs and CXC chemokine hybrids." *J.Biol.Chem.*, 269(33):16075-16081 (1994).
Tyra G. Wolfsberg, Paul Primakoff, Diana G. Myles and Judith White. "Adam, A Novel Family of Membrane Proteins Containing a Disintegrin and Mealloprotease Domain: Multipotential Functions in Cell-Cell and Cell-Matrix Interactions." *J. Cell Biol.*, 131(2):275-278 (Oct. 1995).

* cited by examiner

ADAM10 AND ITS USES RELATED TO INFECTION

CROSS-REFERENCE TO RELATED APPLICATIONS

This application claims the benefit of U.S. Provisional Application No. 60/847,072, filed Sep. 25, 2006, U.S. Provisional Application No. 60/832,019, filed Jul. 20, 2006 and U.S. Provisional Application No. 60/758,887, filed Jan. 13, 2006. The aforementioned applications are herein incorporated by this reference in their entirety.

FIELD OF THE INVENTION

The present invention relates to an ADAM10 protein, ADAM10 nucleic acid sequences and ADAM10 proteins encoded by these sequences that are involved in infection by one or more pathogen such as a virus, a parasite, a bacteria or a fungus, or are otherwise associated with the life cycle of a pathogen.

BACKGROUND

Infectious diseases affect the health of people and animals around the world, causing serious illness and death. Public health efforts have focused on behavioral modification and other public health efforts to reduce the incidences of infection, while treatment regimens for these diseases have focused on pharmaceuticals, such as antibiotics and anti-viral medications. However, educating people about modifying behavior can be difficult, and that approach alone rarely can significantly diminish the incidence of infection. Furthermore, modifying the behavior of domestic or wild animals would not result in diminished infections. Stopping the spread of infections in an animal population typically involves wholesale slaughter. Few vaccines are available or wholly effective, and they tend to be specific for particular conditions.

The rate of HIV (human immunodeficiency virus) infection is increasing. HIV and its associated acquired immune deficiency syndrome (AIDS) accounted for approximately 5% of all deaths in the United States in the year 2000, while over 313,000 persons were reported to be living with AIDS in that same year. Centers for Disease Control and Prevention, *HIV/AIDS Surveillance Supplemental Report*, 8(1):1-22 (2002). These increasing infection rates have occurred, even though the mode of HIV infection has been known for almost 20 years, and educational programs around the world have promoted behavioral modifications meant to reduce HIV infection. Incidence and death rates due to HIV disease have been decreasing since the mid-90's, in part due to aggressive antiviral therapies, which frequently have toxic side effects and strict dosage schedules. However, even with treatment, the patient is not cured of the disease, and to date, no effective vaccine therapy has been found.

In other diseases, such as infection by the Ebola virus, not only are treatments limited, but containment or prevention of infections is difficult because the life cycle of the virus is not well known. The natural reservoir for the Ebola virus, that is the place or population in nature where the virus resides between human outbreaks, has not yet been identified.

Additionally, different viral strains can rapidly evolve in response to drug usage, producing drug-resistant strains. For example, strains of the influenza virus resistant to amantadine and rimantadine have arisen. There have also been reports of avian influenza strains that are resistant to tamiflu. In another example, a recent study of 80 newly-infected people conducted by the AIDS Research Center at Rockefeller University in New York, found that as many as 16.3% of these individuals had strains of HIV associated with resistance to some treatments, and 3.8% appeared to be resistant to several currently available anti-HIV drugs. Thus, a need exists for alternative treatments for infectious disease and methods of identifying new drugs to combat infectious disease.

SUMMARY OF THE INVENTION

The present invention provides ADAM10 nucleic acid sequences and proteins encoded by these sequences that are involved in infection by one or more pathogens such as a virus, a parasite, a bacteria or a fungus, or are otherwise associated with the life cycle of a pathogen. Also provided are methods of decreasing infection in a cell by a pathogen comprising decreasing expression or activity of ADAM10. Further provided are methods of identifying an agent that decreases infection by a pathogen. Also provided are methods of decreasing infection by a pathogen in a subject by administering an agent that decreases the expression and/or activity of ADAM10.

DETAILED DESCRIPTION OF THE INVENTION

Figure 1:
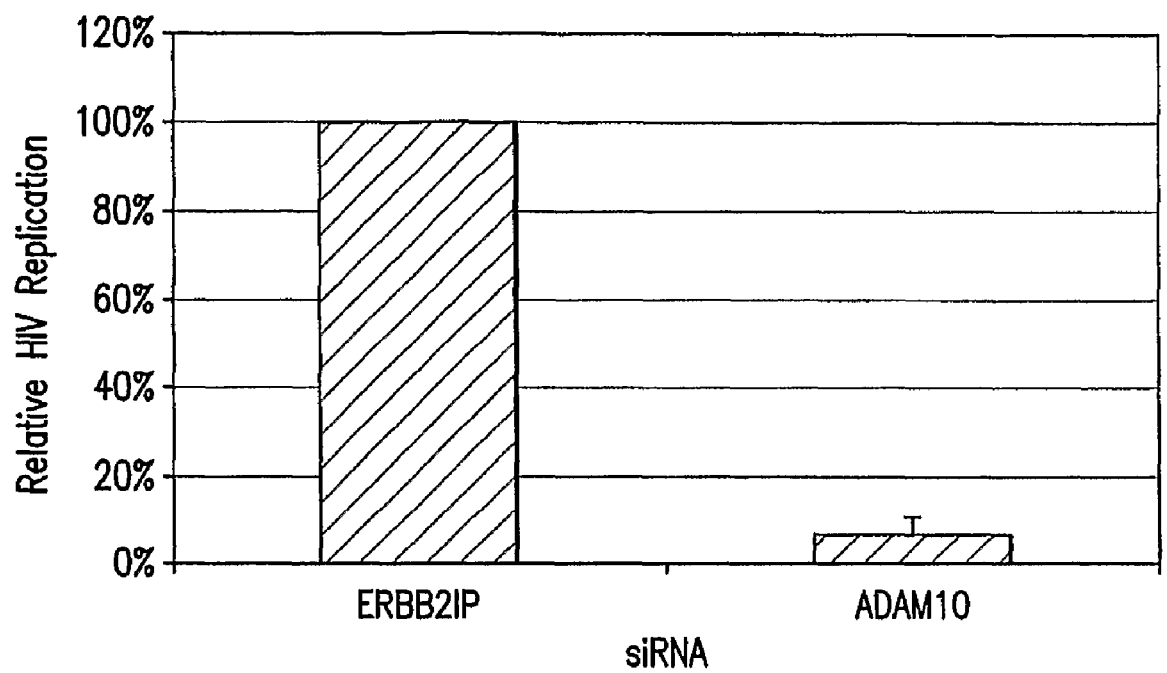
FIG. 1 shows inhibition of HIV replication with siRNA targeting the metalloproteinase ADAM10.

The present invention may be understood more readily by reference to the following detailed description of preferred embodiments of the invention and the Examples included therein.

Before the present compounds, compositions, articles, devices, and/or methods are disclosed and described, it is to be understood that this invention is not limited to specific nucleic acids, specific polypeptides, or to particular methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used throughout, by "subject" is meant an individual. Preferably, the subject is a mammal such as a primate, and, more preferably, a human. The term "subject" includes domesticated animals, such as cats, dogs, etc., livestock (for example, cattle, horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). The subjects of the present invention can also include, but are not limited to fish, amphibians and reptiles.

ADAM metallopeptidase 10 (ADAM10), a host nucleic acid sequence involved in viral infection, was identified using gene trap methods that were designed to identify host nucleic acid sequences that are necessary for viral infection, but not necessary for the survival of the cell. These gene trap methods are set forth in U.S. Pat. Nos. 6,448,000 and 6,777,177. U.S. Pat. Nos. 6,448,000 and 6,777,177 are both incorporated herein in their entireties by this reference.

By "involved in viral infection" is meant that ADAM10 nucleic acids and their encoded proteins can be involved in all phases of viral life cycles including, but not limited to, viral attachment to cellular receptors, viral infection, viral entry, internalization, disassembly of the virus, viral replication, genomic integration of viral sequences, translation of mRNA, proteolytic cleavage of viral proteins or cellular proteins, assembly of viral particles, cell lysis and egress of virus from the cells. Although ADAM10 was identified as a cellular protein involved in viral infection, as discussed throughout, the present invention is not limited to viral infection. Therefore, ADAM10 can be involved in infection by any infectious pathogen such as a bacteria, a fungus or a parasite which includes involvement in any phase of the infectious pathogen's life cycle.

ADAM10 is a cell surface zinc metalloprotease that enzymatically cleaves many proteins including TNF-alpha and E-cadherin. ADAM10 can also be localized internally in the trans golgi network as well as in other subcellular domains. Human ADAM10, located on chromosome 15 (15q2: 15q22) was identified and characterized by Rosendahl et al. (see "Identification and Characterization of a Pro-Tumor Necrosis Factor-α-processing Enzyme from the ADAM Family of Zinc Metalloproteases" *Journal of Biological Chemistry* 272 (39): 24588-24593 (1997) which is hereby incorporated in its entirety by this reference). In addition to its role in enzymatic cleavage of proteins, the present invention shows that ADAM10 is a host protein involved in infection by pathogens (including, but not limited to, viruses, bacteria, fungi and parasites) that use similar pathways for morphogenesis of infectious particles.

As utilized herein, ADAM10 includes any ADAM10 gene, nucleic acid (DNA or RNA) or protein from any organism that retains at least one ADAM10 activity and can function as an ADAM10 nucleic acid or protein. For example, the ADAM10 sequence can be from a human, a mouse, a rat, a cat, a dog, a chimpanzee, a horse, a cow, a pig, a sheep, a guinea pig, a rabbit, a zebrafish, a chicken, to name a few.

Examples of native human ADAM10 sequences include, but are not limited to GenBank Accession Nos. NM_001110 (mRNA sequence) (SEQ ID NO: 77), AF009615 (mRNA sequence) (SEQ ID NO: 78), AAC51766 (protein) (SEQ ID NO: 79) and NP001101 (protein) SEQ ID NO: 80). Examples of native mouse ADAM10 sequences include, but are not limited to GenBank Accession Nos. NM_007399 (mRNA sequence), NP_031425 (protein). Examples of native rat ADAM10 sequences include, but are not limited to GenBank Accession Nos. Z48444 (mRNA sequence), XM_217197 (mRNA sequence), XP_217197 (protein), CAA88359 (protein). Examples of chicken ADAM10 sequences include, but are not limited to NM_204261 (mRNA sequence), NP_989592 (protein sequence). These examples are not meant to be limiting as one of skill in the art would know how to obtain additional ADAM10 sequences from other species by accessing GenBank or other sequence databases. One of skill in the art would also know now to align the sequences disclosed herein with sequences from other species in order to determine similarities and differences between ADAM10 sequences. The nucleic acid sequences and protein sequences provided under the GenBank Accession Nos. mentioned herein are hereby incorporated in their entireties by this reference. An ADAM10 sequence can be a full-length wild-type (or native) sequence, a genomic ADAM10 sequence, an ADAM10 variant (for example, an allelic variant), an ADAM10 fragment, homologs or fusion sequences that retain ADAM10 activity. ADAM10 activity includes, but is not limited to, ADAM10 enzymatic activity, for example, the ability to cleave TNF-alpha, E-cadherin and other peptides (see Rosendahl et al. for peptide cleave assay) as well as the ability to function as a cellular nucleic acid or protein involved in infection.

In certain examples, ADAM10 has at least 70% sequence identity, for example at least 75%, 80%, 85%, 90%, 95%, or 98% sequence identity to a native ADAM10 sequence. In other examples, ADAM10 has a sequence that hybridizes to a sequence set forth under GenBank Accession No. NM_001110 or hybridizes to the sequence set forth in under GenBank Accession No. AF009615 and retains ADAM10 activity.

Additional information for human ADAM10 can be found under Entrez Gene ID: 102. All of the information set forth under Entrez Gene ID:102 or accessible via Entrez Gene ID: 102 is hereby incorporated entirely by this reference. One of skill in the art can readily obtain this information from the National Center for Biotechnology Information at the National Library of Medicine (http://www.ncbi.nlm.nih-.gov/entrez/query.fcgi?db=gene).

Nucleic Acids

As used herein, the term "nucleic acid" refers to single or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system. The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in Sambrook et al. (2001) *Molecular Cloning-A Laboratory Manual* (3rd ed.) Vol. 1-3, Cold Spring Harbor Laboratory, Cold Spring Harbor Press, NY, (Sambrook).

Once the nucleic acid sequence is obtained, the sequence encoding the specific amino acids can be modified or changed at any particular amino acid position by techniques well known in the art. For example, PCR primers can be designed which span the amino acid position or positions and which can substitute any amino acid for another amino acid. Alternatively, one skilled in the art can introduce specific mutations at any point in a particular nucleic acid sequence through techniques for point mutagenesis. General methods are set forth in Smith, M. "In vitro mutagenesis" *Ann. Rev. Gen.*, 19:423-462 (1985) and Zoller, M. J. "New molecular biology methods for protein engineering" *Curr. Opin. Struct. Biol.*, 1:605-610 (1991), which are incorporated herein in their entirety for the methods. These techniques can be used to alter the coding sequence without altering the amino acid sequence that is encoded.

As stated above, the sequences contemplated herein include full-length wild-type (or native) sequences, as well as allelic variants, variants, fragments, homologs or fusion sequences that retain the ability to function as ADAM10. In certain examples, a protein or nucleic acid sequence has at least 70% sequence identity, for example at least 75%, 80%, 85%, 90%, 95%, or 98% sequence identity to a native ADAM10 sequence. In other examples, a nucleic acid sequence involved in infection has a sequence that hybridizes to ADAM10 sequences set forth herein and retains ADAM10 activity.

Unless otherwise specified, any reference to a nucleic acid molecule includes the reverse complement of the nucleic acid. Except where single-strandedness is required by the text herein (for example, a ssRNA molecule), any nucleic acid written to depict only a single strand encompasses both strands of a corresponding double-stranded nucleic acid. For example, depiction of a plus-strand of a dsDNA also encompasses the complementary minus-strand of that dsDNA. Additionally, reference to the nucleic acid molecule that encodes a specific protein, or a fragment thereof, encompasses both the sense strand and its reverse complement. Fragments of ADAM10 nucleic acids are also contemplated. These fragments can be utilized as primers and probes to amplify or detect ADAM10.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each High Stringency (Detects Sequences that Share 80% Identity or Greater)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each Low Stringency (Detects Sequences that Share Greater than 50% Identity)
Hybridization: 6×SSC at RT to 55° C. for 16-20 hours
Wash at least twice: 2×-3×SSC at RT to 55° C. for 20-30 minutes each.

Also provided is a vector, comprising an ADAM10 nucleic acid of the present invention. The vector can direct the in vivo or in vitro synthesis of any of the ADAM10 proteins or ADAM10 polypeptides described herein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.). The vector, for example, can be a plasmid. The vectors can contain genes conferring hygromycin resistance, ampicillin resistance, gentamicin resistance, neomycin resistance or other genes or phenotypes suitable for use as selectable markers, or methotrexate resistance for gene amplification.

There are numerous other *E. coli* (*Escherichia coli*) expression vectors, known to one of ordinary skill in the art, which are useful for the expression of the nucleic acid insert. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures. Also, nucleic acid modifications can be made to promote amino terminal homogeneity.

Additionally, yeast expression can be used. The invention provides a nucleic acid encoding a polypeptide of the present invention, wherein the nucleic acid can be expressed by a yeast cell. More specifically, the nucleic acid can be expressed by *Pichia pastoris* or *S. cerevisiae*. There are several advantages to yeast expression systems, which include, for example, *Saccharomyces cerevisiae* and *Pichia pastoris*. First, evidence exists that proteins produced in a yeast secretion systems exhibit correct disulfide pairing. Second, efficient large scale production can be carried out using yeast expression systems. The *Saccharomyces cerevisiae* pre-pro-alpha mating factor leader region (encoded by the MFα-1 gene) can be used to direct protein secretion from yeast (Brake, et al.). The leader region of pre-pro-alpha mating factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha mating factor leader region. This construct can be put under the control of a strong transcription promoter, such as the alcohol dehydrogenase I promoter, alcohol oxidase I promoter, a glycolytic promoter, or a promoter for the galactose utilization pathway. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, genticin or G418 resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc.

The expression vectors described herein can also include nucleic acids of the present invention under the control of an inducible promoter such as the tetracycline inducible promoter or a glucocorticoid inducible promoter. The nucleic acids of the present invention can also be under the control of a tissue-specific promoter to promote expression of the nucleic acid in specific cells, tissues or organs. Any regulatable promoter, such as a metallothionein promoter, a heat-shock promoter, and other regulatable promoters, of which many examples are well known in the art are also contemplated. Furthermore, a Cre-loxP inducible system can also be used, as well as a Flp recombinase inducible promoter system, both of which are known in the art.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexin1, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice.

The invention also provides for the vectors containing the contemplated nucleic acids in a host suitable for expressing the nucleic acids. The host cell can be a prokaryotic cell, including, for example, a bacterial cell. More particularly, the bacterial cell can be an *E. coli* cell. Alternatively, the cell can be a eukaryotic cell, including, for example, a Chinese hamster ovary (CHO) cell, a COS-7 cell, a HELA cell, an avian cell, a myeloma cell, a *Pichia* cell, or an insect cell. The coding sequence for any of the polypeptides described herein can be introduced into a Chinese hamster ovary (CHO) cell line, for example, using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines have been developed and include myeloma cell lines, fibroblast cell lines, a cell line suitable for infection by a pathogen, and a variety of tumor cell lines such as melanoma cell lines. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, Lipofectamine, or lipofectin mediated transfection, electroporation or any method now known or identified in the future can be used for other eukaryotic cellular hosts.

Polypeptides

The present invention provides isolated polypeptides comprising the polypeptide or protein sequences set forth under the GenBank Accession Nos. set forth above. The present invention also provides fragments of these polypeptides. These fragments can be of sufficient length to serve as antigenic peptides for the generation of antibodies. The present invention also contemplates functional fragments of ADAM10 that possess at least one activity of ADAM10, for example, necessary for viral infection, but not necessary for survival of the cell. It will be known to one of skill in the art that the ADAM10 polypeptides set herein possess other properties, such as metalloprotease activity (i.e. enzymatic cleavage of proteins, for example, TNF-alpha and E-cadherin). Fragments and variants of ADAM10 polypeptides can include one or more conservative amino acid residues as compared to the amino acid sequence listed under their respective GenBank Accession Nos.

By "isolated polypeptide" or "purified polypeptide" is meant a polypeptide that is substantially free from the materials with which the polypeptide is normally associated in nature or in culture. The polypeptides of the invention can be obtained, for example, by extraction from a natural source if available (for example, a mammalian cell), by expression of a recombinant nucleic acid encoding the polypeptide (for example, in a cell or in a cell-free translation system), or by chemically synthesizing the polypeptide. In addition, a polypeptide can be obtained by cleaving full length polypeptides. When the polypeptide is a fragment of a larger naturally occurring polypeptide, the isolated polypeptide is shorter than and excludes the full-length, naturally-occurring polypeptide of which it is a fragment.

The polypeptides of the invention can be prepared using any of a number of chemical polypeptide synthesis techniques well known to those of ordinary skill in the art including solution methods and solid phase methods. One method of producing the polypeptides of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin, whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The polypeptides of the invention can also be prepared by other means including, for example, recombinant techniques. Examples of appropriate cloning and sequencing techniques, and instructions sufficient to direct persons of skill through many cloning exercises are found in Sambrook et al. (2001) *Molecular Cloning-A Laboratory Manual* (3rd ed.) Vol. 1-3, Cold Spring Harbor Laboratory, Cold Spring Harbor Press, NY, (Sambrook).

Also provided by the present invention is a polypeptide comprising an amino acid sequence at least about 70%, 75%, 80%, 85%, 90%, 95%, 96%, 97%, 98% or 99% identical to the polypeptide sequences set forth under the GenBank Accession Nos. disclosed herein.

It is understood that as discussed herein the use of the terms "homology" and "identity" mean the same thing as similarity. Thus, for example, if the use of the word homology is used to refer to two non-natural sequences, it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of homology to specific known sequences. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.mov/blast/b12seg/b12.html)), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Also provided by the present invention are polypeptides set forth under the GenBank Accession Nos. disclosed herein, with one or more conservative amino acid substitutions. These conservative substitutions are such that a naturally occurring amino acid is replaced by one having similar properties. Such conservative substitutions do not alter the function of the polypeptide. For example, conservative substitutions can be made according to the following table:

TABLE 1

Amino Acid Substitutions

| Original Residue | Exemplary Substitutions |
| --- | --- |
| Arg | Lys |
| Asn | Gln |
| Asp | Glu |
| Cys | Ser |
| Gln | Asn |

TABLE 1-continued

Amino Acid Substitutions

| Original Residue | Exemplary Substitutions |
| --- | --- |
| Glu | Asp |
| Gly | Pro |
| His | Gln |
| Ile | leu; val |
| Leu | ile; val |
| Lys | arg; gln |
| Met | leu; ile |
| Phe | met; leu; tyr |
| Ser | Thr |
| Thr | Ser |
| Trp | Tyr |
| Tyr | trp; phe |
| Val | ile; leu |

Thus, it is understood that, where desired, modifications and changes may be made in the nucleic acid encoding the polypeptides of this invention and/or amino acid sequence of the polypeptides of the present invention and still obtain a polypeptide having like or otherwise desirable characteristics. Such changes may occur in natural isolates or may be synthetically introduced using site-specific mutagenesis, the procedures for which, such as mis-match polymerase chain reaction (PCR), are well known in the art. For example, certain amino acids may be substituted for other amino acids in a polypeptide without appreciable loss of functional activity. It is thus contemplated that various changes may be made in the amino acid sequence of the polypeptides of the present invention (or underlying nucleic acid sequence) without appreciable loss of biological utility or activity and possibly with an increase in such utility or activity. Thus, it is clear that naturally occurring variations in the polypeptide sequences set forth herein as well as genetically engineered variations in the polypeptide sequences set forth herein are contemplated by the present invention. By providing the genomic location of genes that are involved in viral infection, the present invention has also provided the genomic location of any variant sequences of these genes. Thus, based on the information provided herein, it would be routine for one of skill in the art to identify and sequence the genomic region identified by applicants and identify variant sequences of the genes set forth herein. It would also be routine for one of skill in the art to utilize comparison tools and bioinformatics techniques to identify sequences from other species that are homologs of the genes set forth herein and are also necessary for infection, but not necessary for survival of the cell.

Antibodies

The present invention also provides antibodies that specifically bind to ADAM10 gene products, polypeptides, proteins and fragments thereof. Further provided is an antibody that specifically binds to a ADAM10 gene product, polypeptide, protein or fragment thereof and modulates that activity of ADAM10. As utilized herein, by "modulate" or "modulation" is meant increasing or decreasing ADAM10 activity. For example, the present invention provides an anti-ADAM10 antibody that binds ADAM10, decreases ADAM10 activity and/or decreases infection in a cell by a pathogen. The ADAM10 antibody of the present invention can be a polyclonal antibody or a monoclonal antibody. The antibody of the invention selectively binds a polypeptide. By "selectively binds" or "specifically binds" is meant an antibody binding reaction which is determinative of the presence of the antigen (in the present case, a ADAM10 polypeptide or antigenic fragment thereof among a heterogeneous population of proteins and other biologics). Thus, under designated immunoassay conditions, the specified antibodies bind preferentially to a particular peptide and do not bind in a significant amount to other proteins in the sample. Preferably, selective binding includes binding at about or above 1.5 times assay background and the absence of significant binding is less than 1.5 times assay background.

This invention also contemplates antibodies that compete for binding to natural ADAM10 interactors or ADAM10 ligands. In other words, the present invention provides antibodies that disrupt interactions between ADAM10 and its binding partners. The antibody optionally can have either an antagonistic or agonistic function as compared to the antigen.

The antibody can bind an ADAM10 polypeptide in vitro, ex vivo or in vivo. Optionally, the antibody of the invention is labeled with a detectable moiety. For example, the detectable moiety can be selected from the group consisting of a fluorescent moiety, an enzyme-linked moiety, a biotin moiety and a radiolabeled moiety. The antibody can be used in techniques or procedures such as diagnostics, screening, or imaging. Anti-idiotypic antibodies and affinity matured antibodies are also considered to be part of the invention.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind ADAM10 are provided. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. In one embodiment of the invention, the "humanized" antibody is a human version of the antibody produced by a germ line mutant animal. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In one embodiment, the present invention provides a humanized version of an antibody, comprising at least one, two, three, four, or up to all CDRs of a monoclonal antibody that specifically binds to ADAM10. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Methods of Decreasing Infection

The present invention provides a method of decreasing infection in a cell by a pathogen comprising decreasing expression or activity of ADAM10. As stated above, an infection can be a viral infection, bacterial infection, fungal infection or a parasitic infection, to name a few. A decrease or inhibition of infection can occur in a cell, in vitro, ex vivo or in vivo. Expression of an ADAM10 nucleic acid or gene can be inhibited. Similarly, the activity of an ADAM10 gene product (for example, a an ADAM10 mRNA, ADAM10 polypeptide or ADAM10 protein) can be inhibited. Inhibition or a decrease in expression does not have to be complete as this can range from a slight decrease in expression to complete ablation of expression. For example, expression can be inhibited by about 5%, 10%, 20%, 30%, 40%, 50%, 60%, 70%, 80%, 90%, 95%, 99%, 100% or any percentage in between as compared to a control cell wherein the expression of ADAM10 has not been decreased or inhibited. Similarly, inhibition or decrease in the activity of a gene product does not have to be complete as this can range from a slight decrease to complete ablation of the activity of the gene product. For example, the activity of a gene product can be inhibited by about 5%, 10%, 20%, 30%, 40%, 50%, 60%, 70%, 80%, 90%, 95%, 99%, 100% or any percentage in between as compared to a control cell wherein activity of a ADAM10 gene product has not been decreased or inhibited.

The cells of the present invention can be prokaryotic or eukaryotic, such as a cell from an insect, fish, crustacean, mammal, bird, reptile, yeast or a bacterium, such as *E. coli*. The cell can be part of an organism, or part of a cell culture, such as a culture of mammalian cells or a bacterial culture. Therefore, the cell can also be part of a population of cells. The cell(s) can also be in a subject.

Examples of viral infections include but are not limited to, infections caused by all RNA viruses (including negative stranded RNA viruses, positive stranded RNA viruses, double stranded RNA viruses and retroviruses) and DNA viruses. Examples of viruses include, but are not limited to, HIV (including HIV-1 and HIV-2), parvovirus, papillomaviruses, measles, filovirus (for example, Ebola, Marburg), SARS (severe acute respiratory syndrome) virus, hantaviruses, influenza viruses (e.g., influenza A, B and C viruses), hepatitis viruses A to G, caliciviruses, astroviruses, rotaviruses, reovirus, coronaviruses, (for example, human respiratory coronavirus and SARS coronavirus (SARS-CoV), picornaviruses, (for example, human rhinovirus and enterovirus), Ebola virus, human herpesvirus (such as, HSV-1-9, including zoster, Epstein-Barr, and human cytomegalovirus), foot and mouth disease virus, human adenovirus, adeno-associated virus, respiratory syncytial virus (RSV), smallpox virus (variola), cowpox, monkey pox, vaccinia, polio, viral meningitis and hantaviruses.

For animals, viruses include, but are not limited to, the animal counterpart to any above listed human virus, avian influenza (for example, strains H5N1, H5N2, H7N1, H7N7 and H9N2), and animal retroviruses, such as simian immunodeficiency virus, avian immunodeficiency virus, pseudocowpox, bovine immunodeficiency virus, feline immunodeficiency virus, equine infectious anemia virus, caprine arthritis encephalitis virus and visna virus.

Examples of bacterial infections include, but are not limited to infections caused by the following bacteria: *Listeria* (sp.), *Mycobacterium tuberculosis, Rickettsia* (all types), *Ehrlichia, Chylamida*. Further examples of bacteria that can be targeted by the present methods include *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other Rickettsial species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

Examples of parasitic infections include, but are not limited to infections caused by the following parasites: *Cryptosporidium, Plasmodium* (all species) and American trypanosomes (*T. cruzi*).

Furthermore, examples of protozoan and fungal species contemplated within the present methods include, but are not limited to, *Plasmodium falciparum*, other *Plasmodium* species, *Toxoplasma gondii, Pneumocystis carinii, Trypanosoma cruzi*, other trypanosomal species, *Leishmania donovani*, other *Leishmania* species, *Theileria annulata*, other *Theileria* species, *Eimeria tenella*, other *Eimeria* species, *Histoplasma capsulatum, Cryptococcus neoformans, Blastomyces dermatitidis, Coccidioides immitis, Paracoccidioides brasiliensis, Penicillium marneffei*, and *Candida* species.

In the methods of the present invention, expression or activity of ADAM10 can be decreased by contacting the cell with a composition comprising a chemical, a small or large molecule (organic or inorganic), a drug, a protein, a peptide, a cDNA, an antibody, a morpholino, a triple helix molecule, an siRNA, a shRNA, an miRNA, an antisense RNA, a ribozyme or any other compound now known or identified in the future that decreases the expression and/or activity of ADAM10. A composition can also be a complex mixture or "cocktail" of the compositions described herein.

These compositions can be used alone or in combination with other therapeutic agents such as anti-viral compounds, antibacterial agents, antifungal agents, antiparasitic agents, anti-inflammatory agents, anti-cancer agents, etc. All of the compounds described herein can be contacted with a cell in vitro, ex vivo or in vivo.

Examples of antiviral compounds include, but are not limited to, amantadine, rimantadine, zanamavir and oseltamavir (Tamiflu) for the treatment of flu and its associated symptoms. Antiviral compounds useful in the treatment of HIV include Combivir® (lamivudine-zidovudine), Crixivan® (indinavir), Emtriva® (emtricitabine), Epivir® (lamivudine), Fortovase® (saquinavir-sg), Hivid® (zalcitabine), Invirase® (saquinavir-hg), Kaletra® (lopinavir-ritonavir), Lexiva™ (fosamprenavir), Norvir® (ritonavir), Retrovir® (zidovudine) Sustiva® (efavirenz), Videx EC® (didanosine), Videx® (didanosine), Viracept® (nelfinavir) Viramune® (nevirapine), Zerit® (stavudine), Ziagen® (abacavir), Fuzeon® (enfuvirtide) Rescriptor® (delavirdine), Reyataz® (atazanavir), Trizivir® (abacavir-lamivudine-zidovudine) Viread® (tenofovir disoproxil fumarate) and Agenerase® (amprenavir). Other antiviral compounds useful in the treatment of Ebola and other filoviruses include ribavirin and cyanovirin-N(CV-N). For the treatment of herpes virus, Zovirax® (acyclovir) is available. Antibacterial agents include, but are not limited to, antibiotics (for example, penicillin and ampicillin), sulfa Drugs and folic acid Analogs, Beta-Lactams, aminoglycosides, tetracyclines, macrolides, lincosamides, streptogramins, fluoroquinolones, rifampin, mupirocin, cycloserine, aminocyclitol and oxazolidinones.

Antifungal agents include, but are not limited to, amphotericin, nystatin, terbinafine, itraconazole, fluconazole, ketoconazole, griselfulvin.

Antiparasitic agents include, but are not limited to, anthelmintics, antinematodal agents, antiplatyhelmintic agents, antiprotozoal agents, amebicides, antimalarials, antitrichomonal agents, aoccidiostats and trypanocidal agents.

Peptides

Peptides that inhibit ADAM10 activity are also provided herein. These peptides can be any peptide in a purified or non-purified form, such as peptides made of D- and/or L-configuration amino acids (m, for example, the form of random peptide libraries; see Lam et al., *Nature* 354:82-4, 1991), phosphopeptides (such as in the form of random or partially degenerate, directed phosphopeptide libraries; see, for example, Songyang et al., *Cell* 72:767-78, 1993).

siRNAs

Short interfering RNAs (siRNAs), also known as small interfering RNAs, are double-stranded RNAs that can induce sequence-specific post-transcriptional gene silencing, thereby decreasing gene expression. In some examples, siRNA molecules are about 19-23 nucleotides in length, such as at least 21 nucleotides, for example at least 23 nucleotides. In one example, siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends. The direction of dsRNA processing determines whether a sense or an antisense target RNA can be cleaved by the produced siRNA endonuclease complex. Thus, siRNAs can be used to modulate transcription, for example, by decreasing gene expression, such as ADAM10. The effects of siRNAs have been demonstrated in cells from a variety of organisms, including *Drosophila, C. elegans*, insects, frogs, plants, fingi, mice and humans (for example, WO 02/44321; Gitlin et al., *Nature*

418:430-4, 2002; Caplen et al., *Proc. Natl. Acad. Sci.* 98:9742-9747, 2001; and Elbashir et al., *Nature* 411:494-8, 2001).

Utilizing sequence analysis tools, one of skill in the art can design siRNAs to specifically target ADAM10 for decreased gene expression. siRNAs that inhibit or silence gene ADAM10 expression can be obtained from Ambion Inc. (2130 Woodward Austin, Tex. 78744-1832 USA) under catalog numbers 16704, 16706, 16708, 16708A, 16804, 16806, 16810, 16904. The siRNAs synthesized by Ambion Inc. can also be readily obtained by providing a GenBank Accession No. for a ADAM10 coding sequence (for example, NM_001110 or AF009615) or Entrez Gene ID No. 102 for the ADAM10 gene. The ADAM10 siRNAs available from Ambion can be selected from the group consisting of siRNA ID #104233, 103993, 103992, 9421, 147032, 147031, 112740, 9610 and 9517. siRNAs are also commercially available from Dharmacon, Inc.

Also provided herein are examples of siRNA sequences that can be utilized to decrease ADAM10 gene expression. Specifically, Table 2 provides sense RNA sequences and antisense RNA sequences for ADAM10. Therefore, any of the sense or antisense sequences set forth in Table 2 can be used alone or in combination with other sequences to inhibit gene expression. These sequences can comprise a 3'TT overhang and/or additional sequences that allow efficient cloning and expression of the siRNA sequences. These sequences were obtained by analyzing the open reading frame of the ADAM10 gene. Therefore, Table 2 provides the GenBank Accession No. AF009615 for the ADAM10 mRNA, the length of the mRNA, and the ORF region of the mRNA, Table 2 also provides the start site of the sequence in the ADAM10 open reading frame. The start site for the target sequence is indicated in the Name column and in the Start column. The Name column also provides a GenBank Accession No. identifier for each sequence. Thus, it would be clear that a row in Table 2 that had the Name AF009615_siRNA_1310 indicates that the sense and antisense sequences correspond to GenBank Accession No. AF009615 and the start site for the target sequence is nucleotide 1310 of the mRNA set forth under AF009615 which is in the ADAM10 ORF (nucleotides 470-2716 of the mRNA set forth under AF009615). For example, a target sequence for the ADAM10 gene starts at position 1310 of the sequence set forth under AF009615 that is in the open reading frame of the ADAM10 gene. Therefore, a sequence comprising SEQ ID NO: 1 and/or a sequence comprising SEQ ID NO: 2 are two sequences that can be utilized to target ADAM10 and decrease ADAM10 gene expression. Similarly, a sequence comprising SEQ ID NO: 3 and/or a sequence comprising SEQ ID NO: 4 can be utilized to target ADAM10 expression. These examples are not meant to be limiting and pertain to every sense and antisense RNA sequence set forth in Table 2. Sequences comprising the sense and antisense RNA sequences set forth herein can be utilized to inhibit gene expression in any cell (eukaryotic or prokaryotic), animal or any other organism. Additional sequences comprising the sense and antisense sequences that can be utilized are:

```
Sense:      GCUAAUGGCUGGAUUUAUUUU (SEQ ID NO: 53)
Antisense:  AAUAAAUCCAGCCAUUAGCUU (SEQ ID NO: 54)

Sense:      GGACAAACUUAACAACAAUUU (SEQ ID NO: 55)
Antisense:  AUUGUUGUUAAGUUUGUCCUU (SEQ ID NO: 56)

Sense:      CCCAAAGUCUCUCACAUUAUU (SEQ ID NO: 57)
Antisense:  UAAUGUGAGAGACUUUGGGUU (SEQ ID NO: 58)

Sense:      GCAAGGGAAGGAAUAUGUAUU (SEQ ID NO: 59)
Antisense:  UACAUAUUCCUUCCCUUGCUU (SEQ ID NO: 60)
```

All of the sequences disclosed herein can be cloned into vectors and utilized in vitro, ex vivo or in vivo to decrease gene expression.

TABLE 2

| Gene Name: | ADAM10 | Accession: | AF009615 | GI: | 2393946 |
|---|---|---|---|---|---|
| Organism: | *Homo sapiens* | Length: | 3410 | ORF Region: | 470-2716 |
| Locus: | | Blast database: | Human | ORF GC % | 41.62 |
| Defintion: | *Homo sapiens* ADAM10 (ADAM10) mRNA, complete cds. | | | | |
| Sequence: | AF009615 | | | | |
| Date | Sun Dec 04 10:25:45 PST 2005 | | | | |

| Name | Start | Sense RNA Sequence 5'-3' | Antisense RNA Sequence 5'-3' | Region | GC % |
|---|---|---|---|---|---|
| AF009615_siRNA_1310 | 1310 | GCUGAUGAGAAGGACCCUA (SEQ ID NO: 1) | UAGGGUCCUUCUCAUCAGC (SEQ ID NO: 2) | ORF | 52.63157895 |
| AF009615_siRNA_1575 | 1575 | GGUCUCAUGUACCUCCCAA (SEQ ID NO: 3) | UUGGGAGGUACAUGAGACC (SEQ ID NO: 4) | ORF | 52.63157895 |
| AF009615_siRNA_1613 | 1613 | GCUCACGAAGUUGGACAUA (SEQ ID NO: 5) | UAUGUCCAACUUCGUGAGC (SEQ ID NO: 6) | ORF | 47.36842105 |
| AF009615_siRNA_1665 | 1665 | GCACACCAGGAGAAUCUAA (SEQ ID NO: 7) | UUAGAUUCUCCUGGUGUGC (SEQ ID NO: 8) | ORF | 47.36842105 |
| AF009615_siRNA_1670 | 1670 | CCAGGAGAAUCUAAGAAUU (SEQ ID NO: 9) | AAUUCUUAGAUUCUCCUGG (SEQ ID NO: 10) | ORF | 36.84210526 |
| AF009615_siRNA_1837 | 1837 | CCAACCUAUUUGUGGAAAU (SEQ ID NO: 11) | AUUUCCACAAAUAGGUUGG (SEQ ID NO: 12) | ORF | 36.84210526 |

TABLE 2-continued

| | | | | | |
|---|---|---|---|---|---|
| AF009615_siRNA_1967 | 1967 | GGGAAACAGUGCAGUCCAA (SEQ ID NO: 13) | UUGGACUGCACUGUUUCCC (SEQ ID NO: 14) | ORF | 52.63157895 |
| AF009615_siRNA_2417 | 2417 | GCUGAUGGUCCUCUAGCUA (SEQ ID NO: 15) | UAGCUAGAGGACCAUCAGC (SEQ ID NO: 16) | ORF | 52.63157895 |
| AF009615_siRNA_2495 | 2495 | GCUCAUUGGUGGGCAGUAU (SEQ ID NO: 17) | AUACUGCCCACCAAUGAGC (SEQ ID NO: 18) | ORF | 52.63157895 |
| AF009615_siRNA_2539 | 2539 | GCUAAUGGCUGGAUUUAUU (SEQ ID NO: 19) | AAUAAAUCCAGCCAUUAGC (SEQ ID NO: 20) | ORF | 36.84210526 | shRNA shRNA (short hairpin RNA) is a DNA molecule that can be cloned into expression vectors to express siRNA (19-29 nt RNA duplex) for RNAi interference studies. shRNA has the following structural features: a short nucleotide sequence ranging from about 19-29 nucleotides derived from the target gene, followed by a short spacer of about 4-15 nucleotides (i.e. loop) and about a 19-29 nucleotide sequence that is the reverse complement of the initial target sequence. For example, a sense siRNA sequence (SEQ ID NO: 1) for ADAM10 can be utilized to design an shRNA.

as self-complementary hairpin structures that are cleaved by the nuclear RNase III Drosha (See Zeng et al., "Recognition and cleavage of primary microRNA precursors by the nuclear processing enzyme Drosha," *Embo J* 24:138-48 (2005)). This processing generates small hairpin precursor miRNAs (pre-miRNAs), approximately 70 nucleotides in length, which are exported to the cytoplasm where they are further processed by DICER into ~22 nucleotide miRNAs. In the cytoplasm, the processed miRNAs incorporate into miRNA-containing RNA-induced silencing complexes (miRISCs) that function

```
Top Strand       5'-CACCGCTGATGAGAAGGACCCTACGAATAGGGTCCTTCTCATCAGC-3'  (SEQ ID NO: 21)
Bottom Strand    5'-AAAAGCTGATGAGAAGGACCCTATTCGTAGGGTCCTTCTCATCAGC-3'  (SEQ ID NO: 22)
ds Oligo         5'-CACCGCTGATGAGAAGGACCCTACGAATAGGGTCCTTCTCATCAGC-3'  (SEQ ID NO: 23)
for ADAM10          ||||||||||||||||||||||||||||||||||||||||||
                 3'-CGACTACTCTTCCTGGGATGCTTATCCCAGGAAGAGTACTCGAAAA-5'  (SEQ ID NO: 24)
```

Therefore, any sense sequence set forth in Table 1 can be linked to its corresponding antisense sequence with a linker or loop of 4 to 15 nucleotides, or more, to make a top strand for an shRNA. The bottom strand is the reverse complement of the top strand. As illustrated above, since the shRNA is doublestranded, the "U"s in the sequences set forth in Table 2 are replaced with "T"s to make double stranded DNA oligos. The top strand and the bottom strand are then annealed to form the double stranded shRNA. As mentioned above, the top and bottom strand can have overhangs or additional sequences to facilitate cloning into an expression vector. These vectors can then be delivered to a cell via routine methods and those described herein to express the shRNA and effect decreased ADAM10 expression.

miRNA

MicroRNAs (miRNAs) are small, RNA molecules encoded in the genomes of plants and animals. MicroRNAs are naturally occurring regulatory sequences found embedded in ~2% of RNA polymerase II-driven primary transcripts as siRNAs do to degrade their homologous target mRNAs (See Cullen, "Transcription and processing of human microRNA precursors,". *Mol Cell* 16:861-5). These highly conserved, ~22-mer RNAs regulate the expression of genes by binding to the 3'-untranslated regions (3'-UTR) of specific mRNAs. Nonlimiting examples of miRNAs for ADAM10 are set forth below. miRNAs can be utilized in a lentiviral delivery system to achieve efficient knockdown of genes (See Stegmeier et al. "A lentiviral microRNA-based system for single-copy polymerase II-regulated RNA interference in mammalian cells" *Proc Natl Acad Sci USA*. 2005 Sep. 13; 102(37):13212-7.). The following is an example of a double stranded oligo suitable for cloning into a vector. One of skill in the art would anneal the top and bottom strand to generate a double-stranded oligo with 4-nucleotide overhangs suitable for directional cloning into, for example, Invitrogen's pcDNA™ 6.2-GW/miR or pcDNA™ 6.2-GW/EmGFP-miR vectors.

```
Top           5'-TGCTGTATCTGGGCAATCACAGCTTCGTTTTGGCCACTGACTGACGAAGCTGTTTGCCCAGATA-3'  (SEQ. ID NO: 39)
Strand Bottom        5'-CCTGTATCTGGGCAAACAGCTTCGTCAGTCAGTGGCCAAAACGAAGCTGTGATTGCCCAGATAC-3'  (SEQ. ID NO: 40)
Strand ds Oligo      5'-TGCTGTATCTGGGCAATCACAGCTTCGTTTTGGCCACTGACTGACGAAGCTGTTTGCCCAGATA-3'  (SEQ. ID NO: 41
for ADAM10       ||||||||||||||||||||||||||||||||||||||||||||||||||||||||||||||||
miRNA         3'-CATAGACCCGTTAGTGTCGAAGCAAAACCGGTGACTGACTGCTTCGACAAACGGGTCTATGTCC  (SEQ. ID NO: 42)
vector
```

Another example is provided below:

```
Top           5'-TGCTGATATTTGGGAAACGGAAAGGAGTTTTGGCCACTGACTGACTCCTTTCCTTCCCAAATAT-3' (SEQ. ID NO: 43)
Strand Bottom        5'-CCTGATATTTGGGAAGGAAAGGAGTCAGTCAGTGGCCAAAACTCCTTTCCGTTTCCCAAATATC-3' (SEQ. ID NO: 44)
Strand ds Oligo      5'-TGCTGATATTTGGGAAACGGAAAGGAGTTTTGGCCACTGACTGACTCCTTTCCTTCCCAAATAT-3' (SEQ. ID NO: 45)
for ADAM10       ||||||||||||||||||||||||||||||||||||||||||||||||||||||||||||||
miRNA         3'-CTATAAACCCTTTGCCTTTCCTCAAAACCGGTGACTGACTGAGGAAAGGAAGGGTTTATAGTCC-5' (SEQ. ID NO: 46)
vector
```

Ribozymes

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Methods of using ribozymes to decrease or inhibit RNA expression are known in the art (for example see Kashani-Sabet, *J. Investig. Dermatol. Symp. Proc.*, 7:76-78, 2002).

Examples of ribozymes that can be utilized in the methods of the present invention include, but are not limited to, 5'ucggucugugaacugaugaguccgugaggacgaaacauaggccaaa-3'(SEQ ID NO: 47), a ribozyme that targets the ADAM10 mRNA sequence 5'-uuuggccuaugucuucacagaccga-3' (SEQ ID NO: 48) (this sequence corresponds to human ADAM10 mRNA nucleotide positions 939-963): Another example is 5'-cauagagcucugcugaugaguccgugaggacgaaacuaaaaauugc-3' (SEQ ID NO: 49), a ribozyme that targets human ADAM10 mRNA sequence 5'-gcaauuuuuaguccagagcucuaug-3' (SEQ ID NO: 50) (this sequence corresponds to human ADAM10 mRNA nucleotide positions 1978-2002). Yet another example is 5'-ccaguguuuaagcugaugaguccgugaggacgaaacuucuucuuac-3' (SEQ ID NO: 51), a ribozyme that targets the human ADAM10 mRNA sequence 5'-guaagaagaaguccuuaaacacugg-3'(SEQ ID NO: 52) (this corresponds to human ADAM10 mRNA nucleotide positions 1058-1082).

The ribozymes set forth herein and others designed to target ADAM10 mRNA sequences can be expressed from a plasmid by utilizing an RNA polymerase III-based promoter, including a downstream TTTTT following the 3' end of the ribozyme transcript. The TTTTT would serve as a transcription termination signal.

Antisense Nucleic Acids

Generally, the term "antisense" refers to a nucleic acid molecule capable of hybridizing to a portion of an RNA sequence (such as mRNA) by virtue of some sequence complementarity. The antisense nucleic acids disclosed herein can be oligonucleotides that are double-stranded or single-stranded, RNA or DNA or a modification or derivative thereof, which can be directly administered to a cell (for example by administering the antisense molecule to the subject), or which can be produced intracellularly by transcription of exogenous, introduced sequences (for example by administering to the subject a vector that includes the antisense molecule under control of a promoter).

Antisense nucleic acids are polynucleotides, for example nucleic acid molecules that are at least 6 nucleotides in length, at least 10 nucleotides, at least 15 nucleotides, at least 20 nucleotides, at least 100 nucleotides, at least 200 nucleotides, such as 6 to 100 nucleotides. However, antisense molecules can be much longer. In particular examples, the nucleotide is modified at one or more base moiety, sugar moiety, or phosphate backbone (or combinations thereof), and can include other appending groups such as peptides, or agents facilitating transport across the cell membrane (Letsinger et al., *Proc. Natl. Acad. Sci. USA* 1989, 86:6553-6; Lemaitre et al., *Proc. Natl. Acad. Sci. USA* 1987, 84:648-52; WO 88/09810) or blood-brain barrier (WO 89/10134), hybridization triggered cleavage agents (Krol et al., *BioTechniques* 1988, 6:958-76) or intercalating agents (Zon, *Pharm. Res.* 5:539-49, 1988).

Examples of modified base moieties include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl)uracil, and 2,6-diaminopurine.

Examples of modified sugar moieties include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In a particular example, an antisense molecule is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625-41, 1987). The oligonucleotide can be conjugated to another molecule, such as a peptide, hybridization triggered cross-linking agent, transport agent, or hybridization-triggered cleavage agent. Oligonucleotides can include a targeting moiety that enhances uptake of the molecule by host cells. The targeting moiety can be a specific binding molecule, such as an antibody or fragment thereof that recognizes a molecule present on the surface of the host cell.

In a specific example, antisense molecules that recognize a nucleic acid set forth herein, include a catalytic RNA or a ribozyme (for example see WO 90/11364; WO 95/06764; and Sarver et al., *Science* 247:1222-5, 1990). Conjugates of antisense with a metal complex, such as terpyridylCu (II), capable of mediating mRNA hydrolysis, are described in Bashkin et al. (*Appl. Biochem Biotechnol.* 54:43-56, 1995). In one example, the antisense nucleotide is a 2'-0-methylribonucleotide (Inoue et al., *Nucl. Acids Res.* 15:6131-48, 1987), or a chimeric RNA-DNA analogue (Inoue et al., *FEBS Lett.* 215:327-30, 1987).

Examples of antisense nucleic acid molecules that can be utilized to decrease ADAM10 expression in the methods of the present invention, include, but are not limited to, TCCT-TCCTCACCACGTGACG (SEQ ID NO: 25), GGCAG-GAGAAACGGCGAAGC (SEQ ID NO: 26), GTCTTCAT-GTGAGACTGCTC (SEQ ID NO: 27) CTACACCAGTCATCTGGTAT (SEQ ID NO: 28), TTCT-CATCAGCAGTTGTATT (SEQ ID NO: 29), CAGCAT-TCATCTTTACACTG (SEQ ID NO: 30), CATAATTCTT-TATCATCTTT (SEQ ID NO: 31), CATCACAGTAACCTCTAAAA (SEQ ID NO: 32), AGCAATTCCCATAAGTAATA (SEQ ID ON: 33), GTGAAGTTTTCCCATTGTAG (SEQ ID NO: 34), GGTCTGAGGATATGATCTCT (SEQ ID NO: 35), TACAT-GTCTGCATATAACAA (SEQ ID NO: 36), TGTTTACAAT-TGCACACAGA (SEQ ID NO: 37) and GAGTATGTCAAT-TAAACAGT (SEQ ID NO: 38). These antisense nucleic acid molecules and the methods of utilizing same to decrease ADAM10 expression are set forth in U.S. Pat. No. 6,228,648 which is incorporated in its entirety by this reference.

Morpholinos

Morpholinos are synthetic antisense oligos that can block access of other molecules to small (~25 base) regions of ribonucleic acid (RNA). Morpholinos are often used to determine gene function using reverse genetics methods by blocking access to mRNA. Morpholinos, usually 25 bases in length, bind to complementary sequences of RNA by standard nucleic acid base-pairing. Unlike many antisense structural types (e.g. phosphorothioates, siRNA), Morpholinos do not degrade their target RNA molecules. Instead, Morpholinos act by "steric hindrance", binding to a target sequence within an RNA and simply interfering with molecules which might otherwise interact with the RNA Morpholinos have been used in mammals, ranging from mice to humans.

Bound to the 5'-untranslated region of messenger RNA (mRNA), Morpholinos can interfere with progression of the ribosomal initiation complex from the 5' cap to the start codon. This prevents translation of the coding region of the targeted transcript (called "knocking down" gene expression). Morpholinos can also interfere with pre-mRNA processing steps, usually by preventing the splice-directing snRNP complexes from binding to their targets at the borders of introns on a strand of pre-RNA. Preventing U1 (at the donor site) or U2/U5 (at the polypyrimidine moiety & acceptor site) from binding can cause modified splicing, commonly leading to exclusions of exons from the mature mRNA. Targeting some splice targets results in intron inclusions, while activation of cryptic splice sites can lead to partial inclusions or exclusions. Targets of U11/U12 snRNPs can also be blocked. Splice modification can be conveniently assayed by reverse-transcriptase polymerase chain reaction (RT-PCR) and is seen as a band shift after gel electrophoresis of RT-PCR products. Methods of designing, making and utilizing morpholinos are disclosed in U.S. Pat. No. 6,867,349 which is incorporated herein by reference in its entirety.

Compounds

Compounds that decrease expression and/or activity of ADAM10 include, but are not limited to, the compounds set forth in U.S. Pat. Nos. 6,172,064, 6,329,400, and 6,191,150. All of the compounds disclosed in U.S. Pat. Nos. 6,172,064, 6,329,400 and 6,191,150 are incorporated herein by this reference as are the methods of making and utilizing these compounds for decreasing the expression of ADAM10 in a cell, in vitro, ex vivo and in vivo. These compounds can be utilized in a method of decreasing infection in a cell by a pathogen comprising contacting a cell with a compound set forth in U.S. Pat. Nos. 6,172,064, 6,329,400, and 6,191,150 that decreases expression or activity of ADAM10. Also contemplated by the present invention are the pharmaceutically acceptable salt, solvate, biohydrolyzable ester, biohydrolyzable amide, affinity reagent or prodrug of these compounds.

In one example a cell is contacted with (2R,3S)-3-(Formyl-hydroxyamino)-2-(3-phenyl-1-propyl)butanoic Acid [(1S)-2,2-Dimethyl-1-(methylcarbamoyl)-1-propyl]amide. This compound has the chemical structure shown below.

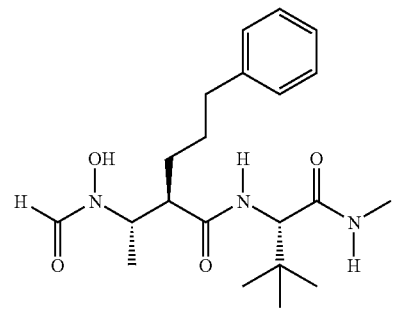

This compound can be synthesized as follows:

Methyl (2R,3R)-2-[(2E)-3-Phenyl-2-propen-1-yl]-3-hydroxybutanoate

To a solution of diisopropylamine (47.1 g, 466.1 mmol) in THF (500 mL) cooled to −50.degree. C. is added n-butyl-lithium (466.1 mmol, 2.5M in hexanes) and the resulting solution is stirred at −50.degree. C. for 0.5 h. The reaction mixture is cooled to −78.degree. C. followed by slow addition of methyl (3R)-3-hydroxybutanoate (25 g, 211.9 mmol). After 0.5 h a solution of cinnamyl bromide (45.9 g, 233.0 mmol) in HMPA (10 mL) is added and the reaction mixture is allowed to warm to 0.degree. C. and stirred for 16 h. The reaction mixture is quenched by addition 30 mL of saturated aqueous ammonium chloride solution, is poured into 400 mL of 1 M hydrochloric acid, and is extracted with two 500 mL portions of ethyl acetate. The combined organic layers are dried over magnesium sulfate, concentrated in vacuo, and purified by silica gel chromatography (elution with 25% ethyl acetate-hexanes) to afford methyl (2R,3R)-2-[(2E)-3-phenyl-2-propen-1-yl]-3-hydroxybutanoate as a yellow oil (42 g, 85% yield).

$^1$H NMR (400 MHz, CDCl$_3$) δ 7.32-7.18 (m, 5H), 6.44 (d, 1H), 6.13 (m, 1H), 3.98 (m, 1H), 3.69 (s, 3H), 2.56 (m, 4H), 1.25 (t, 3H) ppm.

ESI-MS m/z 257.2 (M+Na)$^+$.

Methyl (2R,3R)-2-(3-Phenyl-1-propyl)-3-hydroxybutanoate

A solution of methyl (2R,3R)-2-[(2E)-3-phenyl-2-propen-1-yl]-3-hydroxybutanoate (42.0 g, 179.5 mmol) in 400 mL of methanol is treated with 400 mg of 10% palladium on carbon. The resulting suspension is repeatedly evacuated and purged with a hydrogen balloon, then stirred under 1 atmosphere pressure of hydrogen gas for 16 h. The catalyst is filtered and the filtrate is concentrated in vacuo to provide methyl (2R,3R)-2-(3-phenyl-1-propyl)-3-hydroxybutanoate as an oil (42.2 g, 100% yield).

$^1$H NMR (400 MHz, CDCl$_3$) δ 7.25 (m, 2H), 7.17 (m, 3H), 3.88 (m, 1H), 3.69 (s, 3H), 2.61 (m, 2H), 2.42 (m, 2H), 1.72 (m, 1H), 1.62 (m, 3H), 1.19 (d, 3H) ppm.

ESI-MS m/z 259.2 M+Na$^+$.

(2R,3R)-2-(3-Phenyl-1-propyl)-3-hydroxybutanoic Acid

To a solution of methyl (2R,3R)-2-(3-phenyl-1-propyl)-3-hydroxybutanoate (42.2 g, 179.5 mmol) in THF-methanol (3:1, 535 mL) is added 2 M aqueous sodium hydroxide solution (135 mL, 269.3 mmol). The solution is stirred at 23.degree. C. for 20 h, then concentrated and extracted with hexanes (100 mL). The aqueous layer is acidified to pH=3 with saturated aqueous sodium bisulfate and is extracted with two 500 mL portions of ethyl acetate. The combined organic layers are dried over anhydrous magnesium sulfate and concentrated under reduced pressure to provide (2R,3R)-2-(3-phenyl-1-propyl)-3-hydroxybutanoic acid as an oil (33.0 g, 83% yield).

$^1$H NMR (400 MHz, CDCl$_3$) δ 7.28 (m, 2H), 7.16 (m, 3H), 3.93 (m, 1H), 2.63 (m, 2H), 2.43 (m, 1H), 1.69 (m, 4H), 1.26 (d, 3H) ppm.

ESI-MS m/z 221.3 (M−H)$^-$ (2R,3R)-2-(3-Phenyl-1-propyl)-3-hydroxybutanoic Acid 2 Tetrahydropyranyloxyamide To a solution of (2R,3R)-2-(3-phenyl-1-propyl)-3-hydroxybutanoic acid (33.0 g, 148.7 mmol) in dichloromethane (300 mL) is added 2-tetrahydropyranyloxyamine (18.3 g, 156.1 mmol) and EDC (31.2 g, 163.5 mmol). The resulting solution is stirred at 23.degree. C. for 16 h. then diluted with dichloromethane (500 mL) and washed sequentially with 1 M hydrochloric acid, saturated aqueous sodium bicarbonate solution, and saturated aqueous sodium chloride solution. The reaction mixture is dried over anhydrous magnesium sulfate and concentrated under reduced pressure to provide (2R,3R)-2-(3-phenyl-1-propyl)-3-hydroxybutanoic acid 2-tetrahydropyranyloxyamide as a foam (47.8 g, 100% yield).

$^1$H NMR (400 MHz, CDCl$_3$) δ 8.66 (bs, 1H), 7.25 (m, 2H), 7.17 (m, 3H), 4.94 (m, 1H), 3.89 (m, 2H), 3.61 (m, 1H), 2.62 (t, 2H), 1.93 (m, 1H), 1.78 (m, 4H), 1.66 (m, 6H), 1.23 (d, 3H)

ESI-MS m/z 320.4 (M−H)$^-$ (3R,4S)-1-(2-Tetrahydropyranyloxy)-3-(3-phenyl-1-propyl)-4-methylazetidin-2-one To a solution of (2R,3R)-2-(3-phenyl-1-propyl)-3-hydroxybutanoic acid 2-tetrahydropyranyloxyamide (47.8 g, 148.7 mmol) in 150 mL of dichloromethane at 0.degree. C. is added pyridine (64 mL) and methanesulfonyl chloride (20.4 g, 178.4 mmol). The resulting solution is allowed to warm to 23.degree. C. and is stirred at 23.degree. C. for 14 h, concentrated in vacuo, and diluted with dichloromethane (500 mL). The organic layer is washed with 1 M hydrochloric acid, saturated aqueous sodium chloride solution, dried over anhydrous magnesium sulfate, and concentrated to provide the desired methanesulfonate intermediate.

A suspension of potassium carbonate (61.5 g) in acetone (500 mL) is heated to reflux for 1 h. A solution of the above methanesulfonate in acetone (1000 mL) is added and the resulting suspension is heated at reflux for 28 h. The mixture is allowed to cool to 25.degree. C. and is filtered, concentrated under reduced pressure, and purified by silica gel chromatography (elution with 3:1 hexanes-ethyl acetate) to provide (3R,4S)-1-(2-tetrahydropyranyloxy)-3-(3-phenyl-1-propyl)-4-methylazetidin-2-one as an oil (34.0 g, 75% yield).

$^1$H NMR (400 MHz, CDCl$_3$) δ 7.25 (m, 2H), 7.17 (m, 3H), 5.13 (m, 0.5H), 4.99 (m, 0.5H), 4.15-3.98 (m, 2H), 3.64 (m, 1H), 2.93 (m, 1H), 2.67 (m, 2H), 1.89-1.51 (m, 10H), 1.28 (d, 1.5H), 1.26 (d, 1.5H) ppm.

ESI-MS m/z 326.4 (M+Na)$^+$ (2R,3S)-2-(3-Phenyl-1-propyl)-3-(2-tetrahydropyranyloxyamino)butanoic Acid To a solution of (3R,4S)-1-(2-tetrahydropyranyloxy)-3-(3-phenyl-1-propyl)-4-methylazetidin-2-one (20.5 g, 67.6 mmol) in dioxane (220 mL) is added 1 M aqueous sodium hydroxide (102 mL). The solution is stirred at 23.degree. C. for 20 h, then extracted with hexanes (200 mL). The aqueous layer is acidified to pH=3 with saturated aqueous sodium bisulfate solution, and is extracted with two 300 mL portions of ethyl acetate. The combined organics are washed with saturated aqueous sodium chloride, dried over anhydrous magnesium sulfate, and concentrated under reduced pressure to provide (2R,3S)-2-(3-phenyl-1-propyl)-3-(2-tetrahydropyranyloxyamino)butanoic acid as an oil (21.5 g, 99% yield).

$^1$H NMR (400 MHz, CDCl$_3$) δ 7.28 (m, 2H), 7.18 (m, 3H), 4.84 (m, 0.5H), 4.70 (m, 0.5H), 3.96 (m, 0.5H), 3.89 (m, 0.5H), 3.56 (m, 1H), 3.34 (m, 0.5H), 3.24 (m, 0.5H), 2.97 (m, 0.5H), 2.81 (m, 0.5H), 2.65 (m, 2H), 1.96-1.45 (m, 10H), 1.31 (m, 1H), 1.06 (d, 1.5H), 0.99 (d, 1.5H) ppm.

ESI-MS m/z 344.3 (M+H)$^+$.

(2R,3S)-2-(3-Phenyl-1-propyl)-3-(formyl-2-tetrahydropyranyloxyamino)butanoic Acid To a solution of (2R,3S)-2-(3-phenyl-1-propyl)-3-(2 tetrahydropyranyloxyamino)butanoic acid (21.4 g, 66.7 mmol) in pyridine (100 mL) at 0.degree. C. is added formic acetic anhydride (30 mL). The resulting solution is allowed to warm to 25.degree. C., stirred for 6 h, and then concentrated to dryness under reduced pressure. The resulting gum is dissolved in ethyl acetate (300 mL) and washed sequentially with 1 M hydrochloric acid (200 mL) and saturated aqueous sodium chloride solution. The organic layer is dried over anhydrous magnesium sulfate and concentrated under reduced pressure to provide (2R,3S)-2-(3-Phenyl-1-propyl)-3-(formyl-2-tetrahydropyranyloxyamino)butanoic acid as an oil (18.9 g, 81% yield).

ESI-MS m/z 372.3 (M+Na)$^+$.
ESI-MS m/z 348.4 (M−H)$^-$.

(2S)-2-tert-butoxycarbonylamino-3,3-dimethylbutanoic Acid Methylamide

To a solution of (2S)-2-tert-butoxycarbonylamino-3,3-dimethylbutanoic acid (120 g, 519 mmol) in dichloromethane (800 mL) is added 1,1-carbonyldiimidazole (88.4 g, 545 mmol). The resulting solution is stirred at 25.degree. C. for 1 h and methylamine hydrochloride (52.5 g, 779 mmol) and triethylamine (157.3 g, 1557 mmol) are added and the reaction is stirred for an additional 18 h. The mixture is diluted with dichloromethane (600 mL) and washed with 1 M hydrochloric acid and saturated aqueous sodium chloride. The organic layer is dried over anhydrous magnesium sulfate and concentrated in vacuo to provide (2S)-2-tert-butoxycarbonylamino-3,3-dimethylbutanoic acid methylamide as a white solid (126 g, 100% yield).

$^1$H NMR (400 MHz, CDCl$_3$) δ 5.81 (bs, 1H), 5.30 (m, 1H), 3.80 (d, 1H), 2.81 (d, 3H), 1.43 (s, 9H), 0.99 (s, 9H) ppm.
ESI-MS m/z 245.4 (M+H)$^+$.

(2S)-2-Amino-3,3-dimethylbutanoic Acid Methylamide

To a solution of (2S)-2-tert-butoxycarbonylamino-3,3-dimethylbutanoic acid methylamide (126 g, 519 mmol) in dichloromethane (320 mL) cooled at 0.degree. C. is added trifluoroacetic acid (320 mL). The resulting solution is allowed to warm to 25.degree. C. and is stirred for 18 h. The reaction mixture is concentrated, brought to pH=10 with 2 M sodium hydroxide, and extracted with 4:1 dichloromethane/isopropanol (1000 mL). The organic layer is washed with saturated aqueous sodium chloride, dried over anhydrous magnesium sulfate and concentrated under reduced pressure to provide (2S)-2-Amino-3,3-dimethylbutanoic acid methylamide (40.5 g, 79% yield) as a white solid.

$^1$H NMR (400 MHz, CDCl$_3$) δ 6.69 (bs, 1H), 3.10 (s, 1H), 2.82 (d, 3H), 1.50 (bs, 2H), 0.99 (s, 9H) ppm.
ESI-MS m/z 145.2 (M+H)$^+$.

(2R,3S)-3-(Formyl-2-tetrahydropyranyloxyamino)-2-(3-phenyl 1-propyl)butanoic Acid [(1S)-2,2-Dimethyl-1-(methylcarbamoyl)-1-propyl]amide To a solution of (2R,3S)-2-(3-phenyl-1-propyl)-3-(formyl-2-tetrahydropyranyloxyamino)buta noic acid (5.5 g, 15.76 mmol) in DMF (20 mL) is added BOP reagent (7.66 g, 17.34 mmol), HOBt (2.34 g, 17.34 mmol), and NMM (4.78 g, 47.28 mmol). After 30 min, addition of (2S)-2-Amino-3,3-dimethylbutanoic acid methylamide (3.4 g, 23.64) occurs and the resulting solution is stirred at 25.degree. C. for 20 h. The reaction mixture is poured into ethyl acetate/hexanes (1:1, 200 mL) and washed sequentially with 1 M hydrochloric acid, 1 M aqueous sodium carbonate, and saturated aqueous sodium chloride. The organic layer is dried over magnesium sulfate, concentrated in vacuo, and purified by silica gel chromatography (elution with 2:1 ethyl acetate-hexane) to provide (2R,3S)-3-(Formyl-2-tetrahydropyranyloxyamino)-2-(3-phenyl-1-propyl)butanoic acid [(1S)-2,2-dimethyl-1-(methylcarbamoyl)-1-propyl]amide as a white solid (2.7 g, 36% yield).

$^1$H NMR (400 MHz, CDCl$_3$) δ 8.40 and 8.02 (s, 1H), 7.22 (m, 2H), 7.08 (m, 3H), 6.38 (m, 1H), 5.88 (m, 1H), 4.82 (m, 1H), 4.38 and 3.56 (m, 1H), 4.22 (m, 1H), 3.94 (m, 1H), 2.74 (m, 3H), 2.56 (m, 3H), 1.82 (m, 2H), 1.74-1.42 (m, 10H), 1.28 and 1.22 (d, 3H), 0.96 (s, 9H) ppm.
ESI-MS m/z 498.4 (M+Na)$^+$ The present invention also provides methods of decreasing expression and/or activity of ADAM10 in a cell by contacting the cell with any of the ADAM10 inhibitory compounds set forth in U.S. Patent Publication No. US 2005/0227973 (U.S. application Ser. No. 10/498,338), for example, the ADAM10 inhibitors set forth in Table 4 of U.S. Patent Publication No. US 2005/0227973. The disclosure and the compounds set forth in US 2005/0227973 are hereby incorporated in its entirety by this reference. In particular, the present application provides methods of decreasing expression and/or activity of ADAM10 in a cell by contacting the cell with any of the compounds that preferentially or selectively inhibit ADAM10. Examples of these compounds include, but are not limited to the following compounds and the pharmaceutically acceptable salt, solvate, biohydrolyzable ester, biohydrolyzable amide, affinity reagent or prodrug of these compounds:

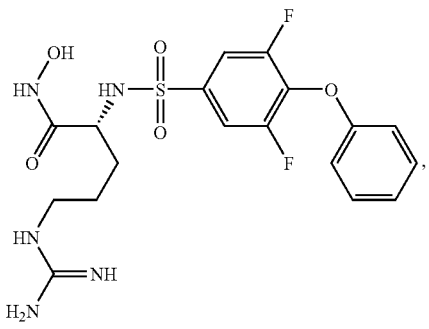

N2-{[3,5-difluoro-4-(phenyloxy)phenyl]sulfonyl}-N1-hydroxy-D-argininamide

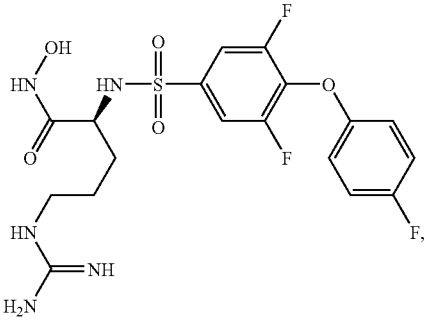

N2-({3,5-difluoro-4-[(4-fluorophenyl)oxy]phenyl}sulfonyl)-N1-hydroxy-D-argininamide

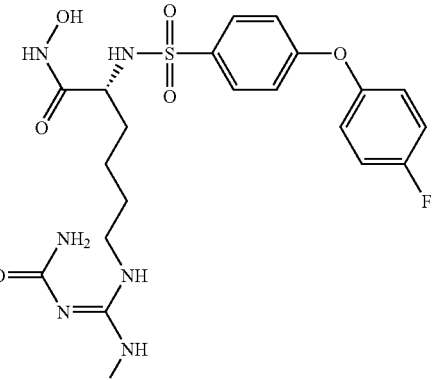

N6-[(E)-[(aminocarbonyl)imino](hydroxyamino)methyl]-N2-({4-[(4-fluorophenyl)oxy]phenyl}sulfonyl)-N1-hydroxy-D-lysinamide

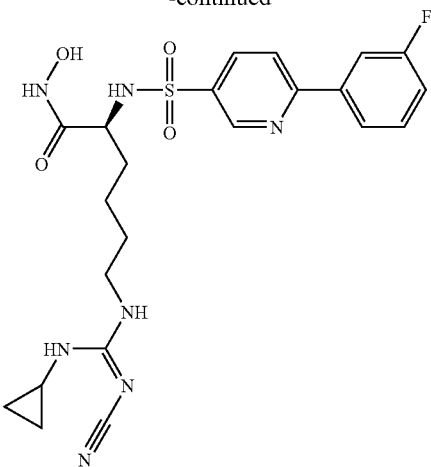

N6-[(Z)-(cyanoimino)(cyclopropylamino)methyl]-N2-{[6-(3-fluorophenyl)pyridin-3-yl]sulphonyl)-N1-hydroxy-D-lysinamide Synthesis of these and other ADAM10 inhibitors is disclosed in United States Publication No. 2005/0227973.

The compositions of the present invention can also comprise a compound of structural formula:

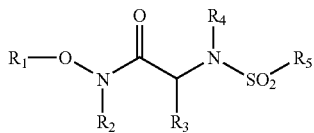

or a pharmaceutically acceptable salt thereof, wherein $R_1$ is selected from hydrogen, alkyl, alkanoyl, arylalkyl, and arylalkanoyl, wherein the arylalkyl and arylalkanoyl groups are unsubstituted or substituted with 1, 2, 3, 4, or 5 $R_6$ groups;

$R_6$ at each occurrence is independently selected from halogen, hydroxy, —$NO_2$, —$CO_2R_{10}$, —CN, alkyl, alkoxy, haloalkyl, and haloalkoxy;

$R_2$ is selected from hydrogen, alkyl, alkoxy, alkanoyl, arylalkyl and arylalkanoyl, wherein the arylalkyl and arylalkanoyl groups are unsubstituted or substituted with 1, 2, 3, 4, or 5 $R_6$ groups;

$R_3$ is —Z-Q-J, wherein

Z is selected from alkyl, alkoxyalkyl, alkylthioalkyl, and alkenyl, each of which is unsubstituted or substituted with 1 or 2 groups that are independently selected from alkoxy, hydroxy, and halogen;

Q is selected from a direct bond between Z and J, C(=O)—, aryl, heteroaryl, and heterocycloalkyl, wherein the aryl, heteroaryl, or heterocycloalkyl group is unsubstituted or substituted with 1 or 2 groups that are independently selected from alkyl, halogen, —$NRBR_9$, and alkoxy;

J is selected from —$NR_8R_9$, —$NR_7C(=O)NR_8R_9$, $NR_7C(=O)$ alkyl$NR_8R_9$, —$NR_7C(=O)OR_9$, C(=$NR_7$)$NR_8R_9$, and —NH—C(=$NR_7$)$NR_8R$, wherein $R_7$ is selected from H, CN, $NO_2$, alkyl, alkanoyl, arylalkanoyl and —C(=O)$NR_{10}R_{11}$, wherein $R_{10}$ and $R_{11}$ are independently selected from H, and alkyl, and $R_8$ and $R_9$ are independently selected from H, alkyl, hydroxy, alkoxy, alkoxyalkyl, heterocycloalkylalkyl, aryylalkyl, and heteroarylalkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently selected from alkyl, alkoxy, hydroxy, and halogen; or $R_7$, $R_8$, and the nitrogens to which they are attached form a 5, 6 or 7 membered heterocycloalkyl group that is unsubstituted or substituted with 1, 2 or 3 groups that are independently selected from alkyl, alkoxy, hydroxy, and halogen; and $R_9$ is selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups;

$R_4$ is selected from H, alkyl, and arylalkyl, wherein the arylalkyl group is unsubstituted or substituted with 1, 2, 3, 4, or 5 $R_6$ groups; and $R_5$ is -M-G-A, wherein M is selected from aryl and heteroaryl, wherein M is unsubstituted or substituted with 1, 2, 3, or 4 groups that are independently selected from halogen, alkyl, hydroxy, alkoxy, haloalkyl, —C N, haloalkoxy, and hydroxyalkyl;

G is selected from a direct bond between M and A, $CH_2$, -alkyl-O—, —O-alkyl-, O, S, SO, and $SO_2$;

A is selected from aryl and heteroaryl, wherein A is unsubstituted or substituted with 1, 2, 3, 4, or 5 groups that are independently selected from halogen, alkyl, alkoxy, haloalkyl, aryloxy, heteroaryloxy, arylalkoxy, heteroarylalkoxy, haloalkoxy, —CN, and $NO_2$;

with the proviso that when M is phenyl, G is a direct bond between M and A, and A is phenyl, then at least one of the four remaining hydrogens on the phenyl ring of M, of M-G-A, must be substituted with a group independently selected from halogen, alkyl, hydroxy, alkoxy, haloalkyl, —C N, haloalkoxy, and hydroxyalkyl;

The compound with the structural formula set forth above can also have $R_1$, wherein $R_1$ is selected from the group consisting of hydrogen, $C_1$-$C_6$ alkyl, phenyl $C_1$-$C_6$ alkyl, and phenyl $C_1$-$C_6$ alkanoyl, wherein the phenylalkyl and phenylalkanoyl groups are unsubstituted or substituted with 1, 2, 3, 4, or 5 RE groups, and $R_2$ is selected from the group consisting of hydrogen, $C_1$-$C_6$ alkyl, $C_1$-$C_6$ alkanoyl, phenyl $C_1$-$C_6$ alkyl and phenyl $C_1$-$C_6$ alkanoyl, wherein the phenylalkyl and phenylalkanoyl groups are unsubstituted or substituted with 1, 2, 3, 4, or 5 $R_6$ groups, wherein $R_6$ at each occurrence is independently selected from the group consisting of halogen, hydroxy, —$NO_2$, —CN, $C_1$-$C_6$ alkyl, $C_1$-$C_6$ alkoxy, $CF_3$, and $OCF_3$.

$R_3$ in the compound with the structural formula set forth above can also be Z-Q-J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 groups independently selected from $C_1$-$C_4$ alkyl, halogen, and $C_1$-$C_4$ alkoxy;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently selected from $C_1$-$C_4$ alkyl, halogen, and $C_1$-$C_4$ alkoxy;

J is —C(=$NR_7$)$NR_8R_9$ or —NH—C(=$NR_7$)$NR_8R_9$, wherein $R_7$ is selected from the group consisting of H, —CN, —$NO_2$, $C_1$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently selected from H and $C_1$-C6 alkyl, $R_8$ and $R_9$ are each independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$—C8 cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl C—C6 alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently selected from $C_1$-$C_6$ alkyl, $C_1$-$C_6$ alkoxy, hydroxy, and halogen; or $R_7$, $R_8$, and the nitrogens to which they are attached form a 5, 6 or 7 membered heterocycloalkyl group that is unsubstituted or substituted with 1, 2 or 3 groups that are independently selected from $C_1$-$C_6$ alkyl, $C_1$-$C_6$ alkoxy, hydroxy, and halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, thiomorpholinyl S-oxide, phenyl, naphthyl, thiomorpholinyl S,S-dioxide, pyrrolidinyl, pyridyl, pyridazyl, pyrimidyl, pyrazinyl, and imidazolyl, wherein each of the above is unsubstituted or substituted with 1, 2, 3, or 4 $R_6$ groups, wherein $R_6$ at each occurrence is independently selected from the group consisting of halogen, hydroxy, $NO_2$, C—C6 alkyl, $C_1$-$C_6$ alkoxy, $CF_3$, and $OCF_3$.

$R_5$ in the compound with the structural formula set forth above can be -M-G-A, wherein M is selected from the group consisting of phenyl, pyridyl, pyrimidyl, pyridazinyl, pyrazinyl, thiophenyl, and pyrrolyl, wherein M is unsubstituted or substituted with 1, 2, 3, or 4 groups that are independently selected from the group consisting of halogen, $C_1$-$C_6$ alkyl, hydroxy, $C_1$-$C_6$ alkoxy, halo $C_1$-$C_6$ alkyl, halo $C_1$-$C_6$ alkoxy, and hydroxy $C_1$-$C_6$ alkyl, G is selected from a direct bond between M and A, $CH_2$, O, S, SO, and $SO_2$;

A is selected from the group consisting of phenyl, naphthyl, pyridyl, pyrimidyl, pyridazyl, pyrazinyl, pyrrolyl, benzo[1,3]dioxyl, quinolinyl, isoquinolinyl, tetrahydroisoquinolinyl, tetrahydronaphthyl, and dihydronaphthyl, wherein each of the above is unsubstituted or substituted with 1, 2, 3, 4, or 5 groups that are independently selected from halogen, $C_1$-$C_6$ alkyl, $C_1$-$C_6$ alkoxy, halo $C_1$-$C_6$ alkyl, halo $C_1$-$C_6$ alkoxy, CN, and $NO_2$.

The compound with the formula set forth above can also be a formula wherein

R1 is hydrogen, $C_1$-$C_6$ alkyl or benzyl;

R2 is hydrogen, $C_1$-$C_6$ alkyl or benzyl; and

R3 is —Z-Q-J, wherein

Z is $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy;

Q is a direct bond between Z and J, —C(=O)—, piperidinyl, pyrrolyl, piperazinyl, imidazolidinyl, morpholinyl, thiomorpholinyl, azepanyl, or azocanyl wherein each of the above is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(—$NR_7$)$NR_8R_9$, wherein $R_7$ is selected from the group consisting of H, —CN, —$NO_2$, $C_1$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl C—C6 alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups;

$R_8$ and $R_9$ and the nitrogen to which they are attached form a 5, 6 or 7 membered heterocycloalkyl ring, which is unsubstituted or substituted with 1, 2, or 3 groups that are independently selected from $C_1$-$C_6$ alkyl, $C_1$-$C_6$ alkoxy, hydroxy, and halogen; or $R_7$, $R_8$, and the nitrogens to which they are attached form a 5, 6, or 7 membered heterocycloalkyl group that is unsubstituted or substituted with 1, 2 or 3 groups that are independently selected from $C_1$-$C_6$ alkyl, $C_1$-$C_6$ alkoxy, hydroxy, and halogen, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; and $R_9$ is selected from the group consisting of H, $C_1$-$C_6$ alkyl, $C_1$-$C_6$ alkoxy, $C_3$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, thiomorpholinyl S-oxide, phenyl, naphthyl, thiomorpholinyl S,S-dioxide, pyrrolidinyl, pyridyl, pyridazyl, pyrimidyl, pyrazinyl, and imidazolyl, wherein each of the above is unsubstituted or substituted with 1, 2, 3, or 4 $R_6$ groups;

R4 is selected from the group consisting of H, $C_1$-$C_4$ alkyl, benzyl and phenethyl, wherein the benzyl and phenethyl groups are unsubstituted or substituted with 1, 2, 3, or 4 $R_6$ groups;

$R_5$ is -M-G-A, wherein

M is selected from the group consisting of phenyl, pyridyl, pyrimidyl, pyridazinyl, pyrazinyl, thiophenyl, and pyrrolyl, wherein M is unsubstituted or substituted with 1, 2, 3, or 4 groups that are independently selected from the group consisting of halogen, $C_1$-$C_6$ alkyl, hydroxy, $C_1$-$C_6$ alkoxy, halo $C_1$-$C_6$ alkyl, halo $C_1$-$C_6$ alkoxy, and hydroxy $C_1$-$C_6$ alkyl, G is selected from a direct bond between M and A, $CH_2$, O, S, SO, and $SO_2$;

A is selected from the group consisting of phenyl, naphthyl, pyridyl, pyrimidyl, pyridazyl, pyrazinyl, pyrrolyl, benzo[1,3]dioxyl, quinolinyl, isoquinolinyl, tetrahydroisoquinolinyl, tetrahydronaphthyl, and dihydronaphthyl, wherein each of the above is unsubstituted or substituted with 1, 2, 3, 4, or 5 groups that are independently halogen, $C_1$-$C_6$ alkyl, $C_1$-$C_6$ alkoxy, halo $C_1$-$C_6$ alkyl, halo $C_1$-$C_6$ alkoxy, CN, or $NO_2$.

In these compounds, $R_5$ can also be $R_5$ wherein $R_5$ is -M-G-A, wherein

M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, O, S, SO, and $SO_2$;

A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, —CN, and —$NO_2$.

The compound can have $R_3$, wherein $R_3$ is —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$—CS cycloalkyl $C_1$-$C_6$ alkyl, wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$, or $R_8$ and $R_9$ and the nitrogen to which they are attached form a 5 or 6 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

$R_3$ can also be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or C—C4 alkoxy groups;

Q is piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy; and J is —C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_i$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; or $R_8$ and $R_9$ and the nitrogen to which they are attached form a 5 or 6 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

These compounds can also have $R_8$ and $R_9$ and the nitrogen to which they are attached form a morpholinyl, thiomorpholinyl, piperazinyl, piperidinyl or pyrrolidinyl ring, each of which is unsubstituted or substituted with 1, 2, or 3 groups that are independently $C_1$-$C_6$ alkyl, $C_1$-$C_6$ alkoxy, hydroxy, or halogen.

R3 can also be —Z-Q-J wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$, $R_8$, and the nitrogens to which they are attached form a 5, 6, or 7 membered heterocycloalkyl group that is unsubstituted or substituted with 1, or 2 groups that are independently $C_1$-$C_6$ alkyl, $C_1$-$C_6$ alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, and imidazolyl, wherein each of the above is unsubstituted or substituted with 1, or 2 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

$R_3$ can also be —Z-Q-J wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy; and J is —C(=$NR_7$)$NROR_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$—CS cycloalkyl $C_1$-$C_6$ alkyl, wherein each of the above is unsubstituted or substituted with 1, 2, 3, or 4 $R_6$ groups; wherein $R_6$ at each occurrence is independently selected from the group consisting of halogen, hydroxy, $NO_2$, C—C6 alkyl, $C_1$-$C_6$ alkoxy, $CF_3$, and $OCF_3$.

Another compound that can be utilized in the methods of the present invention can be a compound according to the formula set forth below:

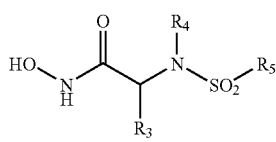

wherein $R_3$, $R_4$, and $R_5$ are as defined above. A compound with this structure can also have $R_4$, wherein $R_4$ is selected from the group consisting of H, $C_1$-$C_4$ alkyl, and benzyl wherein the benzyl group is unsubstituted or substituted with 1, 2, 3, or 4 $R_6$ groups, wherein $R_6$ at each occurrence is independently selected from the group consisting of halogen, hydroxy, —$NO_2$, $C_1$-$C_6$ alkyl, $C_1$-$C_6$ alkoxy, $CF_3$, and $OCF_3$.

$R_5$ can also be -M-G-A, wherein

M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_l$-$C_4$ alkyl, hydroxy, methoxy, ethoxy, isopropoxy, $CF_3$, $OCF_3$, halo $C_l$-$C_4$ alkyl, halo C—$C4$ alkoxy, and hydroxy $C_1$-$C_4$ alkyl;

G is selected from a direct bond between M and A, $CH_2$, O, S, SO, and $SO_2$;

A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_l$-$C_4$ alkyl, $C_1$-$C_4$ alkoxy, halo $C_1$-$C_4$ alkyl, $CF_3$, $OCF_3$, CN, and $NO_2$.

$R_3$ can also be Z-Q-J, wherein

Z is a $C_1$-$C_6$ alkyl, $C_1$-$C_6$ alkoxy $C_1$-$C_6$ alkyl, or $C_1$-$C_6$ alylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-CB cycloalkyl $C_1$-$C_6$ alkyl, phenyl $C_1$-$C_6$ alkyl, and pyridyl $C_1$-$C_6$ alkyl, pyridazyl $C_1$-$C_6$ alkkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen, wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

Another compound provided herein can be of the structural formula set forth below

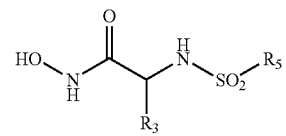

wherein:

R3 is —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$ is selected from the group consisting of H, CN, $NO_2$, $C_3$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently H, or $C_1$-$C_6$ alkyl, $R_7$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl C—$C6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, C—$C6$ alkoxy, hydroxy, or halogen; wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; and $R_5$ is -M-G-A, wherein M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, O, S, SO, and $SO_2$; and A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$.

$R_3$ can be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR_7)NR_8R_9 or —NH—C(=NR_7)NR_8R_9, wherein $R_7$ is selected from the group consisting of H, CN, $NO_2$, $C_1$-$C_6$ alkyl, $C_1$-$C_6$ alkanoyl, and —C(=O)NR_{10}R_{11}, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, piperidinyl $C_1$-$C_6$ alkyl, pyrrolidinyl $C_1$-$C_6$ alkyl, $C_3$-$C_8$ cycloalkyl, $C_3$-$C_8$ cycloalkyl $C_1$-$C_6$ alkyl, benzyl, phenethyl, and pyridyl $C_1$-$C_6$ alkyl, pyridazyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; wherein $R_6$ at each occurrence is independently selected from the group consisting of halogen, hydroxy, $NO_2$, $C_1$-$C_6$ alkyl $C_1$-$C_6$ alkoxy, $CF_3$, and $OCF_3$; and $R_5$ can be -M-G-A, wherein M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, and O; and

A is selected from the group consisting of phenyl, naphthyl, pyridyl, tetrahydronaphthyl, benzo[1,3]dioxyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$.

The compound can also have the following structure wherein

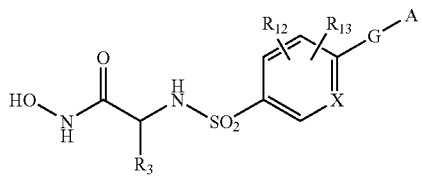

$R_3$ is defined above, and X is CH, $CR_{11}$, or N;

$R_{12}$ and $R_{13}$ are at each occurrence are independently selected from the group consisting of H, halogen, $CF_3$, $C_1$-$C_4$ alkyl, and $C_1$-$C_4$ alkoxy;

A is selected from the group consisting of phenyl, naphthyl, pyridyl, benzo[1,3]dioxyl, and tetrahydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$; and G is selected from a direct bond between M and A, $CH_2$, and O.

The compound can also have the following structure wherein

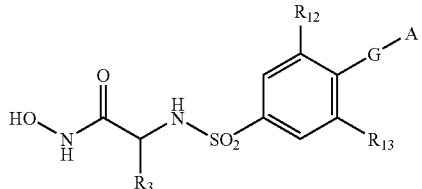

$R_3$, is as defined above,

A is phenyl, 3-fluorophenyl, 4-fluorophenyl, 4-chlorophenyl, 4-cyanophenyl, benzo[1,3]dioxyl, 3,5-dimethylphenyl, 2-naphthyl, or 2-tetrahydronaphthyl;

G is a direct bond between M and A, or G is oxygen; and $R_{12}$ and $R_{13}$ are independently H, fluoro, chloro, $CF_3$, methyl or methoxy.

The compound can also have $R_3$ wherein $R_3$ is —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_3$-$C_4$ alkyl, halogen, or C—C4 alkoxy groups;

Q is a direct bond between Z and J or —C(=O)—, J is —NH—C(=NR_7)NR_8R_9, wherein $R_7$ is selected from the group consisting of H, CN, $NO_2$, $C_1$-$C_6$ alkyl, $C_1$-$C_6$ alkanoyl, and —C(=O)NR_{10}R_{11}, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$, or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

$R_3$ can also be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(O)—, J is —NH—C(=NR$_7$)NR$_8$R$_9$, wherein $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, pyrimidyl, pyrazinyl, and imidazolyl, wherein each of the above is unsubstituted or substituted with 1, 2, 3, or 4 $R_6$ groups, wherein $R_6$ at each occurrence is independently selected from the group consisting of halogen, hydroxy, NO$_2$, $C_1$-$C_6$ alkyl, $C_1$-$C_6$ alkoxy, CF$_3$, and OCF$_3$.

R3 can also be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ wherein $R_7$ is selected from the group consisting of H, CN, NO$_2$, $C_1$-$C_6$ alkyl, $C_1$-$C_6$ alkanoyl, and —C(=O)NR$_{10}$R$_{11}$, wherein $R_{10}$ and $R_{11}$ are independently H, or $C_1$-$C_6$ alkyl, $R_7$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-CB cycloalkyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; wherein $R_6$ at each occurrence is independently selected from the group consisting of halogen, hydroxy, NO$_2$, $C_1$-$C_6$ alkyl, $C_1$-$C_6$ alkoxy, CF$_3$, and OCF$_3$.

The compound can also have the formula set forth below wherein:

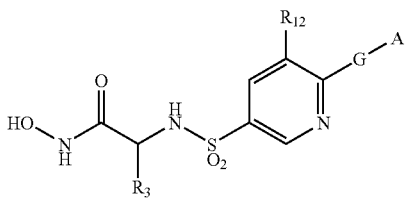

wherein
$R_3$, is as defined above,

A is phenyl, 3-fluorophenyl, 4-fluorophenyl, benzo[1,3]dioxyl, 4-chlorophenyl, 4-cyanophenyl, 3,5-dimethylphenyl, 2-naphthyl, or 2-tetrahydronaphthyl G is a direct bond between M and A, or G is oxygen;

$R_{12}$ is selected from the group consisting of H, halogen, $C_1$-$C_4$ alkyl, —CF$_3$, and $C_1$-$C_4$ alkoxy.

$R_3$ can also be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(O)—, J is —NH—C(=NR$_7$)NR$_8$R$_9$, wherein $R_7$ is selected from the group consisting of H, CN, NO$_2$, $C_1$-$C_6$ alkyl, $C_1$-$C_6$ alkanoyl, and —C(=O)NR$_{10}$R$_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; wherein $R_6$ at each occurrence is independently selected from the group consisting of halogen, hydroxy, NO$_2$, $C_1$-$C_6$ alkyl, $C_1$-$C_6$ alkoxy, CF$_3$, and OCF$_3$, or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

$R_3$ can also be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(=O)—,

J is —NH—C(=NR)NR$_8$R$_9$, wherein $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, C—C6 alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, pyrimidyl, pyrazinyl, and imidazolyl, wherein each of the above is unsubstituted or substituted with 1, 2, 3, or 4 R6 groups, wherein $R_6$ at each occurrence is independently selected from the group consisting of halogen, hydroxy, NO$_2$, $C_1$-$C_6$ alkyl, $C_1$-$C_6$ alkoxy, CF$_3$, and OCF$_3$.

$R_3$ can also be —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ wherein $R_7$ is selected from the group consisting of H, CN, NO$_2$, $C_1$-$C_6$ alkyl, $C_1$-$C_6$ alkanoyl, and —C(=O)NR$_{10}$R$_{11}$, wherein $R_{10}$ and $R_{11}$ are independently H, or $C_1$-$C_6$ alkyl, R7 and R9 are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; or R8 and R9 and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

The compound can also have the structural formula set forth below wherein:

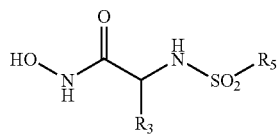

R3 is —Z-Q-J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein $R_5$ is -M-G-A, wherein M is phenyl, pyridyl, pyrimidyl, pyridazinyl, pyrazinyl, thiophenyl, and pyrrolyl, each of which is substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, and 0; and

A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$. $OCF_3$, CN, and $NO_2$.

The compound can also have the formula set forth below:

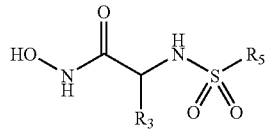

wherein R3 is selected from:

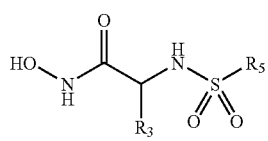 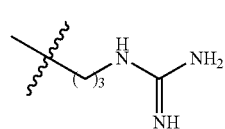

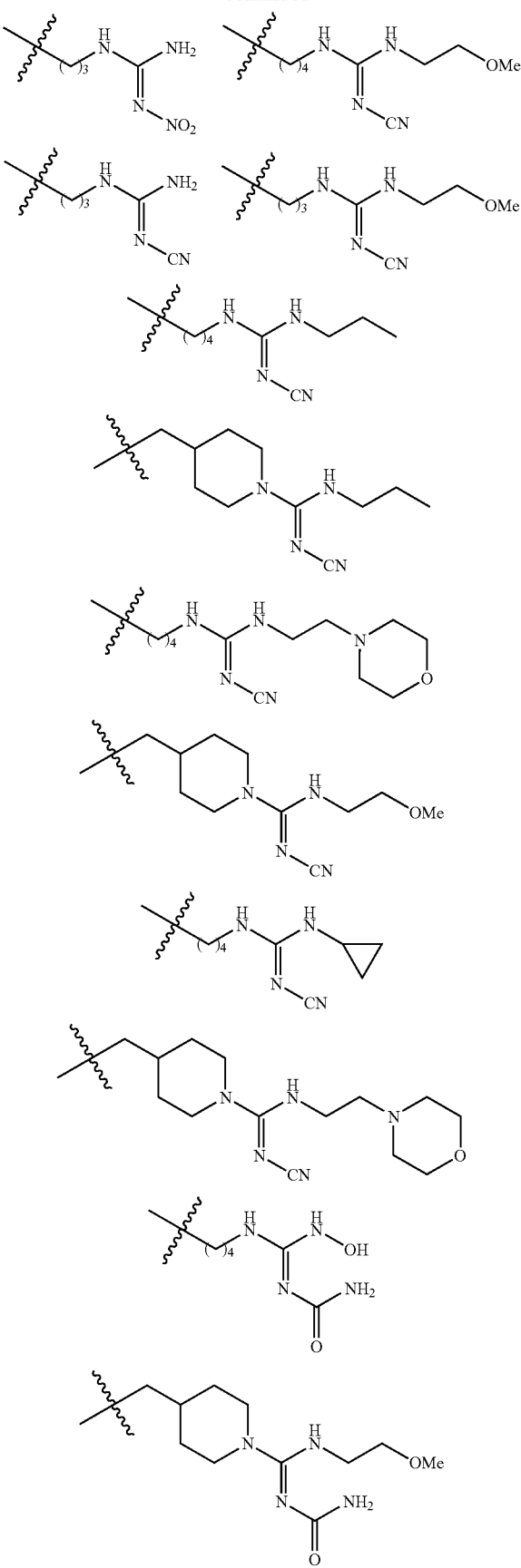

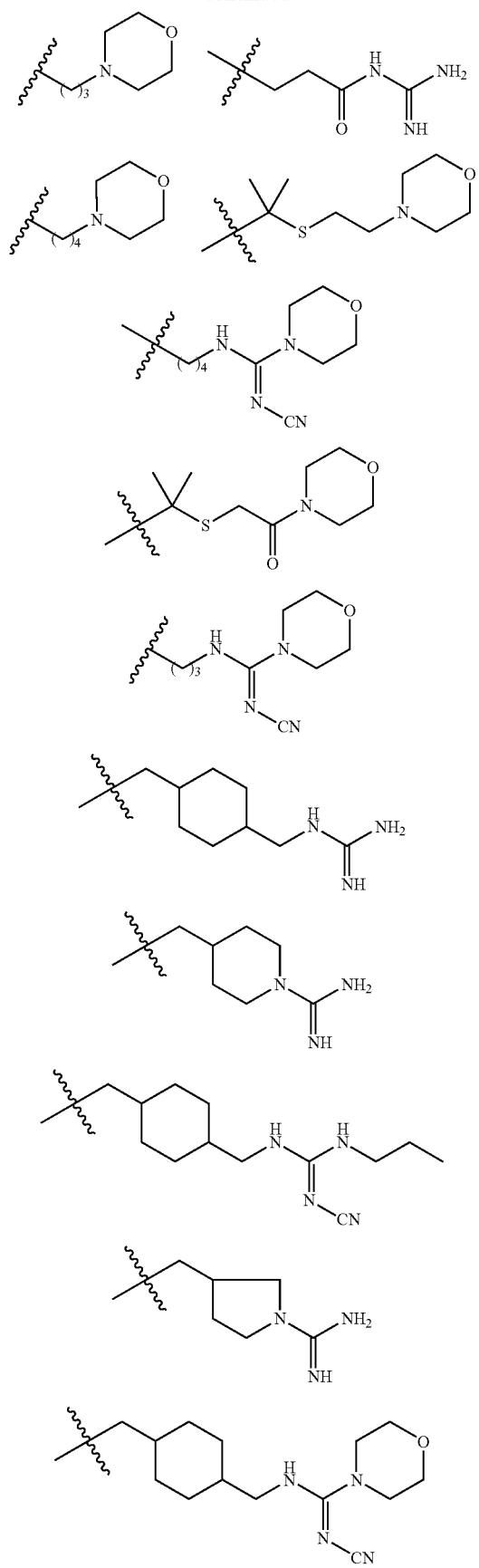
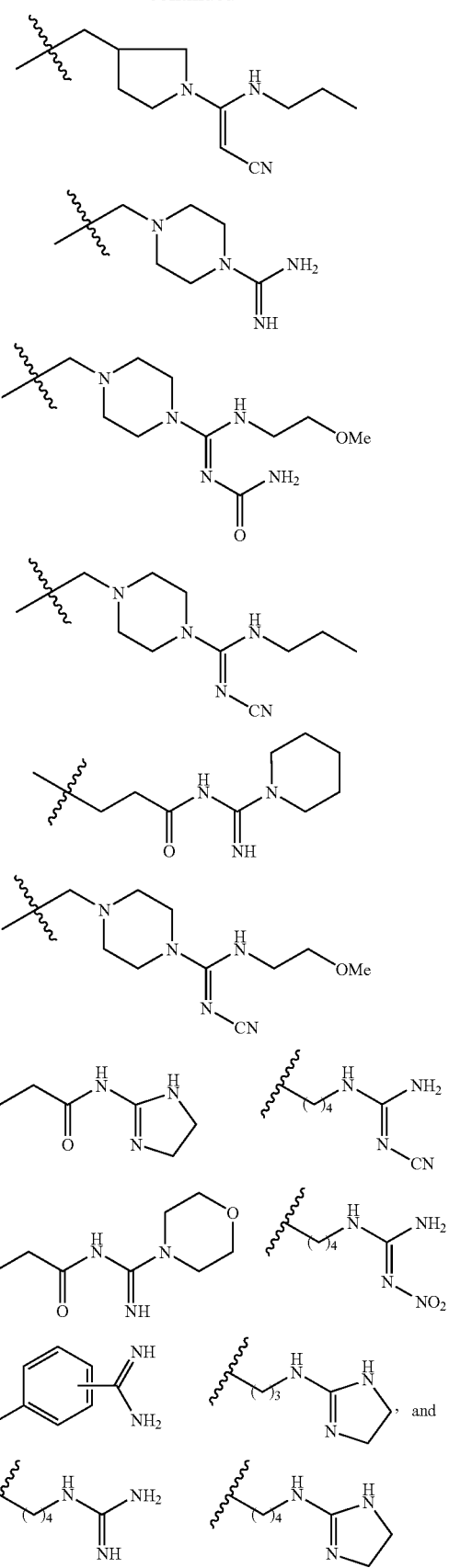

and R5 is selected from:
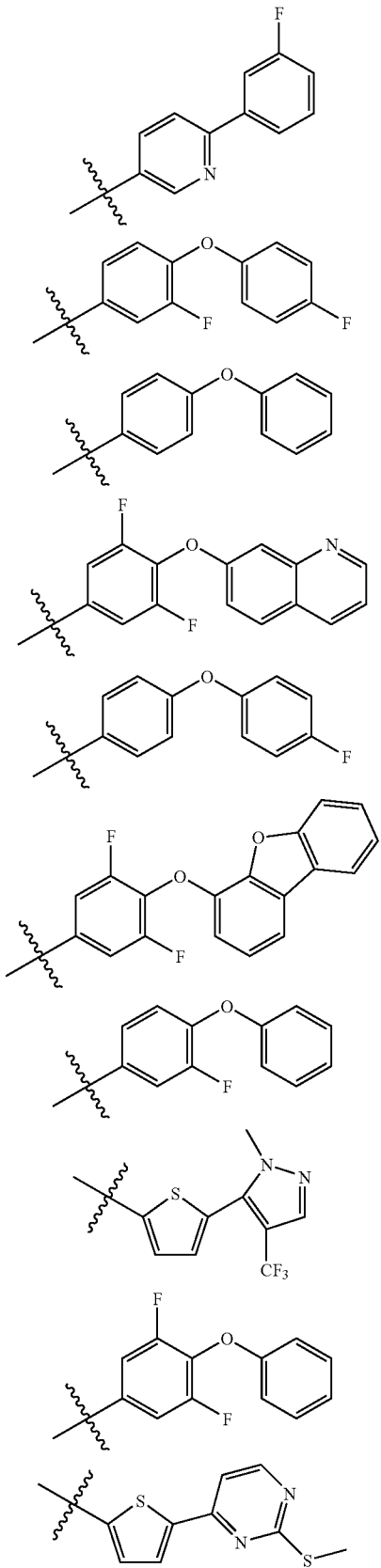
-continued
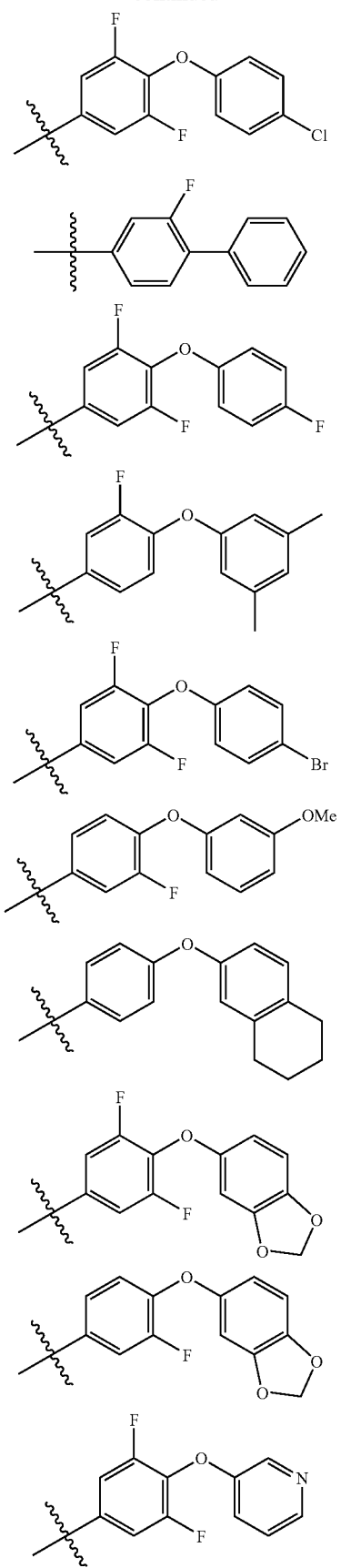

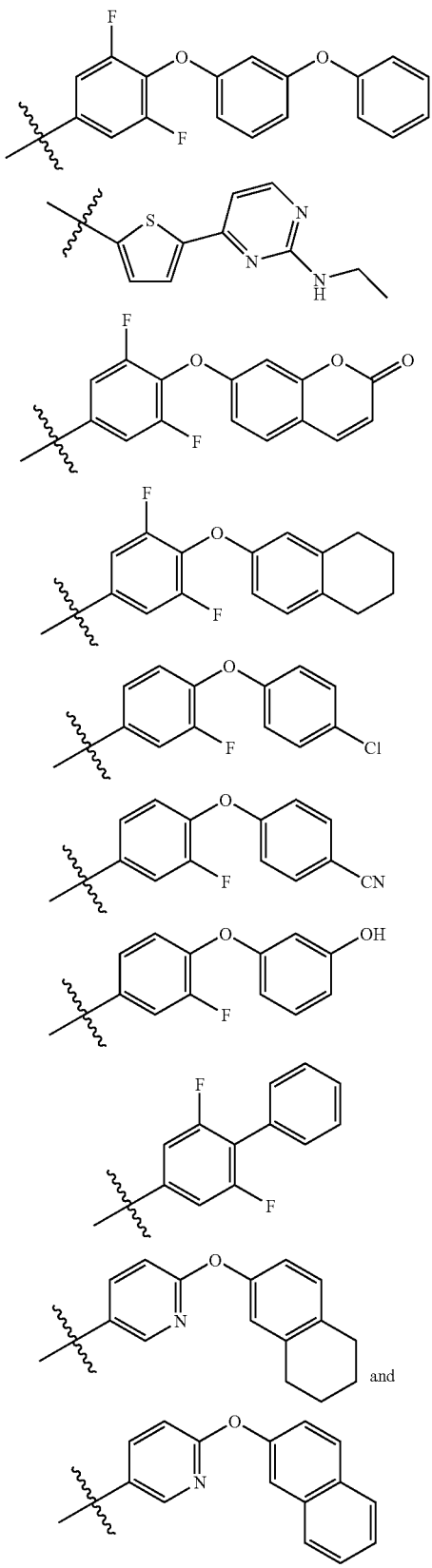

The compound can also be any compound or pharmaceutically acceptable salt listed in the following table:

| | |
|---|---|
| 1 | $N^2$-{[6-(3-fluorophenyl)pyridin-3-yl]sulfonyl}-$N^1$-hydroxy-D-argininamide |
| 2 | $N^1$-hydroxy-$N^2$-[(4-phenoxyphenyl)sulfonyl]-D-argininamide |
| 3 | $N^2$-{[4-(4-fluorophenoxy)phenyl]sulfonyl}-$N^1$-hydroxy-D-argininamide |
| 4 | $N^2$-[(3-fluoro-4-phenoxyphenyl)sulfonyl]-$N^1$-hydroxy-D-argininamide |
| 5 | $N^2$-[(3,5-difluoro-4-phenoxyphenyl)sulfonyl]-$N^1$-hydroxy-D-argininamide |
| 6 | $N^2$-{[4-(4-chlorophenoxy)-3,5-difluorophenyl]sulfonyl}-$N^1$-hydroxy-D-argininamide |
| 7 | $N^2$-{[3,5-difluoro-4-(4-fluorophenoxy)phenyl]sulfonyl}-$N^1$-hydroxy-D-argininamide |
| 8 | $N^2$-{[4-(4-bromophenoxy)-3,5-difluorophenyl]sulfonyl}-$N^1$-hydroxy-D-argininamide |
| 9 | $N^2$-{[3-fluoro-4-(4-fluorophenoxy)phenyl]sulfonyl}-$N^1$-hydroxy-D-argininamide |
| 10 | $N^2$-{[4-(4-chlorophenoxy)-3-fluorophenyl]sulfonyl}-$N^1$-hydroxy-D-argininamide |
| 11 | $N^2$-{[4-(4-cyanophenoxy)-3-fluorophenyl]sulfonyl}-$N^1$-hydroxy-D-argininamide |
| 12 | $N^2$-{[4-(3,5-dimethylphenoxy)-3-fluorophenyl]sulfonyl}-$N^1$-hydroxy-D-argininamide |
| 13 | $N^1$-hydroxy-$N^2$-{[4-(phenyloxy)phenyl]sulfonyl}-D-lysinamide |
| 14 | $N^1$-hydroxy-$N^2$-{[6-(5,6,7,8-tetrahydronaphthalen-2-yloxy)pyridin-3-yl]sulfonyl}-D-argininamide |
| 15 | $N^5$-[(Z)-amino(nitroimino)methyl]-$N^2$-{[6-(3-fluorophenyl)pyridin-3-yl]sulfonyl}-$N^1$-hydroxy-D-ornithinamide |
| 16 | $N^3$-[(Z)-amino(nitroimino)methyl]-$N^1$-hydroxy-$N^2$-[(4-phenoxyphenyl)sulfonyl]-D-ornithinamide |
| 17 | $N^6$-[(E)-amino(cyanoimino)methyl]-$N^2$-{[6-(3-fluorophenyl)pyridin-3-yl]sulfonyl}-$N^3$-hydroxy-D-lysinamide |
| 18 | $N^6$-[(E)-amino(cyanoimino)methyl]-$N^1$-hydroxy-$N^2$-[(4-phenoxyphenyl)sulfonyl]-D-lysinamide |
| 19 | $N^6$-{(E)-(cyanoimino)[(2-methoxyethyl)amino]methyl}-$N^2$-{[6-(3-fluorophenyl)pyridin-3-yl]sulfonyl}-$N^2$-hydroxy-D-lysinamide |
| 20 | $N^6$-{(Z)-(cyanoimino)[(2-methoxyethyl)amino]methyl}-$N^1$-hydroxy-$N^2$-[(4-phenoxyphenyl) sulfonyl]-D-lysinamide |
| 21 | $N^6$-{(Z)-(cyanoimino)[(2-methoxyethyl)amino]methyl}-$N^2$-{[4-(4-fluorophenoxy)phenyl]sulfonyl}-$N^1$-hydroxy-D-lysinamide |
| 22 | $N^6$-[(E)-(cyanoimino)(propylamino)methyl]-$N^2$-{[6-(3-fluorophenyl)pyridin-3-yl]sulfonyl}-$N^1$-hydroxy-D-lysinamide |
| 23 | $N^6$-[(E)-(cyanoimino)(propylamino)methyl]-$N^2$-hydroxy-$N^2$-[(4-phenoxyphenyl)sulfonyl]-D-lysinamide |
| 24 | $N^6$-[(E)-(cyanoimino)(propylamino)methyl]-$N^2$-{[4-(4-fluorophenoxy)phenyl]sulfonyl}-$N^2$-hydroxy-D-lysinamide |
| 25 | $N^6$-{(Z)-(cyanoimino)[(2-morpholin-4-ylethyl)amino]methyl}-$N^2$-{[6-(3-fluorophenyl)pyridin-3-yl]sulfonyl}-$N^1$-hydroxy-D-lysinamide |
| 26 | $N^6$-{(Z)-(cyanoimino)[(2-morpholin-4-ylethyl)amino]methyl}-$N^2$-hydroxy-$N^2$-[(4-phenoxyphenyl) sulfonyl]-D-lysinamide |
| 27 | $N^6$-[(Z)-(cyanoimino)(cyclopropylamino)methyl]-$N^1$-hydroxy-$N^2$-[(4-phenoxyphenyl) sulfonyl]-D-lysinamide |
| 28 | $N^6$-[(E)-[(aminocarbonyl)imino](hydroxyamino)methyl]-$N^2$-{[4-(4-fluorophenoxy)phenyl]sulfonyl}-$N^1$-hydroxy-D-lysinamide |
| 29 | $N^1$-hydroxy-5-morpholin-4-yl-$N^2$-[(4-phenoxyphenyl)sulfonyl]-D-norvalinamide |
| 30 | $N^2$-{[4-(4-fluorophenoxy)phenyl]sulfonyl}-$N^1$-hydroxy-5-morpholin-4-yl-D-norvalinamide |
| 31 | $N^2$-{[6-(3-fluorophenyl)pyridin-3-yl]sulfonyl}-$N^1$-hydroxy-6-morpholin-4-yl-D-norleucinamide |
| 32 | $N^1$-hydroxy-6-morpholin-4-yl-$N^2$-[(4-phenoxyphenyl)sulfonyl]-D-norleucinamide |
| 33 | $N^2$-{[4-(4-fluorophenoxy)phenyl]sulfonyl}-$N^1$-hydroxy-6-morpholin-4-yl-D-norleucinamide |
| 34 | $N^2$-[(3-fluoro-4-phenoxyphenyl)sulfonyl]-$N^1$-hydroxy-6-morpholin-4-yl-D-norleucinamide |
| 35 | $N^2$-{[4-(4-chlorophenoxy)-3,5-difluorophenyl]sulfonyl}-$N^1$-hydroxy-6-morpholin-4-yl-D-norleucinamide |
| 36 | $N^2$-{[3,5-difluoro-4-(4-fluorophenoxy)phenyl]sulfonyl}-$N^1$-hydroxy-6-morpholin-4-yl-D-norleucinamide |
| 37 | $N^6$-[(E)-(cyanoimino)(morpholin-4-yl)methyl]-$N^2$-{[4-(4-fluorophenoxy)phenyl]sulfonyl}-$N^2$-hydroxy-D-lysinamide |
| 38 | $N^6$-[(Z)-(cyanoimino)(morpholin-4-yl)methyl]-$N^2$-{[3-fluoro-4-(4-fluorophenoxy)phenyl]sulfonyl}-$N^1$-hydroxy-D-lysinamide |
| 39 | 3-{3-[amino(imino)methyl]piperidin-4-yl}-$N^1$-hydroxy-$N^2$-[(4-phenoxyphenyl)sulfonyl]alaninamide |
| 40 | 3-{3-[(Z)-(cyanoimino)(propylamino)methyl]piperidin-4-yl}-$N^1$-hydroxy-$N^2$-[(4-phenoxyphenyl)sulfonyl]alaninamide |

| | |
|---|---|
| 41 | 3-(1-{(Z)-(cyanoimino)[(2-methoxyethyl)amino]methyl}piperidin-4-yl)-$N^2$-hydroxy-$N^2$-[(4-phenoxyphenyl)sulfonyl]alaninamide |
| 42 | 3-(1-{(E)-(cyanoimino)[(2-methoxyethyl)amino]methyl}piperidin-4-yl)-$N^2$-{[3,5-difluoro-4-(4-fluorophenoxy)phenyl]sulfonyl}-$N^1$-hydroxyalaninamide |
| 43 | 3-(1-{(Z)-[(aminocarbonyl)imino][(2-methoxyethyl)amino]methyl}piperidin-4-yl)-$N^1$-hydroxy-$N^2$-[(4-phenoxyphenyl)sulfonyl]alaninamide |
| 44 | $N^2$-{[3,5-difluoro-4-(4-fluorophenoxy)phenyl]sulfonyl}-$N^3$-hydroxy-3-[(2-morpholin-4-ylethyl)thio]-D-valinamide |
| 45 | $N^2$-{[3-fluoro-4-(4-fluorophenoxy)phenyl]sulfonyl}-$N^3$-hydroxy-3-[(2-morpholin-4-ylethyl)thio]-D-valinamide |
| 46 | $N^2$-{[3-fluoro-4-(4-fluorophenoxy)phenyl]sulfonyl}-$N^3$-hydroxy-3-[(2-morpholin-4-yl-2-oxoethyl)thio]-D-valinamide |
| 47 | $N^2$-{[4-(4-chlorophenoxy)-3-fluorophenyl]sulfonyl}-$N^1$-hydroxy-3-[(2-morpholin-4-yl-2-oxoethyl)thio]-D-valinamide |
| 48 | $N^6$-4,5-dihydro-1H-imidazol-2-yl-$N^2$-{[4-(4-fluorophenoxy)phenyl]sulfonyl}-$N^3$-hydroxy-D-lysinamide |
| 49 | $N^6$-[(Z)-(cyanoimino)(cyclopropylamino)methyl]-$N^2$-{[6-(3-fluorophenyl)pyridin-3-yl]sulfonyl}-$N^1$-hydroxy-D-lysinamide |
| 50 | $N^1$-hydroxy-$N^2$-{[4-(phenyloxy)phenyl]sulfonyl}-3-piperidin-3-ylalaninamide |
| 51 | $N^1$-hydroxy-$N^2$-{[4-(phenyloxy)phenyl]sulfonyl}-3-pyrrolidin-3-ylalaninamide |
| 52 | $N^2$-{[6-(3-fluorophenyl)pyridin-3-yl]sulfonyl}-$N^1$-hydroxy-D-lysinamide |
| 53 | $N^1$-hydroxy-$N^2$-{[4-(phenyloxy)phenyl]sulfonyl}-D-tryptophanamide |
| 54 | $N^1$-hydroxy-$N^2$-({5-[2-(methylthio)pyrimidin-4-yl]-2-thienyl}sulfonyl)lysinamide |
| 55 | $N^1$-hydroxy-$N^2$-{[4-(phenyloxy)phenyl]sulfonyl}-D-bimidinamide |
| 56 | $N^1$-hydroxy-$N^2$-methyl-$N^2$-{[4-(phenyloxy)phenyl]sulfonyl}-3-piperidin-3-ylalaninamide |
| 57 | $N^1$-hydroxy-$N^2$-{[4-(phenyloxy)phenyl]sulfonyl}-3-piperidin-4-ylalaninamide |
| 58 | $N^1$-hydroxy-$N^2$-{[4-(phenyloxy)phenyl]sulfonyl}-3-pyridin-3-yl-D-alaninamide |
| 59 | $N^6$-glycyl-$N^1$-hydroxy-$N^2$-{[4-(phenyloxy)phenyl]sulfonyl}-D-lysinamide |
| 60 | $N^1$-hydroxy-$N^2,N^6,N^6$-trimethyl-$N^2$-{[4-(phenyloxy)phenyl]sulfonyl}-D-lysinamide |
| 61 | 3-[4-(aminomethyl)cyclohexyl]-$N^1$-hydroxy-$N^2$-{[4-(phenyloxy)phenyl]sulfonyl}alaninamide |
| 62 | $N^1$-hydroxy-$N^2$-{[6-(naphthalen-1-yloxy)pyridin-3-yl]sulfonyl}-D-argininamide |
| 63 | $N^1$-hydroxy-$N^2$-{[6-(5,6,7,8-tetrahydronaphthalen-2-yloxy)pyridin-3-yl]sulfonyl}-D-lysinamide |
| 64 | $N^6$-[(E)-(cyanoimino)(hydroxyamino)methyl)]-$N^2$-({4-[(4-fluorophenyl)oxy]phenyl}sulfonyl)-$N^1$-hydroxy-D-lysinamide |
| 65 | $N^2$-({4-[(4-fluorophenyl)oxy]phenyl}sulfonyl)-$N^1$-hydroxy-D-lysinamide |
| 66 | $N^6$-{(Z)-(cyanoimino)[(2-morpholin-4-ylethyl)amino]methyl}-$N^2$-{[6-(3-fluorophenyl)phyridin-3-yl]sulfonyl}-$N^1$-hydroxy-D-lysinamide |
| 67 | $N^2$-({6-[(4-fluorophenyl)oxy]pyridin-3-yl}sulfonyl)-$N^1$-hydroxy-D-argininamide |
| 68 | $N^2$-({6-[(4-chlorophenyl)oxy]pyridin-3-yl}sulfonyl)-$N^1$-hydroxy-D-argininamide |
| 69 | $N^2$-({3,5-difluoro-4-[(4-fluorophenyl)oxy]phenyl}sulfonyl)-$N^1$-hydroxy-$N^6$-(morpholin-4-ylcarbonyl)-D-lysinamide |
| 70 | 4-cyano-$N^1$-hydroxy-$N^2$-{[4-(phenyloxy)phenyl]sulfonyl}-D-phenylalaninamide |
| 71 | 4-cyano-$N^2$-({3,5-difluoro-4-[(4-fluorophenyl)oxy]phenyl}sulfonyl)-$N^1$-hydroxy-D-phenylalaninamide |
| 72 | 3-cyano-$N^2$-({3,5-difluoro-4-[(4-fluorophenyl)oxy]phenyl}sulfonyl)-$N^1$-hydroxy-D-phenylalaninamide |
| 73 | 3-cyano-$N^1$-hydroxy-$N^2$-{[4-(phenyloxy)phenyl]sulfonyl}-D-phenylalaninamide |
| 74 | $N^2$-({3,5-difluoro-4-[(4-hydroxyphenyl)oxy]phenyl}sulfonyl)-$N^1$-hydroxyargininamide |
| 75 | $N^2$-{[3,5-difluoro-4-(pyridin-3-yloxy)phenyl]sulfonyl}-$N^1$-hydroxyargininamide |
| 76 | $N^2$-({3,5-difluoro-4-[(4-fluorophenyl)oxy]phenyl}sulfonyl)-$N^1$-hydroxy-$N^6$-({[2-(methyloxy)ethyl]amino}carbonyl)-D-lysinamide |
| 77 | $N^2$-({3,5-difluoro-4-[(4-fluorophenyl)oxy]phenyl}sulfonyl)-$N^6$-[1-(4,4-dimethyl-2,6-dioxocyclohexylidene)ethyl]-$N^1$-hydroxy-D-lysinamide |
| 78 | $N^2$-{(3,5-difluoro-4-[{4-[(phenylmethyl)oxy]phenyl}oxy)phenyl]sulfonyl}-$N^1$-hydroxyargininamide |
| 79 | $N^2$-{[3,5-difluoro-4-(pyridin-3-yloxy)phenyl]sulfonyl}-$N^1$-hydroxy-6-morpholin-4-yl-D-norleucinamide |
| 80 | $N^2$-({3-fluoro-4-[(4-fluorophenyl)oxy]phenyl}sulfonyl)-$N^1$-hydroxy-3-morpholin-4-yl-D-alaninamide |
| 81 | $N^2$-({4-[(4-fluorophenyl)oxy]phenyl}sulfonyl)-$N^1$-hydroxy-4-[(hydroxyamino)(imino)methyl]-D-phenylalaninamide |
| 82 | $N^2$-({3,5-difluoro-4-[(4-fluorophenyl)oxy]phenyl}sulfonyl)-$N^1$-hydroxy-3-[(hydroxyamino)(imino)methyl]-D-phenylalaninamide |
| 83 | $N^2$-({4-[(4-chlorophenyl)oxy]-3,5-difluorophenyl}sulfonyl)-$N^2$-hydroxy-3-[1-(morpholin-4-ylcarbonyl)piperidin-4-yl]alaninamide |
| 84 | $N^2$-({3,5-difluoro-4-[(4-fluorophenyl)oxy]phenyl}sulfonyl)-$N^1$-hydroxy-3-[1-(morpholin-4-ylcarbonyl)piperidin-4-yl]alaninamide |
| 85 | 3-[amino(imino)methyl]-$N^2$-({3,5-difluoro-4-[(4-fluorophenyl)oxy]phenyl}sulfonyl)-$N^1$-hydroxy-D-phenylalaninamide |
| 86 | 4-[amino(imino)methyl]-$N^2$-({3,5-difluoro-4-[(4-fluorophenyl)oxy]phenyl}sulfonyl)-$N^1$-hydroxy-D-phenylalaninamide |
| 87 | $N^5$-(aminocarbonyl)-$N^2$-({3-fluoro-4-[(4-fluorophenyl)oxy]phenyl}sulfonyl)-$N^1$-hydroxy-D-ornithinamide |
| 88 | (2R)-$N^2$-[({4-[(4-chlorophenyl)oxy]-3,5-difluorophenyl}sulfonyl)amino]-4-(dimethylamino)-$N^1$-hydroxybutanamide |
| 89 | (2R)-$N^2$-[({4-[(4-chlorophenyl)oxy]-3,5-difluorophenyl}sulfonyl)amino]-4-{[1-(4,4-dimethyl-2,6-dioxocyclohexylidene)-2-methylbutyl]amino}-$N^1$-hydroxybutanamide |
| 90 | $N^2$-({4-[(4-chlorophenyl)oxy]-3,5-difluorophenyl}sulfonyl)-$N^1$-hydroxy-3-[(2-morpholin-4-yl-2-oxoethyl)thio]-D-valinamide |
| 91 | (2R)-4-amino-$N^2$-[({4-[(4-chlorophenyl)oxy]-3,5-difluorophenyl}sulfonyl)amino]-$N^1$-hydroxybutanamide |
| 92 | (2R)-4-{[amino(imino)methyl]amino}-$N^2$-[({4-[(4-chlorophenyl)oxy]-3,5-difluorophenyl}sulfonyl)amino]-$N^2$-hydroxybutanamide |
| 93 | $N^2$-[({4-[(4-chlorophenyl)oxy]-3,5-difluorophenyl}sulfonyl)amino]-$N^1$-hydroxy-2-piperidin-4-ylacetamide |
| 94 | $N^2$-[({4-[(4-chlorophenyl)oxy]-3-fluorophenyl}sulfonyl)amino]-$N^1$-hydroxy-2-piperidin-4-ylacetamide |
| 95 | $N^2$-[({3-fluoro-4-[(4-fluorophenyl)oxy]phenyl}sulfonyl)amino]-$N^1$-hydroxy-2-piperidin-4-ylacetamide |
| 96 | $N^2$-[({4-[(4-fluorophenyl)oxy]phenyl}sulfonyl)amino]-$N^1$-hydroxy-2-piperidin-4-ylacetamide |
| 97 | $N^2$-({[6-(3-fluorophenyl)pyridin-3-yl]sulfonyl}amino)-$N^1$-hydroxy-2-piperidin-4-ylacetamide |
| 98 | $N^2$-[({4-[(3,5-dimethylphenyl)oxy]-3,5-difluorophenyl}sulfonyl)amino]-$N^1$-hydroxy-2-piperidin-4-ylacetamide |
| 99 | 3-[4-(aminomethyl)cyclohexyl]-$N^2$-({4-[(4-chlorophenyl)oxy]-3,5-difluorophenyl}sulfonyl)-$N^1$-hydroxyalaninamide |
| 100 | 3-[4-(aminomethyl)cyclohexyl]-$N^2$-({3,5-difluoro-4-[(4-fluorophenyl)oxy]phenyl}sulfonyl)-$N^1$-hydroxyalaninamide |
| 101 | 3-[4-(aminomethyl)cyclohexyl]-$N^2$-({4-[(4-chlorophenyl)oxy]-3-fluorophenyl}sulfonyl)-$N^1$-hydroxyalaninamide |
| 102 | 3-[4-(aminomethyl)cyclohexyl]-$N^2$-({3-fluoro-4-[(4-fluorophenyl)oxy]phenyl}sulfonyl)-$N^1$-hydroxyalaninamide |
| 103 | 3-[4-(aminomethyl)cyclohexyl]-$N^2$-({4-[(4-fluorophenyl)oxy]phenyl}sulfonyl)-$N^1$-hydroxyalaninamide |
| 104 | 3-[4-(aminomethyl)cyclohexyl]-$N^2$-{[6-(3-fluorophenyl)pyridin-3-yl]sulfonyl}-$N^1$-hydroxyalaninamide, and |
| 105 | 3-[4-(aminomethyl)cyclohexyl]-$N^2$-({4-[(3,5-dimethylphenyl)oxy]-3,5-difluorophenyl}sulfonyl)-$N^1$-hydroxyalaninamide. |

A composition of the present invention can also comprise a compound of the structural formula

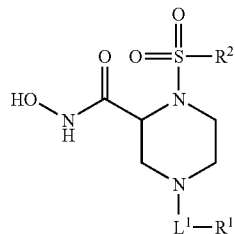

and pharmaceutically acceptable salts, esters, amides, and prodrugs thereof wherein L1 is —C(O)—, —S(O)$_2$—, or —(CH$_2$)$_n$—;

R$_1$ is H, OR$^{11}$, (CH2)$_n$R$^{11}$—C(O)R$^{11}$, or NR$^{12}$R$^{13}$;

R$^{11}$, R$^{12}$ and R$^{13}$ independently are

R$^{50}$;

saturated or mono- or poly-unsaturated C$_5$-C$_{14}$-mono- or fused poly-cyclic hydrocarbyl, optionally containing one or two annular heteroatoms per ring and optionally substituted with one or two R$^{50}$ substituents;

C$_1$-C$_6$ alkyl, C$_2$-C$_6$-alkenyl, C$_2$-C$_6$-alkynyl, or C(O)H, each of which is optionally substituted with one, two or three substituents independently selected from R$^{50}$ and saturated or mono- or poly-unsaturated C$_5$-C$_{14}$-mono- or fused poly-cyclic hydrocarbyl, optionally containing one or two annular heteroatoms per ring and optionally substituted with one, two or three R$^{50}$ substituents;

or R$^{12}$ and R$^{13}$ together with the N to which they are covalently bound, a C$_5$-C$_6$ heterocycle optionally containing a second annular heteroatom and optionally substituted with one or two R$^{50}$ substituents;

R$_2$ is —R$^{21}$-L$^2$R$^{22}$;

R$^{21}$ is saturated or mono- or poly-unsaturated C$_5$-C$_{14}$-mono- or fused poly-cyclic hydrocarbyl, optionally containing one or two annular heteroatoms per ring and optionally substituted with one, two, or three R$^{50}$ substituents;

L$^2$ is —O—, —C(O)—, —CH2-, —NH—, —S(0$_2$)- or a direct bond;

R$^{22}$ is saturated or mono- or poly-unsaturated C$_5$-C$_{14}$-mono- or fused poly-cyclic hydrocarbyl, optionally containing one or two annular heteroatoms per ring and optionally substituted with one, two, or three R$^{50}$ substituents; and R$^{50}$ is R$^{51}$-L$^3$-(CH$_2$)$_n$;

L3 is —O—, —NH—, —S(O)$_{02}$—, —C(O)—, C(O)O, C(O)NH, —OC(O)—, —NHC(O)—, C$_6$H$_4$, or a direct bond;

R$^{51}$ is H, C$_1$-C$_6$-alkyl, C$_2$-C$_6$-alkenyl, C$_2$-C$_6$-alkynyl, halo, CF$_3$, OCF$_3$, OH, NH$_2$, mono-C$_1$-C$_6$alkyl amino, di-C$_1$-C$_6$alkyl amino, SH, CO$_2$H, CN, NO$_2$, SO$_3$H, or a saturated or mono- or poly-unsaturated C$_5$-C$_{14}$-mono- or fused poly-cyclic hydrocarbyl, optionally containing one or two annular heteroatoms per ring and optionally substituted with one, two, or three substituents;

wherein n is 0, 1, 2, or 3;

provided that an O or S is not singly bonded to another O or S in a chain of atoms.

Also provided is a compound as set forth above wherein L$^1$ is —C(O)— or —S(O)$_2$—.

Also provided is a compound as set forth above wherein L$^1$ is —C(O— and R$^1$ is OR$^{11}$ or (CH$_2$)$_n$R$^{11}$, OC$_1$-C$_6$alkyl-mono-C$_1$-C$_6$alkyl amino, —OC, —C$_6$alkyl-di-C$_1$-C$_6$alkyl amino, —OC, 6alkyl-N-heterocyclyl, —C$_1$-C$_6$alkyl-mono-C$_1$-C$_6$alkyl amino, —C$_1$-C$_6$alkyl-di-C$_1$-C$_6$alkyl amino, or C$_1$-C$_6$alkyl-N-heterocyclyl.

R$^1$ can also be C$_1$-C$_6$ alkoxy-C$_1$-C$_6$-alkoxy.

R$^1$ can also be methoxyethoxy.

The compound wherein L$^1$ is —S(O)$_2$—, and R$^1$ is —NR$^{12}$R$^{13}$—(CH2)$_n$R$^{11}$, C$_1$-C$_6$alkyl-mono-C$_1$-C$_6$alkyl amino, C$_1$-C$_6$alkyl-di-C$_1$-C$_6$alkyl amino, or C$_1$-C$_6$alkylN-heterocyclyl.

Also provided is a compound as set forth above wherein L2 is —O—.

Further provided is a compound with the structure as set forth above, wherein R$^2$ is phenoxyphenyl wherein each phenyl is optionally substituted with one or two R$^{50}$ substituents. In a more specific example, the R$^{50}$ substituents are halo.

Also provided is a compound wherein the saturated or mono- or poly-unsaturated C$_5$-C$_{14}$-mono- or fused poly-cyclic hydrocarbyl containing one or two annular heteroatoms per ring is selected from the group consisting of morpholinyl, piperazinyl, homopiperazinyl, pyrrolidinyl, piperidinyl, homopiperidinyl, furyl, thienyl, pyranyl, isobenzofuranyl, chromenyl, pyrrolyl, imidazolyl, isoxazolyl, pyridyl, pyrazinyl, pyrimidinyl, oxadiazolyl, indolyl, quinolinyl, carbazolyl, acrydinyl, and furazanyl, optionally substituted with one or two R$^{50}$ substituents.

Further provided is a compound wherein R12 and R$^{13}$, together with the N to which they are covalently bound, form a heterocycle selected from the group consisting of morpholinyl, piperazinyl, homopiperazinyl, pyrrolidinyl, piperidinyl, homopiperidinyl, pyrrolyl, imidazolyl, isoxazolyl, pyridyl, pyrazinyl, pyrimidinyl, oxadiazolyl, indolyl, quinolinyl, carbazolyl, acrydinyl, and furazanyl, optionally substituted with one or two R$^{50}$ substituents.

Also provided is a compound as described above comprising the absolute stereochemistry of structural formula:

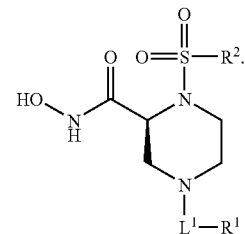

Further provided is a compound a described above comprising the absolute stereochemistry of structural formula:

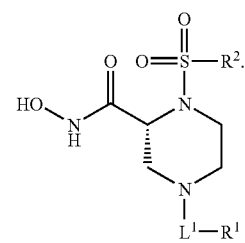

Also provided herein are compounds with the formulas set forth above, wherein L$^1$-R$^1$ is selected from:

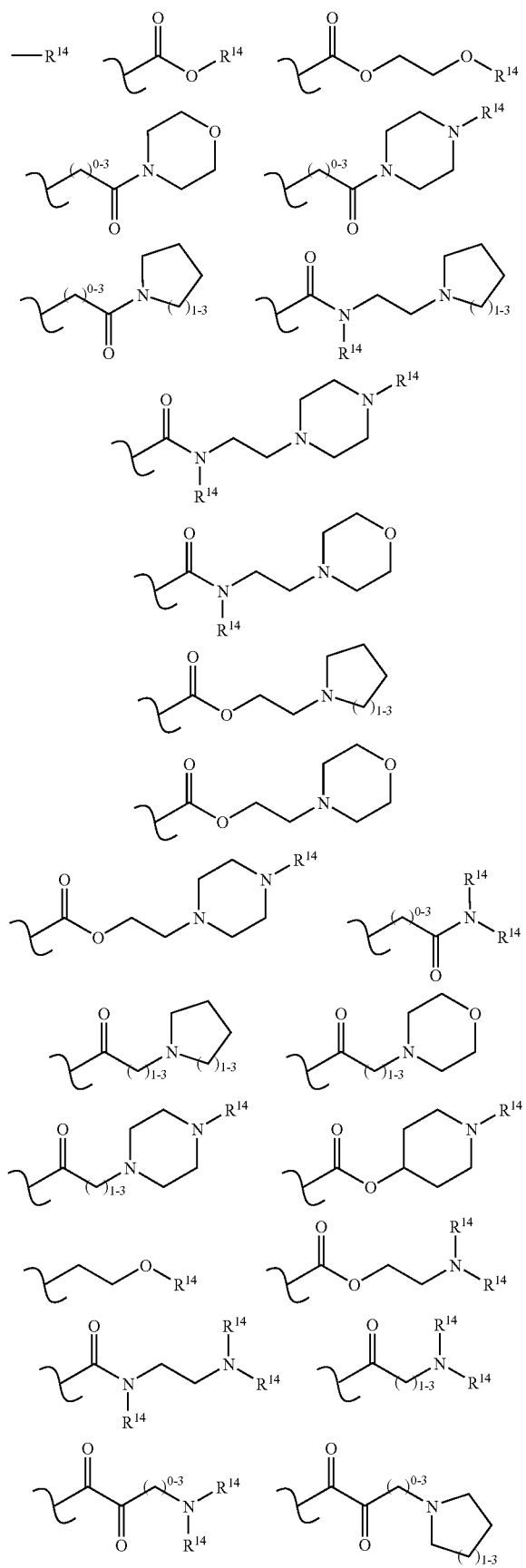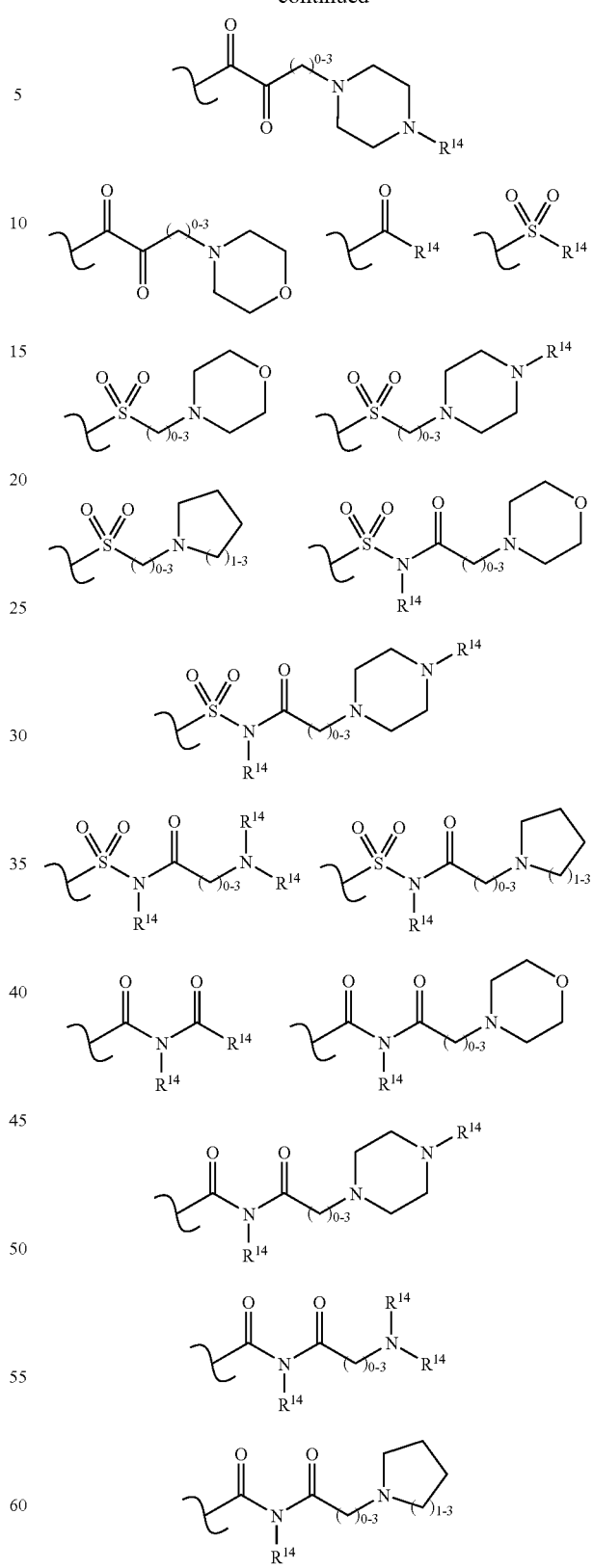
wherein each $R^{14}$ is independently selected from H, $(CH_2)_{1-3}$, $CO_2H$, alkyl, alkoxy, alkenyl, aryl, heteroaryl, arylalkyl, and heteroarylalkyl; and $R^2$ is selected from:
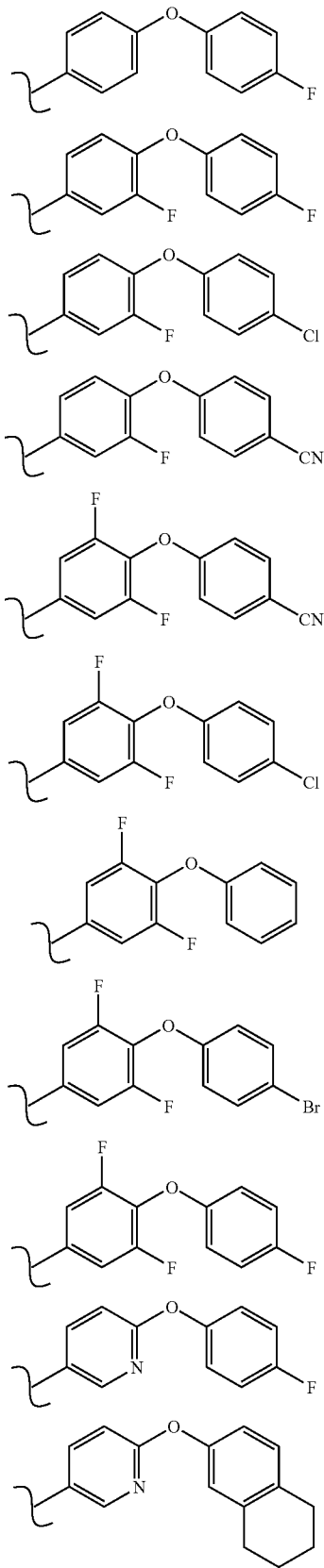
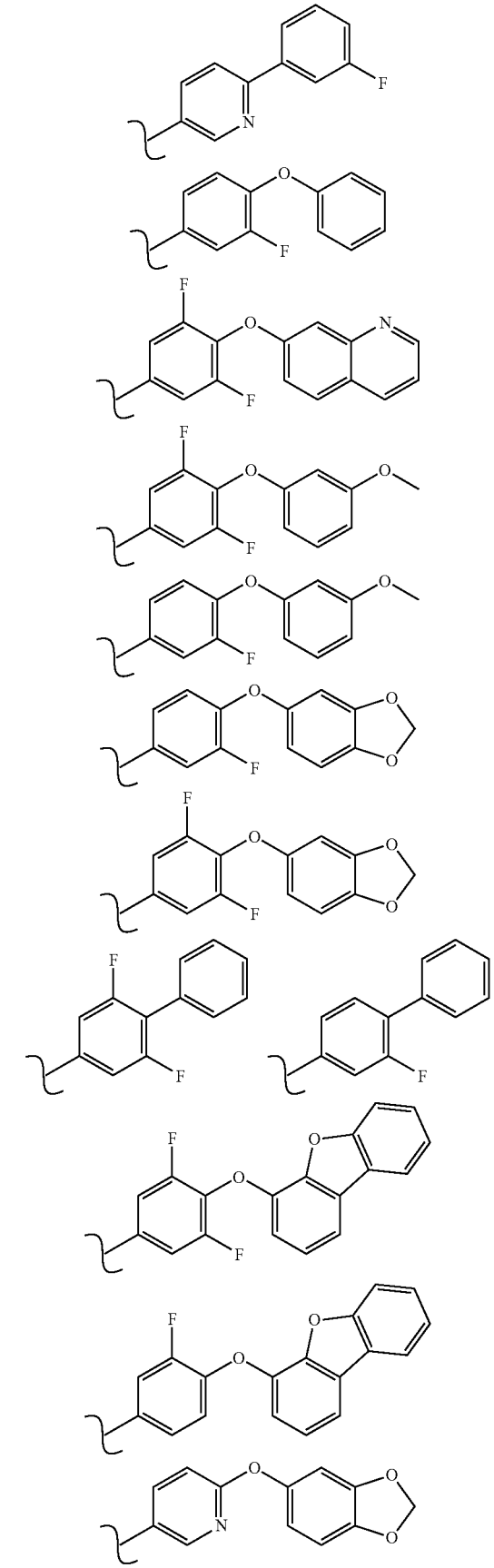

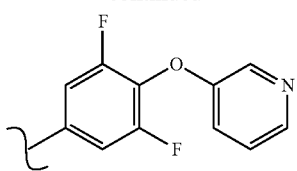
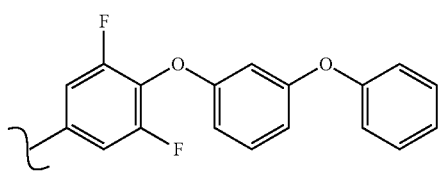
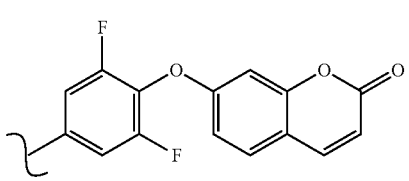
Additional compounds set forth in US Publication No. 2006/0199820 (U.S. application Ser. No. 10/518,110) can also be utilized. These include, but are not limited to,
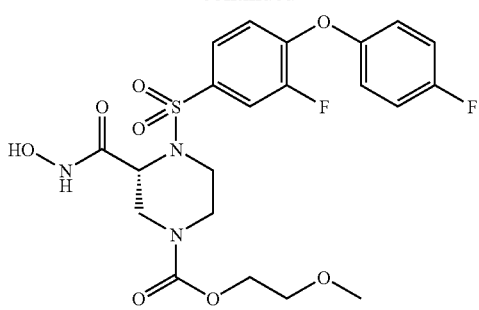
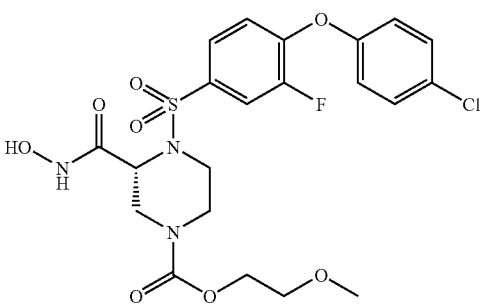
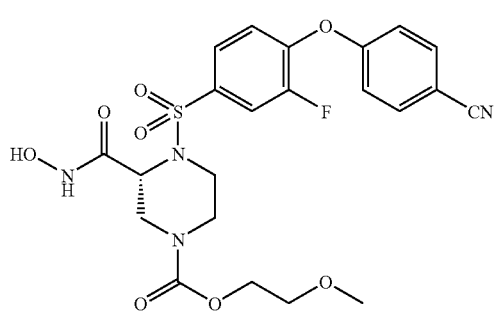
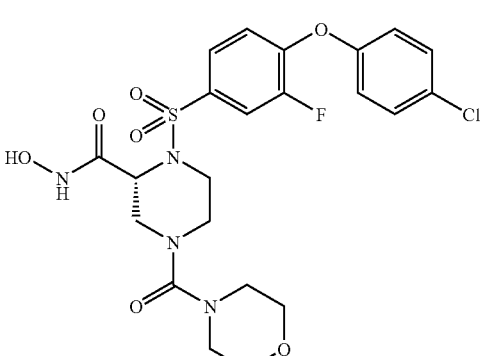
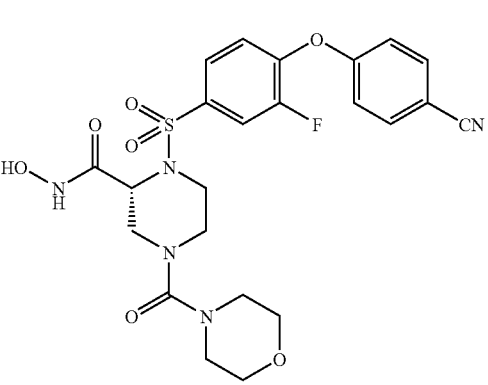

59
-continued
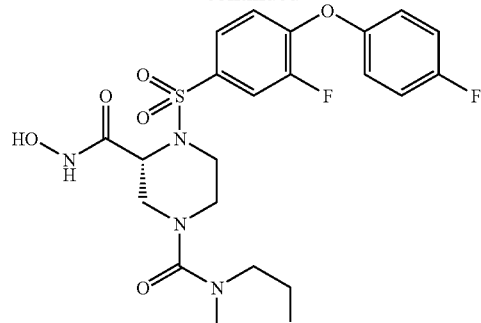
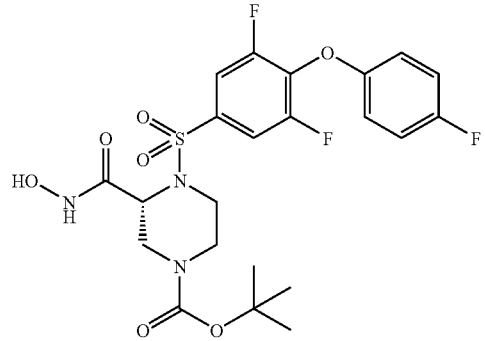
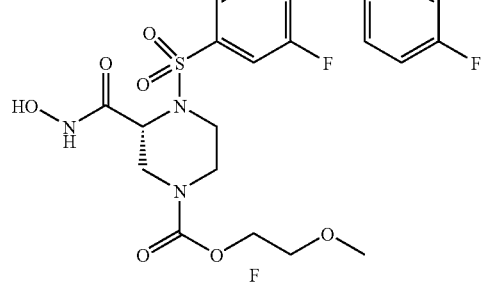
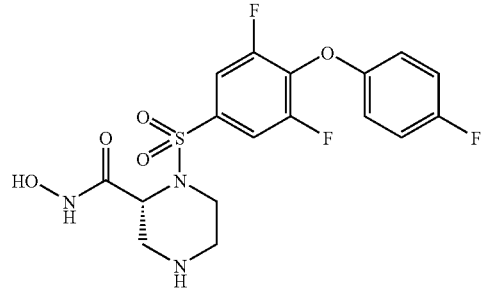
60
-continued
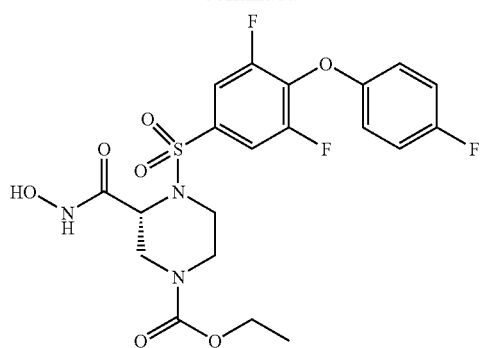
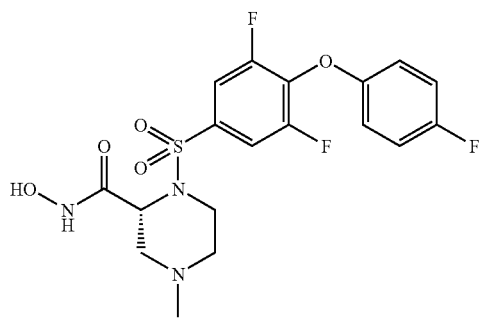
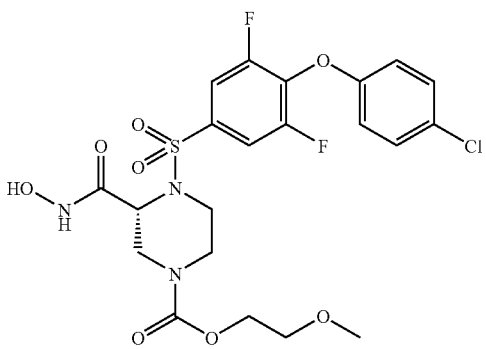
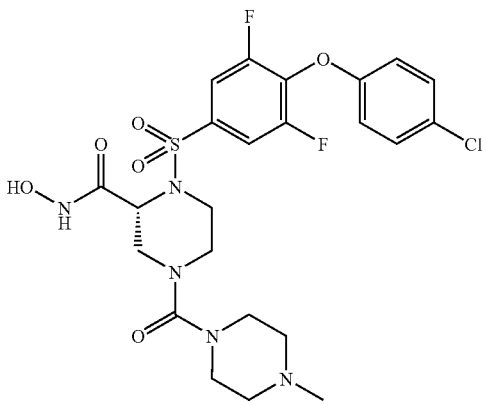

61
-continued
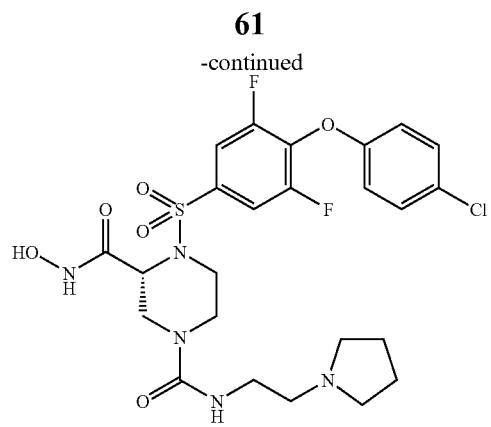
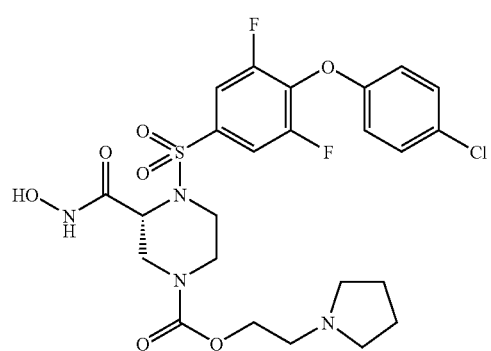
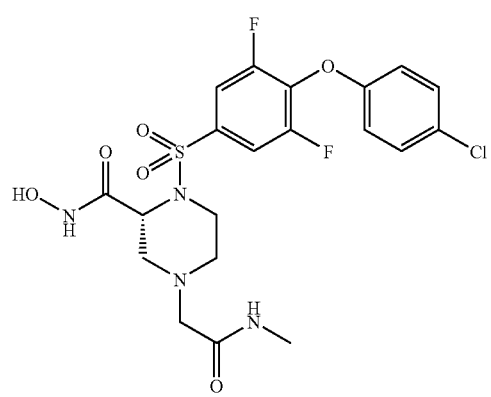
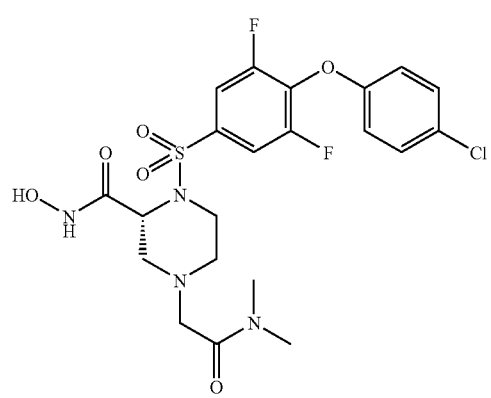
62
-continued
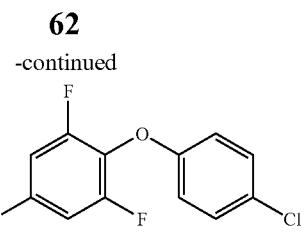
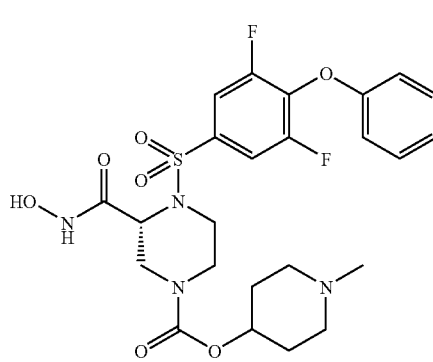
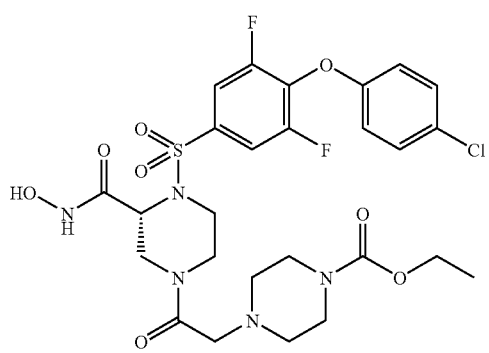
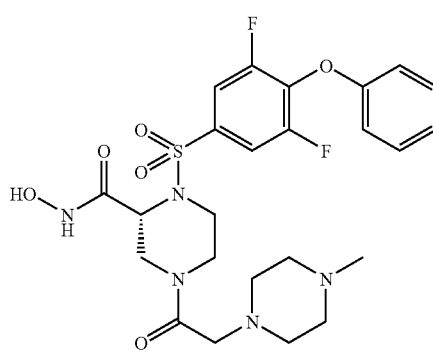

63
-continued
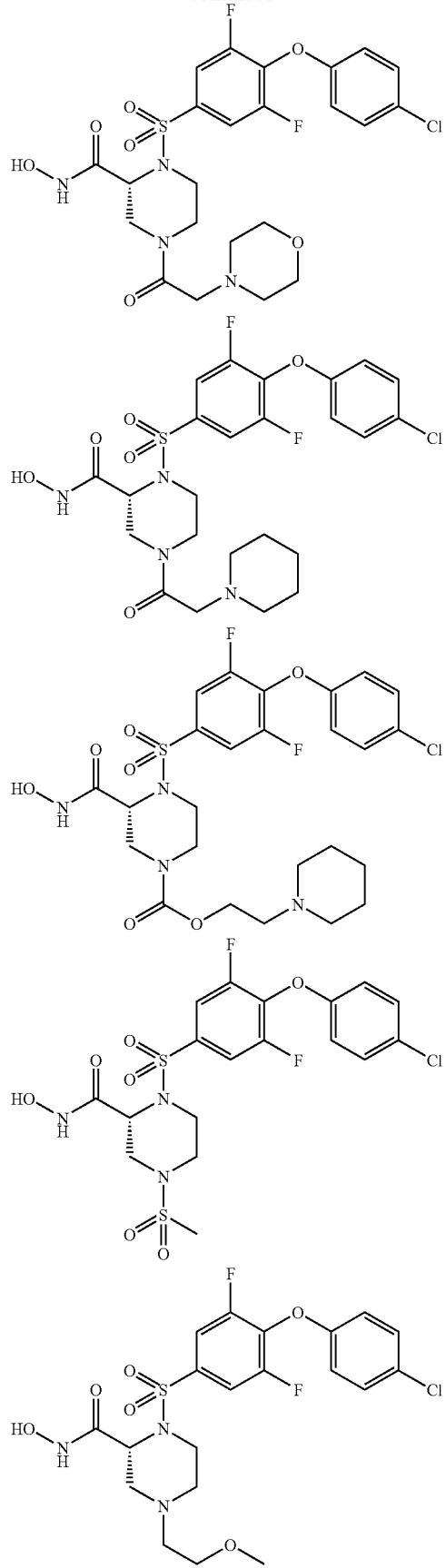
64
-continued
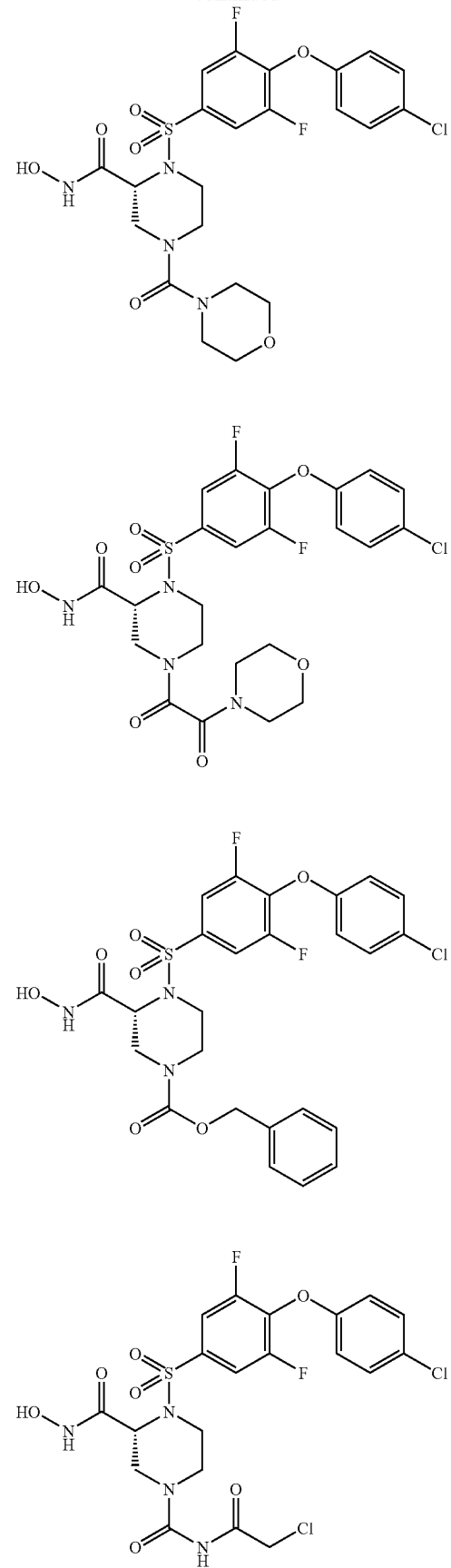

65
-continued
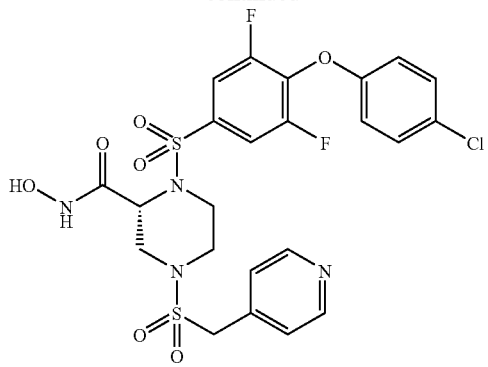
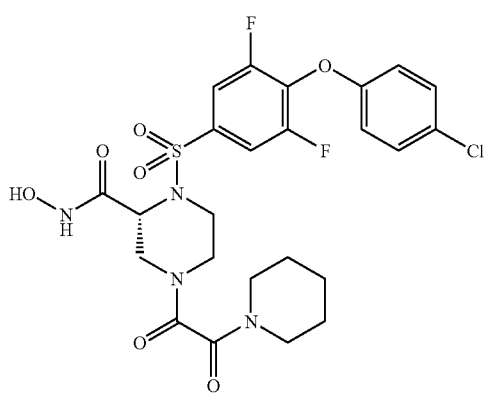
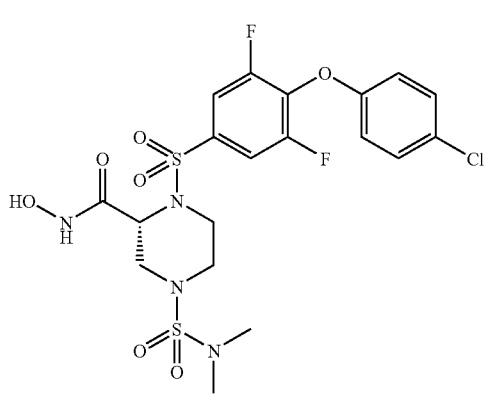
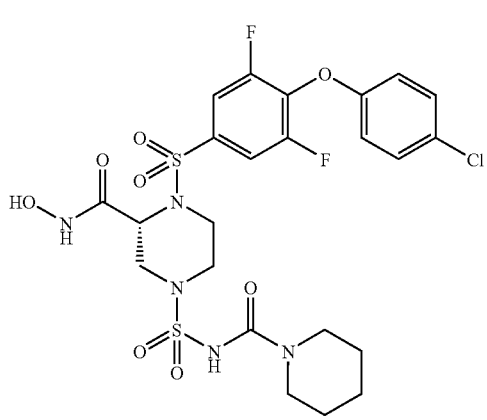
66
-continued
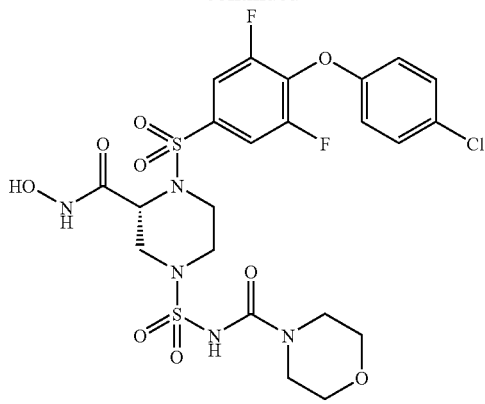
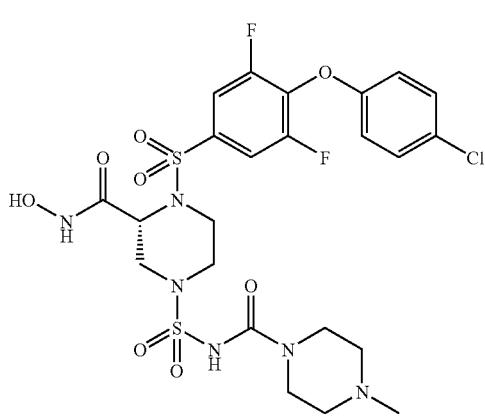
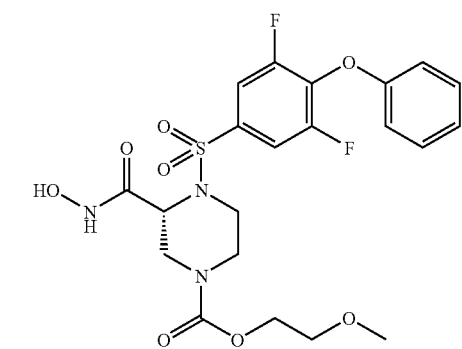
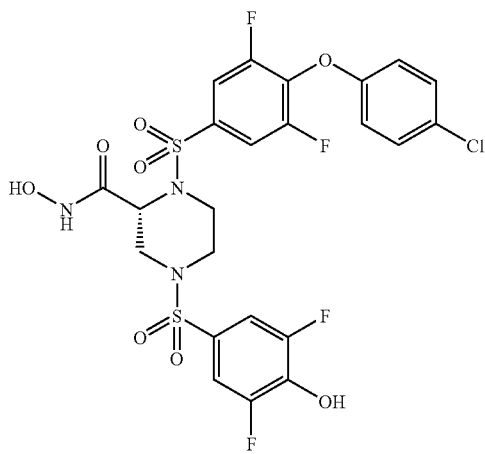

67
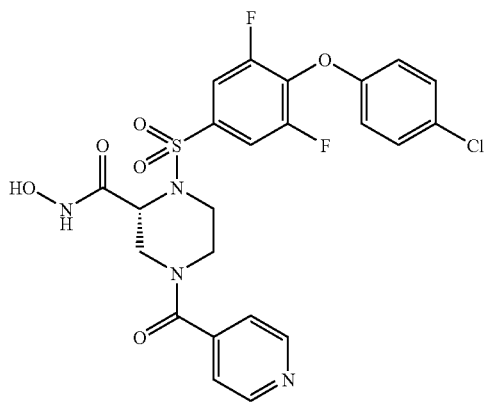
68
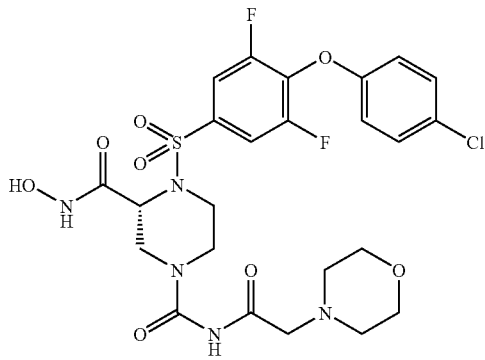
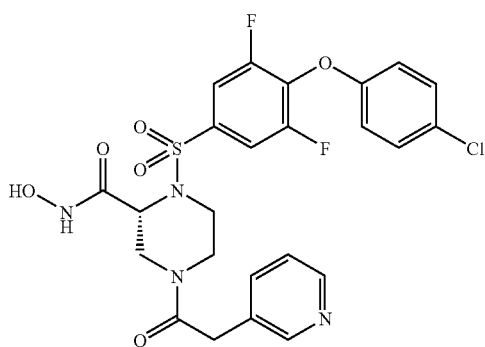
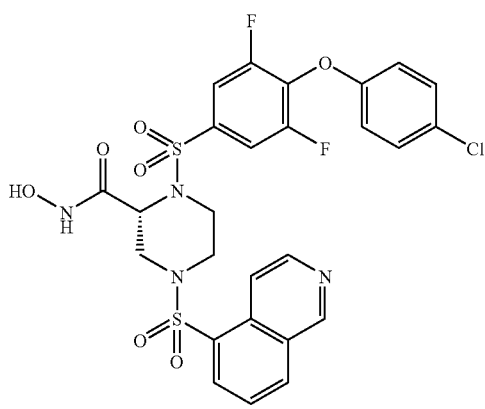
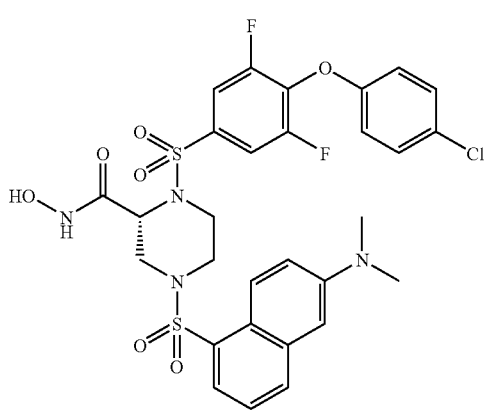

69
-continued
70
-continued
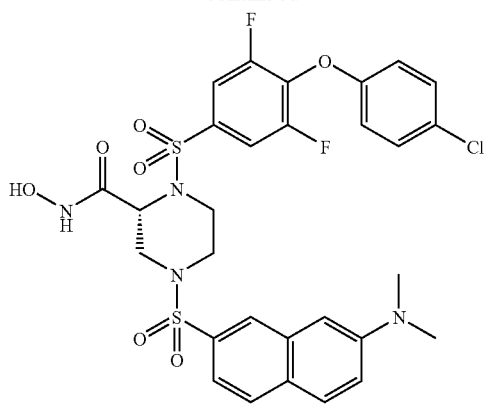
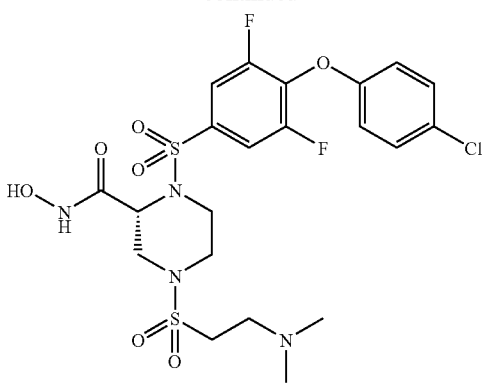

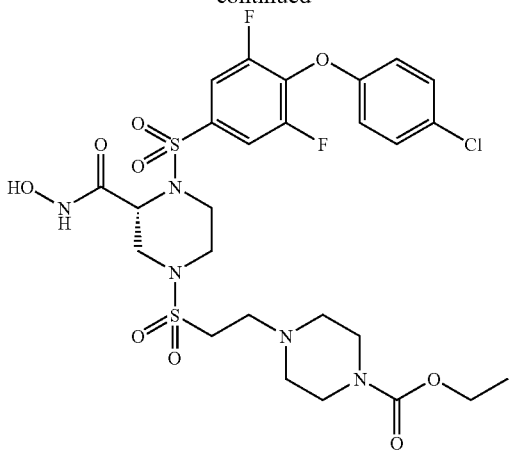
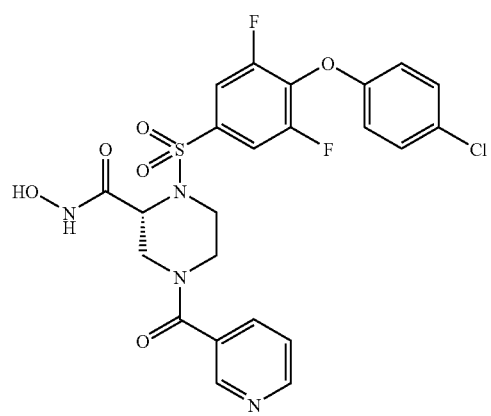
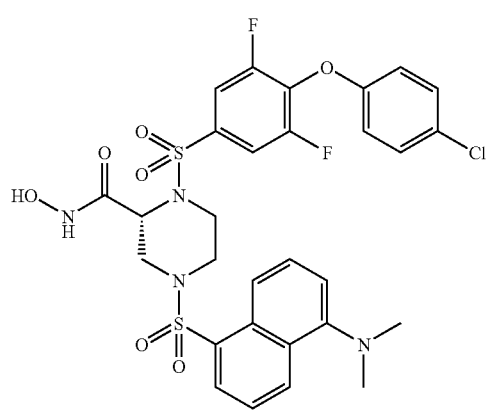
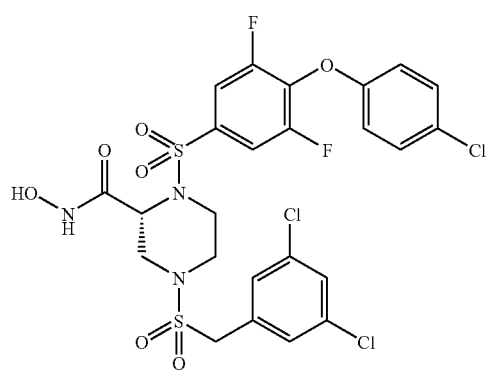
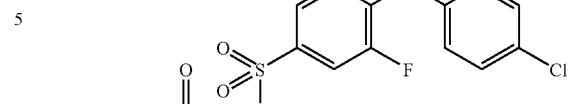
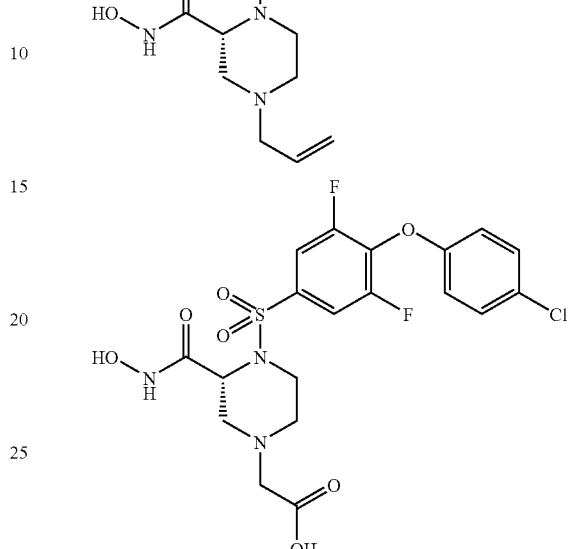
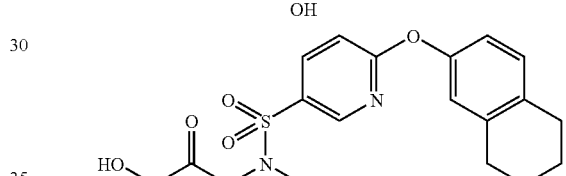
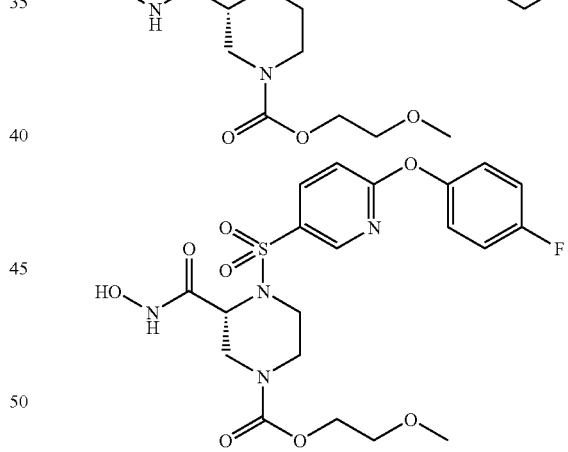
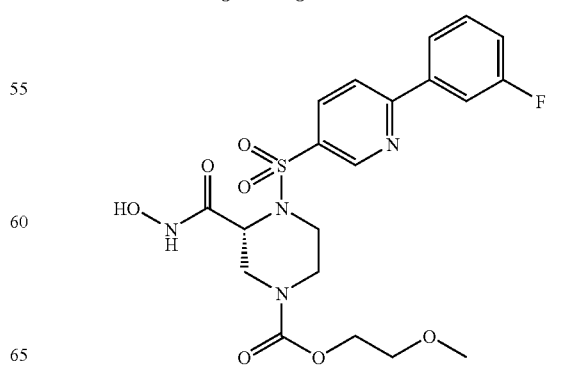

Also provided is a composition comprising a compound set forth in US Publication No. 2006/0199820 according to the formula,

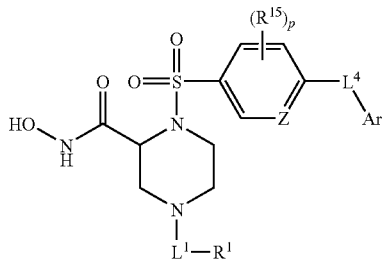

and pharmaceutically acceptable salts, esters, amides, and prodrugs thereof wherein, Z is $C(R^{15})=$, $-C(H)=$, or $-N=$;
Ar is aryl or heteroaryl, each optionally substituted; $R^{15}$ is fluoro;
p is 0, 1, 2, or 3
$L^1$ is $-C(O)S(O)2$, or $(CH_2)_n$; $L^4$ is nothing or $-O-$;
$R^1$ is H, $OR^{11}$, $-(CH2)_n R^{11}$, $C(O)R^{11}$, or $NR^{12}R^{13}$;
$R^{11}$, $R^{12}$, and $R^{13}$ independently are
J) $R^{50}$;
k) saturated or mono- or poly-unsaturated $C_5$-$C_{14}$-mono- or fused poly-cyclic hydrocarbyl, option-ally containing one or two annular heteroatoms per ring and optionally substituted with one or two $R_{50}$ substituents;
l) $C_1$-$C_6$ alkyl, $C_2$-$C_6$ alkenyl, $C_2$-$C_6$ alkynyl, or $-C(O)H$, each of which is optionally substituted with one, two or three substituents independently selected from $R^{50}$ and saturated or mono- or poly-unsaturated C5-C14 mono- or fused poly-cyclic hydrocarbyl, optionally containing one or two annular heteroatoms per ring and optionally substituted with one, two or three $R^{50}$ substituents;
or $R^{12}$ and $R^{13}$ together with the N to which they are covalently bound, a $C_5$-$C_6$ heterocycle optionally containing a second annular heteroatom and optionally substituted with one or two $R^{50}$ substituents; and
$R^{50}$ is $R^{51}$-$L^3$-$(CH2)$-;
$L^3$ is $-O-$, $-NH-$, $-S(O)_{0-2}$, $-C(O)-$, $C(O)O-$, $-C(O)NH-$, $-OC(O)-$, $-NHC(O)-$, $C_6H_4$, or a direct bond;
$R^{51}$ is H, $C_1$-$C_6$ alkyl, $C_2$-$C_6$-alkenyl, $C_2$-$C_6$-alkynyl, halo, $-CF_3$, $-OCF_3$, $-OH$, $-NH_2$, mono-$C_1$-$C_6$alkyl amino, di-$C_1$-$C_6$alkyl amino, $-SH$, $-CO_2H$, $-CN$, $-NO_2$, $SO_3H$, or a saturated or mono- or poly-unsaturated $C_5$-$C_{14}$-mono- or fused poly-cyclic hydrocarbyl, optionally containing one or two annular heteroatoms per ring and optionally substituted with one, two, or three substituents;
wherein n is 0, 1, 2, or 3;
provided that an O or S is not singly bonded to another O or S in a chain of atoms.

Also provided are compounds wherein $L^1$-$R^1$ is selected from:

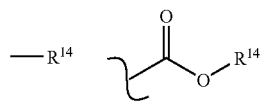
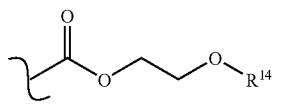

-continued

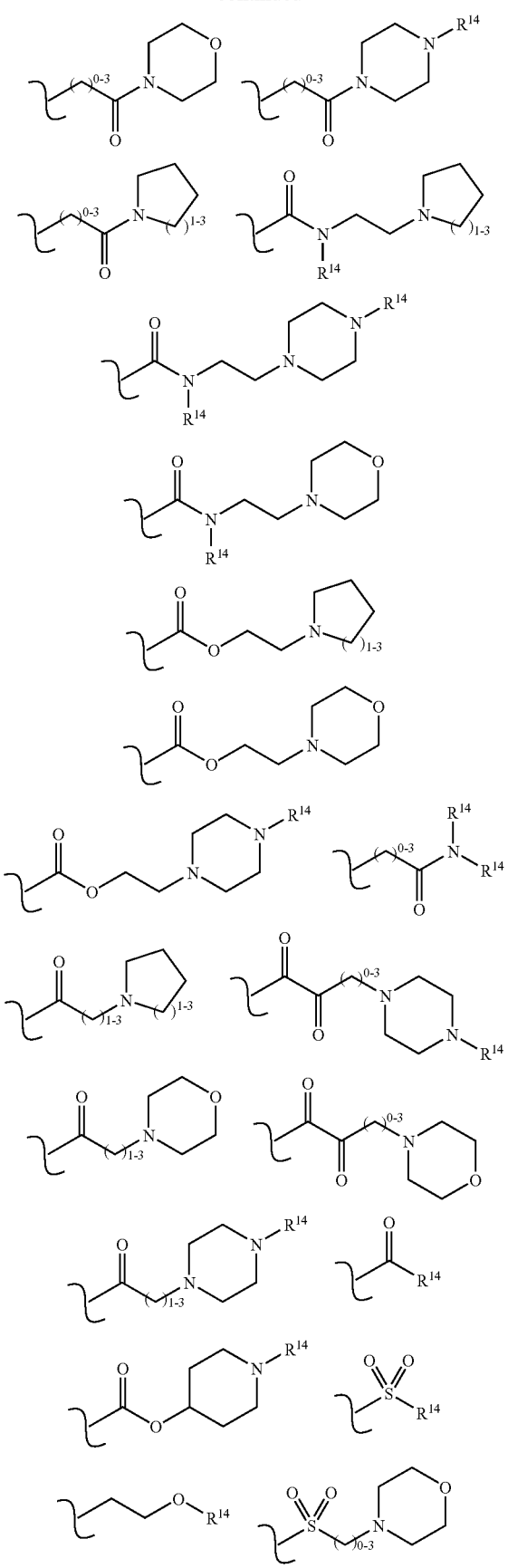

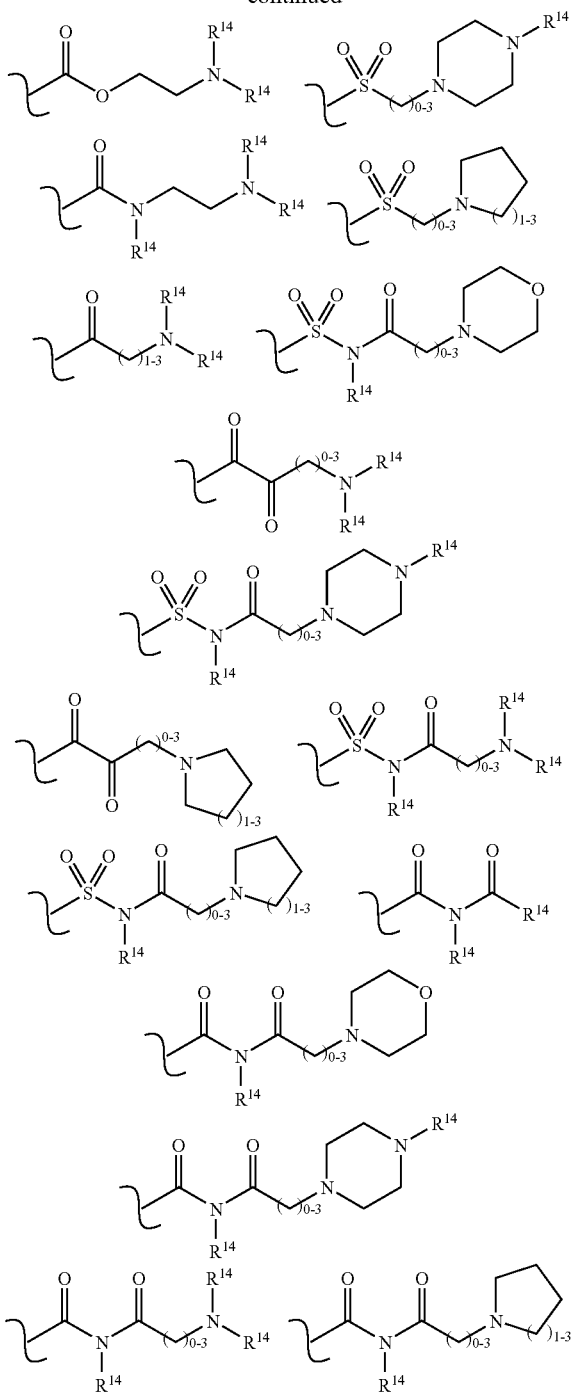

wherein each $R^{14}$ is independently selected from H, $(CH_2)_{13}CO_2H$, alkyl, alkoxy, alklenyl, aryl, heteroaryl, arylalkyl, and heteroarylalkyl.

Other compositions that can be utilized in the methods of the present invention include, but are not limited to a composition comprising a metalloproteinase inhibitor such as a TACE (TNF-alpha converting enzyme) inhibitor, IC-3 (N-{D,L-[2(hydroxyaminocarbonyl)methyl]-4-methyl-pentanoyl}-L-alanine, 2 aminoethyl amide), GM6001 (NHOHCOCH$_2$CH9(I-Bu)CO-Trp-NHMe), GW947 1, BB-94 (batimastat), an inhibitor of TIMP-1, an inhibitor of TIMP-2, an inhibitor of TIMP-3, a high affinity zinc binding substituted hydroxamate, a high affinity zinc binding carboxylate, a high affinity zinc binding thiol, a high affinity zinc binding phosphonate, a high affinity zinc binding aminodiathiazol, a high affinity zinc binding catechol, EDTA and 1,10-pheanthroline.

In addition to the compounds described above, all of the disclosure and all of the compounds disclosed in U.S. Patent Application Publication No. 2005/0113344 (U.S. application Ser. No. 10/965,215), U.S. Patent Application Publication No. 2006/0199820 (U.S. application Ser. No. 10/518,110), U.S. Patent Application Publication No. 2006/0177443 (U.S. application Ser. No. 11/392,436), U.S. Patent Application Publication No. 2006/0140957 (U.S. application Ser. No. 10/544,701), (U.S. application Ser. No. 11/085,949), U.S. Patent Application Publication No. 2004/0247602 (U.S. application Ser. No. 10/817,718), U.S. Patent Application Publication No. 2003/0108978 (U.S. application Ser. No. 10/281,458), U.S. Patent Application Publication No. 2002/0168755 (U.S. application Ser. No. 10/145,014), U.S. Patent Application Publication No. 2002/0106787 (U.S. application Ser. No. 09/982,308) and U.S. Patent Application Publication No. 20020042368 (U.S. application Ser. No. 09/792,200) are incorporated herein by this reference as are the methods of making and utilizing these compounds for decreasing the expression of ADAM10 in a cell, in vitro, ex vivo and in vivo. These compounds can be screened for effectiveness and utilized in a method of decreasing infection in a cell by a pathogen comprising contacting a cell with one or more of the compounds set forth in U.S. Patent Application Publication No. 2005/0113344 (U.S. application Ser. No. 10/965,215), U.S. Patent Application Publication No. 2006/0199820 (U.S. application Ser. No. 10/518,110), U.S. Patent Application Publication No. 2006/0177443 (U.S. application Ser. No. 11/392,436), U.S. Patent Application Publication No. 2006/0140957 (U.S. application Ser. No. 10/544,701), U.S. Patent Application Publication No. 2005/0227973 (10/498,338), U.S. Patent Application Publication No. 2005/0171024 (U.S. application Ser. No. 11/085,949), U.S. Patent Application Publication No. 2004/0247602 (U.S. application Ser. No. 10/817,718), U.S. Patent Application Publication No. 2003/0108978 (U.S. application Ser. No. 10/281,458), U.S. Patent Application Publication No. 2002/0168755 (U.S. application Ser. No. 10/145,014), U.S. Patent Application Publication No. 2002/0106787 (U.S. application Ser. No. 09/982,308) or U.S. Patent Application Publication No. 20020042368 (U.S. application Ser. No. 09/792,200) that decreases expression or activity of ADAM10. Also contemplated by the present invention are amounts of these compounds and formulations suitable for treating or preventing a pathogenic infection and especially a viral infection. The pharmaceutically acceptable salt, solvate, biohydrolyzable ester, biohydrolyzable amide, affinity reagent or prodrug of these compounds are also provided.

Another compound that can be utilized is galardin, also known as Ilomastat. The following shows the chemical structure of galardin (Butanediamide, N4-hydroxy-N1-((1S)-1-(1H-indol-3-ylmethyl)-2-(methylamino)-2-oxoethyl)-2-(2-methylpropyl)-, (2R)—). The IUPAC name for galardin is 2-(hydroxycarbamoylmethyl)-N-[2-(1H-indol-3-yl)-1-(methylcarbamoyl)ethyl]-4-methyl-pentanamide

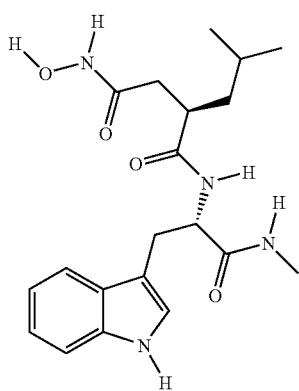

The present invention also provides a pharmaceutical composition comprising any of the compounds set forth herein and a pharmaceutically acceptable carrier.

Small Molecules

The present invention also provides the design and synthesis of small molecules that inhibit ADAM10 activity. A crystal structure can be determined for ADAM10 which can then be utilized in structure based design of specific inhibitors of ADAM10. In particular, the substrate-binding site can be targeted for structure-based design of specific ADAM10 inhibitors. For additional information on the crystal structure and design of an ADAM protein inhibitor, see Orth et al. "Crystal structure of the catalytic domain of human ADAM33" J. Mol. Biol. 335(1):129-37 (2004)).

Other methods of decreasing ADAM10 expression and/or activity include methods of interrupting or altering transcription ADAM10 mRNA molecules by site-directed mutagenesis (including mutations caused by a transposon or an insertional vector). Chemical mutagenesis can also be performed in which a cell is contacted with a chemical (for example ENU) that mutagenizes nucleic acids by introducing mutations into the ADAM10 gene. Radiation can also be utilized to effect mutagenesis. Alternatively, as stated above, an antibody that specifically binds to ADAM10 and decreases its activity can also be utilized.

Screening Methods

The present invention provides a method of identifying an agent that decreases infection by a pathogen comprising: a) administering the agent to a cell containing a cellular gene encoding ADAM10; and b) detecting the level and/or activity of the gene product produced by the cellular gene encoding ADAM10, a decrease or elimination of the gene product and/or gene product activity indicating a compound that decreases infection by a pathogen. For example, the agent can interfere with gene expression and/or the activity of the protein or polypeptide product of the gene. In the methods of the present invention, the test compounds or agents of the invention can be delivered before or after contacting a cell with a pathogen or simultaneously with the pathogen. The pathogen can be, but is not limited to, a virus, a bacterium, a fungi or a parasite.

Also provided by the present invention is a method of identifying an agent that decreases infection by a pathogen comprising: a) administering the agent to a cell containing a cellular gene encoding ADAM10, b) contacting the cell with a pathogen; c) detecting the level of infection; and d) associating the level of infection with the level of expression of ADAM10 or the activity of ADAM10, a decrease or elimination of infection associated with a decrease or elimination of ADAM10 expression and/or ADAM10 activity indicating that the agent is an agent that decreases infection.

The methods described above can be utilized to identify any agent with an activity that decreases infection, prevents infection or promotes cell survival after infection with a pathogen(s). Therefore, the cell can be contacted with any infectious pathogen. Infection also includes the introduction of other infectious agents, such as a non-recombinant virus, recombinant virus, plasmid, bacteria, prion, eukaryotic microbe, or other agent capable of infecting a host, such as a cell in cell culture or a cell of a subject. Such infection can be in vitro, ex vivo or in vivo.

The antiviral agents identified utilizing these methods can be used to inhibit viral infection in cells either in vitro, ex vivo or in vivo. Similarly, the antibacterial agents identified utilizing these methods can be used to inhibit bacterial infection in cells either in vitro, ex vivo or in vivo. The antifungal agents identified utilizing these methods can be used to inhibit fungal infection in cells either in vitro, ex vivo or in vivo. The antiparasitic agents identified utilizing these methods can be used to inhibit parasitic infection in cells either in vitro, ex vivo or in vivo.

In the methods of the present invention any cell that can be infected with a virus or other pathogen, such as bacteria, parasite or fingi can be utilized. The cell can be prokaryotic or eukaryotic, such as a cell from an insect, fish, crustacean, mammal, bird, reptile, yeast or a bacterium, such as E. coli. The cell can be part of an organism, or part of a cell culture, such as a culture of mammalian cells or a bacterial culture. The cell can also be in a nonhuman subject thus providing in vivo screening of agents that decrease infection by a pathogen.

The test compounds used in the methods described herein can be, but are not limited to, chemicals, small molecules, inorganic molecules, organic molecules, drugs, proteins, cDNAs, large molecules, antibodies, morpholinos, triple helix molecule, a peptide, siRNAs, shRNAs, miRNAs, antisense RNAs, ribozymes or any other compound now known or identified in the future that interferes with the expression and/or activity of ADAM10. Agents identified with the disclosed approaches can be used as lead compounds to identify other agents having even greater anti-pathogen activity, such as antiviral or antibacterial activity. For example, chemical analogs of identified chemical entities, or variants, fragments or fusions of peptide agents, can be tested for their ability to decrease infection using the disclosed assays. Candidate agents can also be tested for safety in animals and then used for clinical trials in animals or humans.

In the methods described herein, once the cell containing a cellular gene encoding ADAM10 has been contacted with an agent, the level of infection can be associated with the level of gene expression and/or activity, such that a decrease or elimination of infection associated with a decrease or elimination of gene expression and/or activity indicates that the agent is effective against the pathogen. These methods can be utilized to assess the effects of an agent on bacterial infection, antiviral infection, antifungal infection, antiparasitic infection, to name a few. For example, the level of viral infection can be measured in a cell after administration of siRNA that inhibits ADAM10. If there is a decrease in viral infection, then the siRNA is an effective antiviral agent. The level of viral infection can be assessed by measuring an antigen or other product associated with a particular viral infection as set forth in the Examples of this application (for example, p24 for HIV infection). If there is a decrease in p24 levels after administration of an siRNA directed to ADAM10, the siRNA targeting that gene is an effective antiviral agent against HIV. The level of viral infection can also be measured by real-time quantitative reverse transcription-polymerase chain reaction (RT-PCR) assay (See for example, Payungporn et al. "Single step multiplex real-time RT-PCR for H5N1 influenza A virus detection." *J Virol Methods*. Sep. 22, 2005; Landolt et al. "Use of real-time reverse transcriptase polymerase chain reaction assay and cell culture methods for detection of swine influenza A viruses" *Am J Vet Res.* 2005 January; 66(1): 119-24)

Similarly, the level of viral infection can be measured in a cell, utilizing the methods set forth above and known in the art, after administration of a chemical, small molecule, drug, protein, cDNA, antibody, shRNA, miRNA, morpholino, antisense RNA, ribozyme or any other compound. If there is a decrease in viral infection, then the chemical, small molecule, drug, protein, cDNA, antibody, shRNA, miRNA, morpholino, antisense RNA, ribozyme or any other compound is an effective antiviral agent. Similar methods can be utilized to measure the levels of other types of infection such as bacterial infection, fungal infection and parasitic infection.

Antiviral agents found to be effective for one virus, can also be effective for other viruses, particularly viruses from the same family. However, it is also contemplated that an agent found to be effective against HIV can also be effective against influenza or avian flu or any other virus. Therefore, antiviral agents identified for one virus can be tested utilizing the methods of the present invention for antiviral activity against other viruses. It is also contemplated that compounds that effectively decrease ADAM10 activity to decrease viral infection can also be utilized to decrease infection by other pathogens, if ADAM10 is found to be involved in the life cycle of another pathogen or infectious agent, such as, but not limited to a virus, a bacterium, a fungus or a parasite.

The level of the gene product can be measured by any standard means, such as by detection with an antibody specific for the protein. The nucleic acids set forth herein and fragments thereof can be utilized as primers to amplify nucleic acid sequences, such as a gene transcript of ADAM10 by standard amplification techniques. For example, expression of a gene transcript can be quantified by real time PCR using RNA isolated from cells. A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference in its entirety for PCR methods. One of skill in the art would know how to design and synthesize primers that amplify any of the nucleic acid sequences set forth herein for ADAM10 or a fragment thereof.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified fragment, can be analyzed by one of a number of methods known in the art. The nucleic acid can be sequenced by dideoxy or other methods. Hybridization with the sequence can also be used to determine its presence, by Southern blots, dot blots, etc.

The ADAM10 genes and nucleic acids of the invention can also be used in polynucleotide arrays. Polynucleotide arrays provide a high throughput technique that can assay a large number of polynucleotide sequences in a single sample. This technology can be used, for example, to identify samples with reduced expression of a ADAM10 as compared to a control sample. This technology can also be utilized to determine the effects of reduced expression of ADAM10 on other genes. In this way, one of skill in the art can identify genes that are upregulated or downregulated upon reduction of ADAM10 expression. Similarly, one of skill in the art can identify genes that are upregulated or downregulated upon increased expression of ADAM10. This allows identification of other genes that are upregulated or downregulated upon modulation of ADAM10 expression that can be targets for therapy, such as antiviral therapy, antibacterial therapy, antiparasitic therapy or antifungal therapy.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from ADAM10 nucleotide sequences set forth under GenBank Accession Nos. herein and other nucleic acid sequences that would be selected by one of skill in the art depending on what genes, in addition to ADAM10 are being analyzed.

The array can also be a microarray that includes probes to different polymorphic alleles of ADAM10. A polymorphism exists when two or more versions of a nucleic acid sequence exist within a population of subjects. For example, a polymorphic nucleic acid can be one where the most common allele has a frequency of 99% or less. Different alleles can be identified according to differences in nucleic acid sequences, and genetic variations occurring in more than 1% of a population (which is the commonly accepted frequency for defining polymorphism) are useful polymorphisms for certain applications.

The allelic frequency (the proportion of all allele nucleic acids within a population that are of a specified type) can be determined by directly counting or estimating the number and type of alleles within a population. Polymorphisms and methods of determining allelic frequencies are discussed in Hartl, D. L. and Clark, A. G., Principles of Population Genetics, Third Edition (Sinauer Associates, Inc., Sunderland Mass., 1997), particularly in chapters 1 and 2.

These microarrays can be utilized to detect polymorphic alleles in samples from subjects. Such alleles may indicate that a subject is more susceptible to viral infection or less susceptible to viral infection. For example, since the present invention shows that a disruption in ADAM10 or decreased ADAM10 expression results in decreased viral infection, such microarrays can be utilized to detect polymorphic versions of ADAM10 that result in decreased gene expression and/or decreased activity of the gene product to identify subjects that are less susceptible to viral infection.

The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

The level of gene product can be compared to the level of the gene product in a control cell not contacted with the compound. The level of gene product can be compared to the level of the gene product in the same cell prior to addition of the compound. Activity or function, can be measured by any standard means, such as by enzymatic assays that measure the conversion of a substrate to a product or binding assays that measure the binding of ADAM10 to another protein, for example.

Moreover, the regulatory region of ADAM10 can be functionally linked to a reporter gene and compounds can be screened for inhibition of reporter gene expression. Such regulatory regions can be isolated from genomic sequences and identified by any characteristics observed that are characteristic for regulatory regions of the species and by their relation to the start codon for the coding region of the gene. As used herein, a reporter gene encodes a reporter protein. A reporter protein is any protein that can be specifically detected when expressed. Reporter proteins are useful for detecting or quantitating expression from expression sequences. Many reporter proteins are known to one of skill in the art. These include, but are not limited to, β-galactosidase, luciferase, and alkaline phosphatase that produce specific detectable products. Fluorescent reporter proteins can also be used, such as green fluorescent protein (GFP), cyan fluorescent protein (CFP), red fluorescent protein (RFP) and yellow fluorescent protein (YFP).

Viral infection can also be measured via cell based assays. Briefly, cells (20,000 to 2,500,000) are infected with the desired pathogen, and the incubation continued for 3-7 days. The antiviral agent can be applied to the cells before, during, or after infection with the pathogen. The amount of virus and agent administered can be determined by skilled practitioners. In some examples, several different doses of the potential therapeutic agent can be administered, to identify optimal dose ranges. Following transfection, assays are conducted to determine the resistance of the cells to infection by various agents.

For example, if analyzing viral infection, the presence of a viral antigen can be determined by using antibody specific for the viral protein then detecting the antibody. In one example, the antibody that specifically binds to the viral protein is labeled, for example with a detectable marker such as a fluorophore. In another example, the antibody is detected by using a secondary antibody containing a label. The presence of bound antibody is then detected, for example using microscopy, flow cytometry and ELISA. Similar methods can be used to monitor bacterial, protozoal, or fungal infection (except that the antibody would recognize a bacterial, protozoal, or fungal protein, respectively).

Alternatively, or in addition, the ability of the cells to survive viral infection is determined, for example, by performing a cell viability assay, such as trypan blue exclusion.

The amount of ADAM10 protein in a cell, can be determined by methods standard in the art for quantitating proteins in a cell, such as Western blotting, ELISA, ELISPOT, immunoprecipitation, immunofluorescence (e.g., FACS), immunohistochemistry, immunocytochemistry, etc., as well as any other method now known or later developed for quantitating protein in or produced by a cell.

The amount of an ADAM10 nucleic acid in a cell can be determined by methods standard in the art for quantitating nucleic acid in a cell, such as in situ hybridization, quantitative PCR, RT-PCR, Taqman assay, Northern blotting, ELISPOT, dot blotting, etc., as well as any other method now known or later developed for quantitating the amount of a nucleic acid in a cell.

The ability of an antiviral agent to prevent or decrease infection by a virus, such as HIV, Ebola, influenza A, SARS, smallpox, to name a few, can be assessed in an animal model. Several animal models for viral infection are known in the art. For example, mouse HIV models are disclosed in Sutton et al. (*Res. Initiat Treat. Action,* 8:22-4, 2003) and Pincus et al. (*AIDS Res. Hum. Retroviruses* 19:901-8, 2003); guinea pig models for Ebola infection are disclosed in Parren et al. (*J. Virol.* 76:6408-12, 2002) and Xu et al. (*Nat. Med.* 4:37-42, 1998); and cynomolgus monkey (*Macaca fascicularis*) models for influenza infection are disclosed in Kuiken et al. (*Vet. Pathol.* 40:304-10, 2003).

Other animal models for influenza infection are also available. These include, but are not limited to, a cotton rat model disclosed by Ottolini et al. (*J. Gen. Virol.,* 86(Pt 10): 2823-30, 2005), as well as ferret and mouse models disclosed by Maines et al. (J. Virol. 79(18):11788-11800, 2005).

One of skill in the art would know how to select an animal model for assessing the in vivo activity of an agent for its ability to decrease infection by viruses, bacteria, fungi and parasites.

Such animal models can also be used to test agents for an ability to ameliorate symptoms associated with viral infection. In addition, such animal models can be used to determine the $LD_{50}$ and the $ED_{50}$ in animal subjects, and such data can be used to determine the in vivo efficacy of potential agents. Animal models can also be used to assess antibacterial, antifungal and antiparasitic agents.

Animals of any species, including, but not limited to, birds, ferrets, cats, mice, rats, rabbits, fish (for example, zebrafish) guinea pigs, pigs, micro-pigs, goats, and non-human primates, e.g., baboons, monkeys, and chimpanzees, can be used to generate an animal model of viral infection, bacterial infection, fungal infection or parasitic infection if needed.

For example, for a model of viral infection, the appropriate animal is inoculated with the desired virus, in the presence or absence of the antiviral agent. The amount of virus and agent administered can be determined by skilled practitioners. In some examples, several different doses of the potential therapeutic agent (for example, an antiviral agent) can be administered to different test subjects, to identify optimal dose ranges. The therapeutic agent can be administered before, during, or after infection with the virus. Subsequent to the treatment, animals are observed for the development of the appropriate viral infection and symptoms associated therewith. A decrease in the development of the appropriate viral infection, or symptoms associated therewith, in the presence of the agent provides evidence that the agent is a therapeutic agent that can be used to decrease or even inhibit viral infection in a subject. Similar models and approaches can be used for bacterial, fungal and parasitic infections.

The present invention also provides a method of making compound that reduces infection, comprising: a) synthesizing a compound; b) administering the compound to a cell containing a cellular gene encoding ADAM10, c) contacting the cell with an infectious pathogen; c) detecting the level of infection; d) associating the level of infection with the level of expression of the gene encoding ADAM10 or the activity of the protein encoded by the ADAM10 gene, a decrease or elimination of infection associated with a decrease or elimination of gene expression and/or activity indicating that a compound that reduces infection was made. The cell can be in vitro, ex vivo or in vivo.

Also provided is a method of making compound that reduces infection, comprising: a) administering the compound to a cell containing a cellular gene that encodes ADAM10, b) contacting the cell with an infectious pathogen; c) detecting the level of infection; d) associating the level of infection with the level of expression of the ADAM10 gene or the activity of the protein encoded by the ADAM10 gene, a decrease or elimination of infection associated with a decrease or elimination of gene expression and/or activity indicating that a compound is a compound that reduces infection; and e) placing the compound in a pharmaceutically acceptable carrier. The compounds that reduce infection can be antiviral, antibacterial, antifungal or antiparasitic compounds or any compound that reduces infection by an infectious agent. The cell can be in vitro, ex vivo or in vivo.

ADAM10 Pathways

The present invention also provides proteins and the nucleic acids encoding proteins that interact with ADAM10 either directly or indirectly in a cell. Thus, genes that are upstream or downstream of ADAM10 in pathways involving ADAM10 are also provided by the present invention as targets for decreasing infection. For example, ADAM10 is involved in the Notch signaling pathway. Therefore, all genes and gene products of the Notch signaling pathway are contemplated herein as targets for decreasing infection. Other examples of proteins that interact with ADAM10 include, but are not limited to E-cadherin, TNF-α, N-cadherin and Eve-1.

Other proteins that modulate ADAM10 activity, either directly or indirectly can be identified. Therefore, the present invention provides a method of identifying a modulator of ADAM10 that is involved in infection comprising: a) inhibiting the expression of a putative modulator of ADAM10 in a cell that expresses ADAM10; b) contacting the cell with a pathogen; c) detecting the level of infection; and d) associating the level of viral infection with the level of ADAM10 and/or ADAM10 activity, a decrease or elimination of viral infection associated with a decrease or elimination of ADAM10 and/or ADAM10 activity indicating that the putative modulator of ADAM10 is a modulator of ADAM10 that is involved in infection.

Pharmaceutical Compositions and Modes of Administration

The present invention provides a method of decreasing infection by a pathogen in a subject by decreasing the expression or activity of ADAM10 in the subject, said method comprising administering to the subject an effective amount of a composition that decreases the expression or activity of ADAM10 in the subject. The composition can comprise one or more of, a chemical, a compound, a small molecule, an inorganic molecule, an organice molecule, a drug, a protein, a cDNA, a peptide, an antibody, a morpholino, a triple helix molecule, an siRNA, an shRNAs, an miRNA, an antisense nucleic acid or a ribozyme that decreases the expression or activity of ADAM10. These compositions can be administered to a subject alone or in combination with other therapeutic agents described herein, such as anti-viral compounds, antibacterial agents, antifungal agents, antiparasitic agents, anti-inflammatory agents, anti-cancer agents, etc. Examples of viral infections, bacterial infections, fungal infections parasitic infections are set forth above. The compounds set forth herein or identified by the screening methods set forth herein can be administered to a subject to decrease infection by any pathogen or infectious agent set forth herein. Any of the compounds set forth herein or identified by the screening methods of the present invention can also be administered to a subject to decrease infection by any pathogen, now known or later discovered in which ADAM10 is involved.

Various delivery systems for administering the therapies disclosed herein are known, and include encapsulation in liposomes, microparticles, microcapsules, expression by recombinant cells, receptor-mediated endocytosis (Wu and Wu, *J. Biol. Chem.* 1987, 262:4429-32), and construction of therapeutic nucleic acids as part of a retroviral or other vector. Methods of introduction include, but are not limited to, mucosal, topical, intradermal, intramuscular, intraperitoneal, vaginal, rectal, intravenous, subcutaneous, intranasal, and oral routes. The compounds can be administered by any convenient route, for example by infusion or bolus injection, by absorption through epithelial or mucocutaneous linings (for example, oral mucosa, rectal, vaginal and intestinal mucosa, etc.) and can be administered together with other biologically active agents. Administration can be systemic or local. Pharmaceutical compositions can be delivered locally to the area in need of treatment, for example by topical application or local injection.

Pharmaceutical compositions are disclosed that include a therapeutically effective amount of a RNA, DNA, antisense molecule, ribozyme, siRNA, shRNA molecule, miRNA molecule, drug, protein, small molecule, peptide inorganic molecule, organic molecule, antibody or other therapeutic agent, alone or with a pharmaceutically acceptable carrier. Furthermore, the pharmaceutical compositions or methods of treatment can be administered in combination with (such as before, during, or following) other therapeutic treatments, such as other antiviral agents, antibacterial agents, antifungal agents and antiparasitic agents.

Delivery Systems

The pharmaceutically acceptable carriers useful herein are conventional. *Remington's Pharmaceutical Sciences*, by Martin, Mack Publishing Co., Easton, Pa., 15th Edition (1975), describes compositions and formulations suitable for pharmaceutical delivery of the therapeutic agents herein disclosed. In general, the nature of the carrier will depend on the mode of administration being employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

Embodiments of the disclosure including medicaments can be prepared with conventional pharmaceutically acceptable carriers, adjuvants and counterions as would be known to those of skill in the art.

The amount of therapeutic agent effective in decreasing or inhibiting infection can depend on the nature of the pathogen and its associated disorder or condition, and can be determined by standard clinical techniques. Therefore, these amounts will vary depending on the type of virus, bacteria, fungus, parasite or other pathogen. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

In an example in which a nucleic acid is employed to reduce infection, such as an antisense or siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homobox-like peptide which is known to enter the nucleus (for example Joliot et al., *Proc. Natl. Acad. Sci. USA* 1991, 88:1864-8). The present disclosure includes all forms of nucleic acid delivery, including synthetic oligos, naked DNA, plasmid and viral delivery, integrated into the genome or not.

As mentioned above, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells a nucleic acid, for example an antisense molecule or siRNA. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), and pseudotyped retroviral vectors (Agrawal et al., *Exper. Hematol.* 24:738-747, 1996). Other nonpathogenic vector systems such as the foamy virus vector can also be utilized (Park et al. "Inhibition of simian immunodeficiency virus by foamy virus vectors expressing siRNAs." *Virology.* 2005 Sep. 20). It is also possible to deliver short hairpin RNAs (shRNAs) via vector delivery systems in order to inhibit gene expression (See Pichler et al. "In vivo RNA interference-mediated ablation of MDR1 P-glycoprotein." *Clin Cancer Res.* 2005 Jun. 15; 11(12):4487-94; Lee et al. "Specific inhibition of HIV-1 replication by short hairpin RNAs targeting human cyclin T1 without inducing apoptosis." *FEBS Lett.* 2005 Jun. 6; 579(14):3100-6.).

Physical transduction techniques can also be used, such as liposome delivery and receptor-mediated and other endocytosis mechanisms (see, for example, Schwartzenberger et al., *Blood* 87:472-478, 1996) to name a few examples. This invention can be used in conjunction with any of these or other commonly used gene transfer methods.

Transgenic Cells and Non-Human Mammals

The present invention also provides a non-human transgenic mammal comprising a functional deletion of ADAM10, wherein the mammal has decreased susceptibility to infection by a pathogen, such as a virus, a bacterium, a fungus or a parasite. Exemplary transgenic non-human mammals include, but are not limited to, ferrets, fish, guinea pigs, chinchilla, mice, monkeys, rabbits, rats, chickens, cows, and pigs. Such knock-out animals are useful for reducing the transmission of viruses from animals to humans. In the transgenic animals of the present invention one or both alleles of ADAM10 can be knocked out.

By "decreased susceptibility" is meant that the animal is less susceptible to infection or experiences decreased infection by a pathogen as compared to an animal that does not have one or both alleles of a ADAM10 knocked out or functionally deleted. The animal does not have to be completely resistant to the pathogen. For example, the animal can be 10%, 20%, 30%, 40%, 50%, 60%, 70%, 80%, 90%, 100% or any percentage in between less susceptible to infection by a pathogen as compared to an animal that does not have a functional deletion of ADAM10. Furthermore, decreasing infection or decreasing susceptibility to infection includes decreasing entry, replication, pathogenesis, insertion, lysis, or other steps in the replication strategy of a virus or other pathogen into a cell or subject, or combinations thereof.

Therefore, the present invention provides a non-human transgenic mammal comprising a functional deletion of ADAM10, wherein the mammal has decreased susceptibility to infection by a pathogen, such as a virus, a bacterium, a parasite or a fungus. A functional deletion is a mutation, partial or complete deletion, insertion, or other variation made to a gene sequence that inhibits production of the gene product or renders a gene product that is not completely functional or non-functional. Functional deletions can be made by insertional mutagenesis (for example via insertion of a transposon or insertional vector), by site directed mutagenesis, via chemical mutagenesis, via radiation or any other method now known or developed in the future that results in a transgenic animal with a functional deletion of ADAM10.

Alternatively, a nucleic acid sequence such as siRNA, a morpholino or another agent that interferes with ADAM10 mRNA expression can be delivered. The expression of the sequence used to knock-out or functionally delete the desired gene can be regulated by an appropriate promoter sequence. For example, constitutive promoters can be used to ensure that the functionally deleted gene is not expressed by the animal. In contrast, an inducible promoter can be used to control when the transgenic animal does or does not express the gene of interest. Exemplary inducible promoters include tissue-specific promoters and promoters responsive or unresponsive to a particular stimulus (such as light, oxygen, chemical concentration, such as a tetracycline inducible promoter).

The transgenic animals of the present invention that comprise a functionally deleted ADAM10 gene can be examined during exposure to various pathogens. Comparison data can provide insight into the life cycles of pathogens. Moreover, knock-out animals (such as birds or pigs) that are otherwise susceptible to an infection (for example influenza) can be made to resist infection, conferred by disruption of the gene. If disruption of the gene in the transgenic animal results in an increased resistance to infection, these transgenic animals can be bred to establish flocks or herds that are less susceptible to infection.

Transgenic animals, including methods of making and using transgenic animals, are described in various patents and publications, such as WO 01/43540; WO 02/19811; U.S. Pub. Nos: 2001-0044937 and 2002-0066117; and U.S. Pat. Nos. 5,859,308; 6,281,408; and 6,376,743; and the references cited therein.

The transgenic animals of this invention also include conditional gene knockdown animals produced, for example, by utilizing the SIRIUS-Cre system that combines siRNA for specific gene-knockdown, Cre-loxP for tissue-specific expression and tetracycline-on for inducible expression. These animals can be generated by mating two parental lines that contain a specific siRNA of interest gene and tissue-specific recombinase under tetracycline control. See Chang et al. "Using siRNA Technique to Generate Transgenic Animals with Spatiotemporal and Conditional Gene Knockdown." American Journal of Pathology 165: 1535-1541 (2004) which is hereby incorporated in its entirety by this reference regarding production of conditional gene knockdown animals.

The present invention also provides cells including an altered or disrupted ADAM10 that are resistant to infection by a pathogen. These cells can be in vitro, ex vivo or in vivo cells and can have one or both alleles altered. These cells can also be obtained from the transgenic animals of the present invention. Such cells therefore include cells having decreased susceptibility to HIV infection, Ebola infection, avian flu, influenza A or any of the other pathogens described herein, including bacteria, parasites and fungi.

Methods of screening agents, such as a chemical, a compound, a small or large molecule, an organic molecule, an inorganic molecule, a peptide, a drug, a protein, a cDNA, an antibody, a morpholino, a triple helix molecule, an siRNA, an shRNAs, an miRNA, an antisense nucleic acid or a ribozyme set forth using the transgenic animals described herein are also provided.

Screening for Resistance to Infection

Also provided herein are methods of screening host subjects for resistance to infection by characterizing a nucleotide sequence of a host ADAM10 nucleic acid or the amino acid sequence of a host ADAM10 polypeptide. For example, an ADAM10 nucleic acid of a subject can be isolated, sequenced, and compared to the wildtype sequence for ADAM10. The greater the similarity between that subject's ADAM10 nucleic acid and the wildtype ADAM10 sequence, the more susceptible that person is to infection, while a decrease in similarity between that subject's ADAM10 nucleic acid and the wildtype ADAM10 sequence, the more resistant that subject may be to infection. Such screens can be performed for any ADAM10 host nucleic acid or the amino acid sequence of a host ADAM10 in any species.

Assessing the genetic characteristics of a population can provide information about the susceptibility or resistance of that population to viral infection. For example, polymorphic analysis of alleles in a particular human population, such as the population of a particular city or geographic area, can indicate how susceptible that population is to infection. A higher percentage of alleles substantially similar to wild-type ADAM10 indicates that the population is more susceptible to infection, while a large number of polymorphic alleles that are substantially different than wild-type ADAM10 sequences indicates that a population is more resistant to infection. Such information can be used, for example, in making public health decisions about vaccinating susceptible populations.

The present invention also provides a method of screening a cell for a variant form of ADAM10. A variant can be a gene with a functional deletion, mutation or alteration in the gene such that the amount or activity of the gene product is altered. These cells containing a variant form of a gene can be contacted with a pathogen to determine if cells comprising a naturally occurring variant of ADAM10 differ in their resistance to infection. For example, cells from an animal, for example, a chicken, can be screened for a variant form of ADAM10. If a naturally occurring variant is found and chickens possessing a variant form of the gene in their genome are less susceptible to infection, these chickens can be selectively bred to establish flocks that are resistant to infection. By utilizing these methods flocks of chickens that are resistant to avian flu can be established. Similarly, other animals can be screened for a variant form of a gene ADAM10. If a naturally occurring variant is found and animals possessing a variant form of the gene in their genome are less susceptible to infection, these animals can be selectively bred to establish populations that are resistant to infection. These animals include, but are not limited to, cats, dogs, livestock (for example, cattle, horses, pigs, sheep, goats, etc.), laboratory animals (for example, mouse, monkey, rabbit, rat, gerbil, guinea pig, etc.) and avian species (for example, flocks of chickens, geese. turkeys, ducks, pheasants, pigeons, doves etc.). Therefore, the present application provides populations of animals that comprise a naturally occurring variant of ADAM10 that results in decreased susceptibility to viral infection, thus providing populations of animals that are less susceptible to viral infection. Similarly, if a naturally occurring variant is found and animals possessing a variant form of the gene in their genome are less susceptible to bacterial, parasitic or fungal infection, these animals can be selectively bred to establish populations that are resistant to bacterial, parasitic or fungal infection.

The following examples are put forth so as to provide those of ordinary skill in the art with a complete disclosure and description of how the antibodies, polypeptides, nucleic acids, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

EXAMPLES

Inhibition of HIV Replication with siRNA Targeting the Metalloproteinase ADAM10

In order to determine if siRNA targeting the metalloprotease ADAM10 inhibits infection, JC53 HeLa cells were transfected with siRNAs targeting either ERBB2IP or ADAM10 for 48 hours to allow sufficient time for target gene silencing prior to infection with HIV-1. As stated above JC53 cells are also known as TZM-b1 cells. The siRNAs utilized to target ERBB2IP were as follows:

```
                       (SEQ ID NO: 61)
Duplex #1, Sense:      UGAAACAGCUCACAUAUUUUU
                       (SEQ ID NO: 62)
Duplex #1, Antisense:  AAAUAUGUGAGGUGUUUCAUU (SEQ ID NO: 63)
Duplex #2, Sense:      UGUGAAAUCUCAUAGCAUAUU
                       (SEQ ID NO: 64)
Duplex #2, Antisense:  UAUGCUAUGAGAUUUCACAUU (SEQ ID NO: 65)
Duplex #3, Sense:      CGAAGAGCCAAAUAUAAUAUU
                       (SEQ ID NO: 66)
Duplex #3, Antisense:  UAUUAUAUUUGGCUCUUCGUU (SEQ ID NO: 67)
Duplex #4, Sense:      CCAAACGACCGACUUAUUCUU
                       (SEQ ID NO: 68)
Duplex #4, Antisense:  GAAUAAGUCGGUCGUUUGGUU
```

The siRNA sequence utilized to target ADAM10 were as follows:

```
                       (SEQ ID NO: 53)
Duplex #1, Sense:      GCUAAUGGCUGGAUUUAUUUU
                       (SEQ ID NO: 54)
Duplex #1, Antisense:  AAUAAAUCCAGCCAUUAGCUU (SEQ ID NO: 55)
Duplex #2, Sense:      GGACAAACUUAACAACAAUUU
                       (SEQ ID NO: 56)
Duplex #2, Antisense:  AUUGUUGUUAAGUUUGUCCUU (SEQ ID NO: 57)
Duplex #3, Sense:      CCCAAAGUCUCUCACAUUAUU
                       (SEQ ID NO: 58)
Duplex #3, Antisense:  UAAUGUGAGAGACUUUGGGUU (SEQ ID NO: 59)
Duplex #4, Sense:      GCAAGGGAAGGAAUAUGUAUU
                       (SEQ ID NO: 60)
Duplex #4, Antisense:  UACAUAUUCCUUCCCUUGCUU
```

Following transfection, cells were infected overnight with the LAV strain of HIV-1 (using a multiplicity of infection of 1). The next day, cells were washed to remove the inoculum and expanded in duplicate T75 flasks. HIV replication was quantitated by performing HIV p24 ELISA assays using culture supernatants harvested the indicated siRNA transfectants 3 days following the infection period. Values were normalized to HIV p24 secretion from ERBB2IP siRNA-transfected cells, and represent the results of 4 independent experiments. Values are normalized to ERBB2IP since it is not involved in HIV infection. FIG. 1 shows the relative amount of HIV replication HIV-infected cells in the presence of siRNAs targeting either ERBB2IP or ADAM10. As shown in FIG. 1, upon silencing ADAM10, a significant reduction in HIV replication is observed.

Figure 2A:
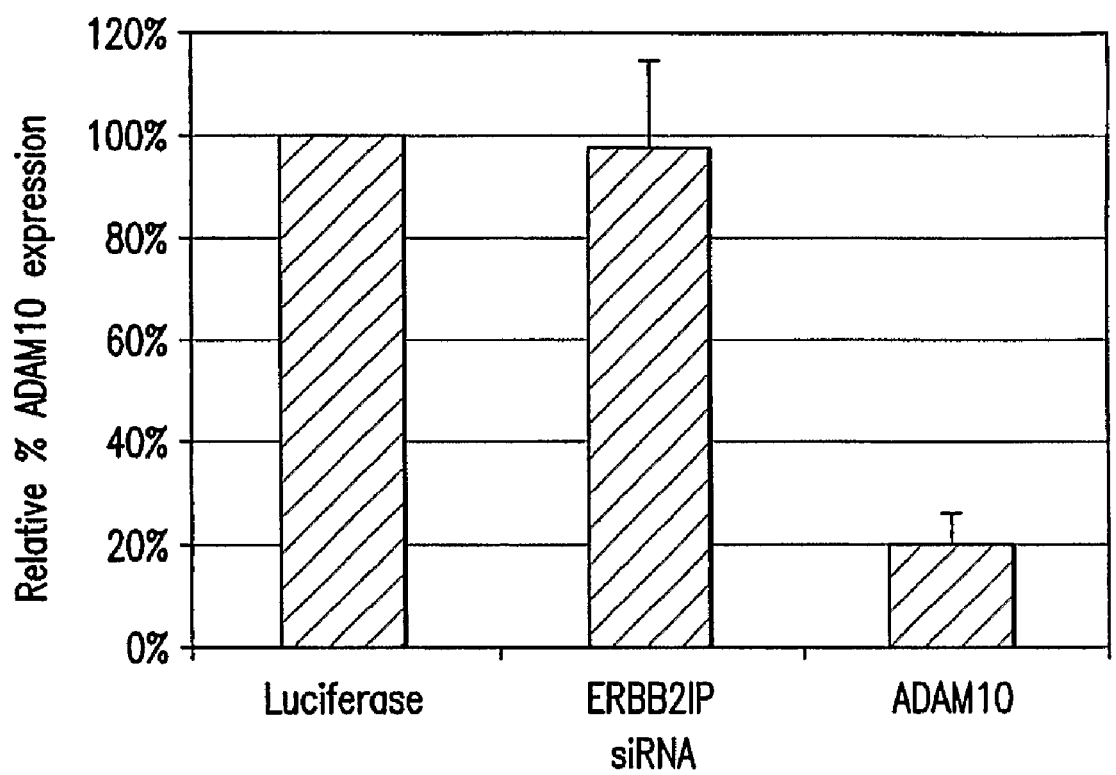
FIG. 2A shows that ADAM10 mRNA expression is inhibited in JC53 cells transfected with ADAM10 siRNA. JC53 cells are also known as TZM-b1 cells, originally from Transzyme, Inc., but now available through the HIV-AIDS repository.
Figure 2B:
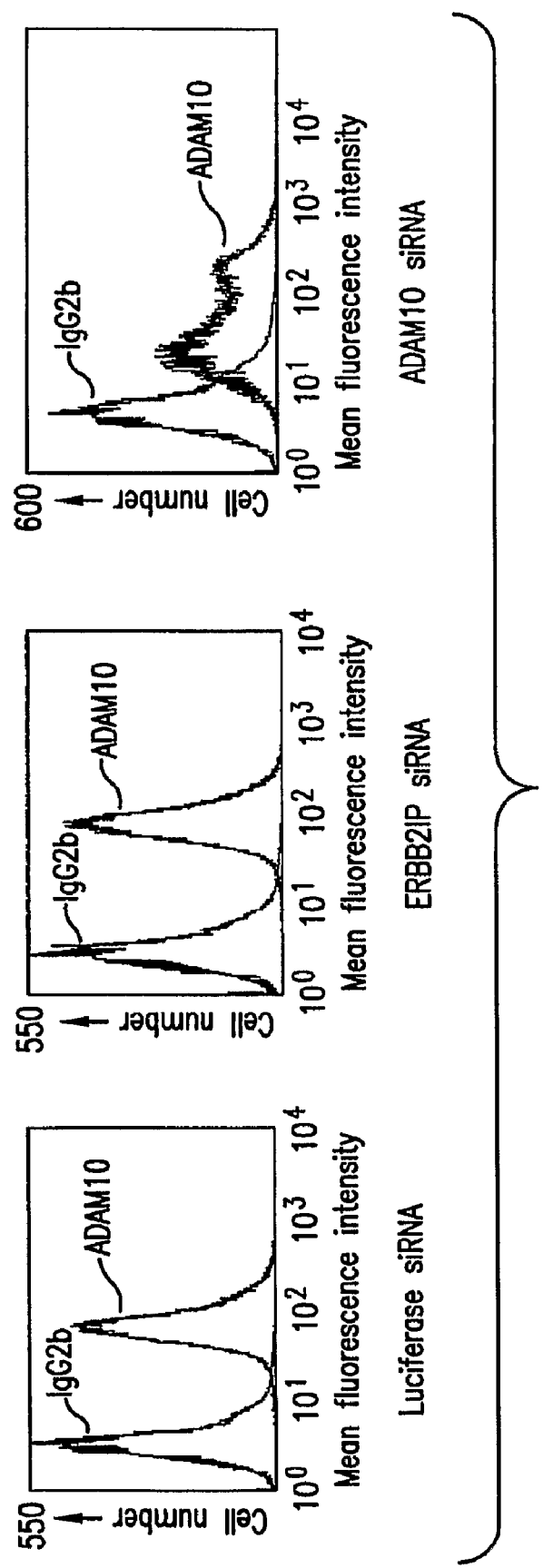
FIG. 2B shows cytometric analysis of cell surface ADAM10 protein expression following the indicated siRNA transfections.

Inhibition ADAM10 mRNA and Protein Expression in JC53 Cells Transfected with ADAM10 siRNA FIG. 2 shows that (A) JC53 cells were transfected with siRNAs targeting an irrelevant target mRNA (luciferase), or the host proteins ERBB2IP or ADAM10, as indicated. Two days post-transfection, total RNA was isolated and reverse transcribed using random hexamers to prime the first strand cDNA synthesis reaction. Relative levels of ADAM10 mRNA expression originally present in transfected cells were detected by real time PCR, and normalized to HPRT expression (n=4). (B) Flow cytometric analysis of cell surface ADAM10 protein expression following the indicated siRNA transfections. Staining was performed using a mouse anti-Rab9 antibody or a mouse IgG2b negative control, and a secondary goat anti-mouse antibody conjugated to phycoerythrin. Following transfection, 57% of cells transfected with ADAM10 siRNA displayed a 78% decrease in mean fluorescence intensity.

Inhibition of HIV Replication with siRNA Targeting ADAM10 and No Inhibition of HIV Replication with siRNA Targeting ADAM17

In order to determine if siRNA targeting the metalloprotease ADAM10 inhibits infection, JC53 HeLa cells were transfected with siRNAs targeting either ERBB2IP or ADAM10 or ADAM17 for 48 hours to allow sufficient time for target gene silencing prior to infection with HIV-1. The sequences utilized to target ADAM10 or ERBB2IP are set forth above. The sequences utilized to target ADAM17 are as follows:

```
                       (SEQ ID NO: 69)
Duplex #1, Sense:      GAACACGUGUAAAUUAUUGUU
                       (SEQ ID NO: 70)
Duplex #1, Antisense:  CAAUAAUUUACACGUGUUCUU (SEQ ID NO: 71)
Duplex #2, Sense:      GAUCAUCGCUUCUACAGAUUU
                       (SEQ ID NO: 72)
Duplex #2, Antisense:  AUCUGUAGAAGCGAUGAUCUU (SEQ ID NO: 73)
Duplex #3, Sense:      UAUGGGAACUCUUGGAUUAUU
                       (SEQ ID NO: 74)
Duplex #3, Antisense:  UAAUCCAAGAGUUCCCAUAUU (SEQ ID NO: 75)
Duplex #4, Sense:      GAGGAAGCAUCUAAAGUUUUU
                       (SEQ ID NO: 76)
Duplex #4, Antisense:  AAACUUUAGAUGCUUCCUCUU
```

Figure 3:
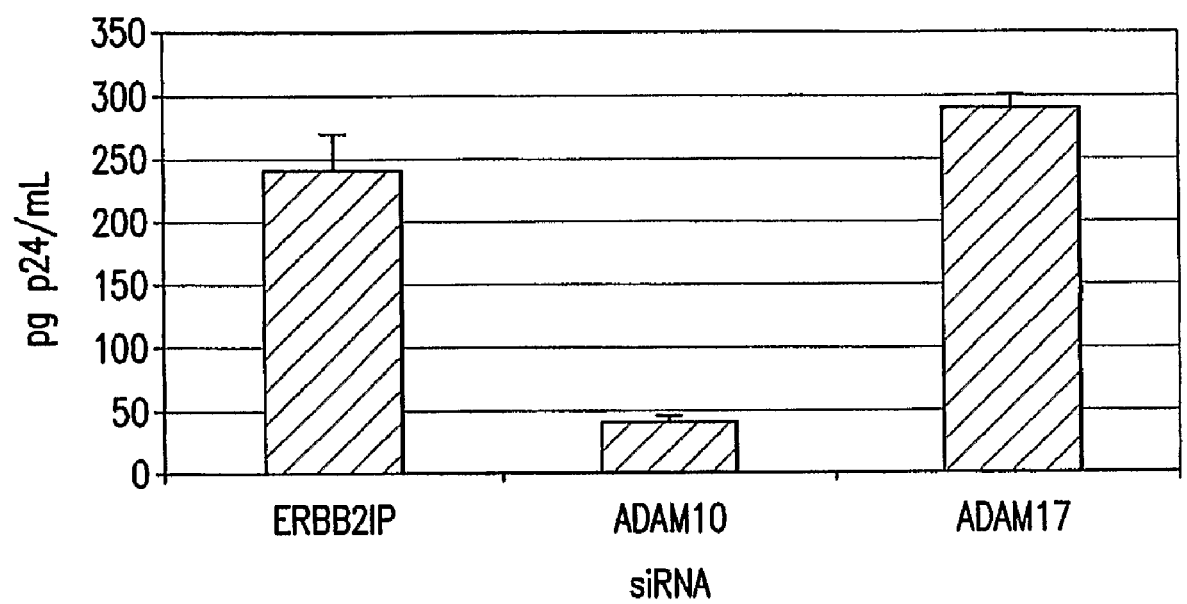
FIG. 3 shows that siRNA targeting ADAM10 inhibits HIV replication, but siRNA targeting ADAM17 does not inhibit HIV replication.

Following transfection, cells were infected overnight with the LAV strain of HIV-1 (using a multiplicity of infection of 1). The next day, cells were washed to remove the inoculum and expanded in duplicate T75 flasks. HIV replication was quantitated by performing HIV p24 ELISA assays using culture supernatants harvested the indicated siRNA transfectants 3 days following the infection period. Values were normalized to HIV p24 secretion from ERBB2IP siRNA-transfected cells, and represent the results of 4 independent experiments. Values are normalized to ERBB2IP since it is not involved in HIV infection. FIG. 3 shows the relative amount of HIV replication HIV-infected cells in the presence of siRNAs targeting ERBB2IP, ADAM10, or ADAM17. As shown in FIG. 3, upon silencing ADAM10, a significant reduction in HIV replication is observed. However upon silencing ADAM17, no inhibition of HIV replication is observed relative to control cells containing siRNA that silences ERBB2IP expression. Utilizing the methods of the present invention, inhibition of HIV infection in macrophages was also observed.

Throughout this application, various publications are referenced. The disclosures of these publications in their entireties are hereby incorporated by reference into this application in order to more fully describe the state of the art to which this invention pertains.

What is claimed is:

1. A method of decreasing infection in a cell by Human Immunodeficiency Virus comprising decreasing expression or activity of ADAM10, wherein the expression or activity of ADM10 is decreased by contacting the cell within a composition comprising a compound of structure formula:

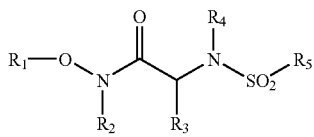

or a pharmaceutically acceptable salt thereof, wherein $R_1$ is selected from hydrogen, alkyl, alkanoyl, arylalkyl, and arylalkanoyl, wherein the arylalkyl and arylalkanoyl groups are unsubstituted or substituted with 1, 2, 3, 4, or 5 $R_6$ groups;

$R_6$ at each occurrence is independently selected from halogen, hydroxy, —$NO_2$, —$CO_2R_{10}$, —CN, alkyl, alkoxy, haloalkyl, and haloalkoxy;

R2 is selected from hydrogen, alkyl, alkoxy, alkanoyl, arylalkyl and arylalkanoyl, wherein the arylalkyl and arylalkanoyl groups are unsubstituted or substituted with 1, 2, 3, 4, or 5 $R_6$ groups;

$R_3$ is —Z-Q-J, wherein

Z is selected from alkyl, alkoxyalkyl, alkylthioalkyl, and alkenyl, each of which is unsubstituted or substituted with 1 or 2 groups that are independently selected from alkoxy, hydroxy, and halogen;

Q is selected from a direct bond between Z and J, —C(=O)—, aryl, heteroaryl, and heterocycloalkyl, wherein the aryl, heteroaryl, or heterocycloalkyl group is unsubstituted or substituted with 1 or 2 groups that are independently selected from alkyl, halogen, —$NR_8R_9$, and alkoxy;

J is selected from —$NR_8R_9$, —$NR_7C(=O)NR_8R_9$, —$NR_7C(=O)$ alkyl$NR_8R_9$, —$NR_7C(=O)OR_9$, —$C(=NR_7)$ $NR_8R_9$, and —NH—$C(=NR7)NR_8R_9$, wherein R7 is selected from H, CN, NO2, alkyl, alkanoyl, arylalkanoyl and —$C(=O)NR_{10}R_{11}$, wherein $R_{10}$ and $R_{11}$ are independently selected from H, and alkyl, and $R_8$ and $R_9$ are independently selected from H, alkyl, hydroxy, alkoxy, alkoxyalkyl, heterocycloalkylalkyl, aryylalkyl, and heteroarylalkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently selected from alkyl, alkoxy, hydroxy, and halogen; or $R_7$, $R_8$, and the nitrogens to which they are attached form a 5, 6 or 7 membered heterocycloalkyl group that is unsubstituted or substituted with 1, 2 or 3 groups that are independently selected from alkyl, alkoxy, hydroxy, and halogen; and $R_9$ is selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups;

$R_4$ is selected from H, alkyl, and arylalkyl, wherein the arylalkyl group is unsubstituted or substituted with 1, 2, 3, 4, or 5 $R_6$ groups; and $R_5$ is -M-G-A, wherein M is selected from aryl and heteroaryl, wherein M is unsubstituted or substituted with 1, 2, 3, or 4 groups that are independently selected from halogen, alkyl, hydroxy, alkoxy, haloalkyl, —CN, haloalkoxy, and hydroxyalkyl;

G is selected from a direct bond between M and A, CH2, -alkyl-O—, —O-alkyl-, O, S, SO, and $SO_2$;

A is selected from aryl and heteroaryl, wherein A is unsubstituted or substituted with 1, 2, 3, 4, or 5 groups that are independently selected from halogen, alkyl, alkoxy, haloalkyl, aryloxy, heteroaryloxy, arylalkoxy, heteroarylalkoxy, haloalkoxy, —CN, and $NO_2$;

with the proviso that when M is phenyl, G is a direct bond between M and A, and A is phenyl, then at least one of the four remaining hydrogens on the phenyl ring of M, of M-G-A, must be substituted with a group independently selected from halogen, alkyl, hydroxy, alkoxy, haloalkyl, —CN, haloalkoxy, and hydroxyalkyl.

2. The method of claim 1, wherein the composition comprises $N^2$-{[3,5-difluoro-4-(phenyloxy)phenyl]sulfonyl}-$N^1$-hydroxy-D-argininamide or a pharmaceutically acceptable salt thereof.

3. The method of claim 1, wherein the cell is in an in vitro, ex vivo or an in vivo cell.

4. The method of claim 1, wherein the cell is present in a subject.

* * * * *

SEQUENCE LISTING

<160> NUMBER OF SEQ ID NOS: 80

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence; note = synthetic construct

<400> SEQUENCE: 1
gcugaugaga aggacccua                                                19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence; note = synthetic construct

<400> SEQUENCE: 2
uaggguccuu cucaucagc                                                19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence; note = synthetic construct

<400> SEQUENCE: 3
ggucucaugu accucccaa                                                19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence; note = synthetic construct

<400> SEQUENCE: 4
uugggaggua caugagacc                                                19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence; note = synthetic construct

<400> SEQUENCE: 5
gcucacgaag uuggacaua                                                19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence; note = synthetic construct

<400> SEQUENCE: 6

```
uauguccaac uucgugagc                                          19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 7
gcacaccagg agaaucuaa                                          19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 8
uuagauucuc cuggugugc                                          19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 9
ccaggagaau cuaagaauu                                          19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 10
aauucuuaga uucuccugg                                          19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 11
ccaaccuauu uguggaaau                                          19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 12
auuuccacaa auagguugg                                          19
```

```
<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 13
gggaaacagu gcaguccaa                                                    19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 14
uuggacugca cuguuccc                                                     19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 15
gcugaugguc cucuagcua                                                    19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 16
uagcuagagg accaucagc                                                    19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 17
gcucauuggu gggcaguau                                                    19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 18
auacugccca ccaaugagc                                                    19

<210> SEQ ID NO 19
```

```
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 19
gcuaauggcu ggauuuauu                                                  19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 20
aauaaaucca gccauuagc                                                  19

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 21
caccgctgat gagaaggacc ctacgaatag ggtccttctc atcagc                    46

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 22
aaaagctgat gagaaggacc ctattcgtag ggtccttctc atcagc                    46

<210> SEQ ID NO 23
<211> LENGTH: 46
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 23
caccgctgat gagaaggacc ctacgaatag ggtccttctc atcagc                    46

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 24
cgactactct tcctgggatg cttatcccag gaagagtagt cgaaaa                    46

<210> SEQ ID NO 25
<211> LENGTH: 20
<212> TYPE: DNA
```

```
<213> ORGANISM: Artificial Sequence
<220> FEATURE:
<223> OTHER INFORMATION: Description of Artificial Sequence; note =
      synthetic construct

<400> SEQUENCE: 25
tccttcctca ccacgtgacg                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 26
ggcaggagaa acggcgaagc                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 27
gtcttcatgt gagactgctc                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 28
ctacaccagt catctggtat                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 29
ttctcatcag cagttgtatt                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 30
cagcattcat ctttacactg                                                   20

<210> SEQ ID NO 31
<211> LENGTH: 20
<212> TYPE: DNA
<213> ORGANISM: Artificial Sequence
<220> FEATURE:
```

```
<223> OTHER INFORMATION: Description of Artificial Sequence; note =
      synthetic construct

<400> SEQUENCE: 31
cataattctt tatcatcttt                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 32
catcacagta acctctaaaa                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 33
agcaattccc ataagtaata                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 34
gtgaagtttt cccattgtag                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 35
ggtctgagga tatgatctct                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 36
tacatgtctg catataacaa                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct
```

<400> SEQUENCE: 37
tgtttacaat tgcacacaga					20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 38
gagtatgtca attaaacagt					20

<210> SEQ ID NO 39
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 39
tgctgtatct gggcaatcac agcttcgttt tggccactga ctgacgaagc tgtttgccca	60 gata							64

<210> SEQ ID NO 40
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 40
cctgtatctg gcaaacagc ttcgtcagtc agtggccaaa acgaagctgt gattgcccag	60 atac							64

<210> SEQ ID NO 41
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 41
tgctgtatct gggcaatcac agcttcgttt tggccactga ctgacgaagc tgtttgccca	60 gata							64

<210> SEQ ID NO 42
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 42
catagacccg ttagtgtcga agcaaaaccg gtgactgact gcttcgacaa acgggtctat	60 gtcc							64

<210> SEQ ID NO 43

```
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 43
tgctgatatt tgggaaacgg aaaggagttt tggccactga ctgactcctt tccttcccaa      60
atat                                                                  64

<210> SEQ ID NO 44
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 44
cctgatattt gggaaggaaa ggagtcagtc agtggccaaa actcctttcc gtttcccaaa      60
tatc                                                                  64

<210> SEQ ID NO 45
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 45
tgctgatatt tgggaaacgg aaaggagttt tggccactga ctgactcctt tccttcccaa      60
atat                                                                  64

<210> SEQ ID NO 46
<211> LENGTH: 64
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 46
ctataaaccc tttgcctttc ctcaaaaccg gtgactgact gaggaaagga agggtttata      60
gtcc                                                                  64

<210> SEQ ID NO 47
<211> LENGTH: 46
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 47
ucggucugug aacugaugag uccgugagga cgaaacauag gccaaa                    46

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence; note =
      synthetic construct
```

```
<400> SEQUENCE: 48
uuuggccuau gucuucacag accga                                          25

<210> SEQ ID NO 49
<211> LENGTH: 46
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 49
cauagagcuc ugcugaugag uccgugagga cgaaacuaaa aauugc                   46

<210> SEQ ID NO 50
<211> LENGTH: 25
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 50
gcaauuuuua guccagagcu cuaug                                          25

<210> SEQ ID NO 51
<211> LENGTH: 46
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 51
ccaguguuua agcugaugag uccgugagga cgaaacuucu ucuuac                   46

<210> SEQ ID NO 52
<211> LENGTH: 25
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 52
guaagaagaa guccuuaaac acugg                                          25

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 53
gcuaauggcu ggauuuauuu u                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 54
```
aauaaaucca gccauuagcu u    21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 55
ggacaaacuu aacaacaauu u    21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 56
auuguuguua aguuuguccu u    21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 57
cccaaagucu cucacauuau u    21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 58
uaaugugaga gacuuugggu u    21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 59
gcaagggaag gaauauguau u    21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 60
uacauauucc uucccuugcu u    21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 61
ugaaacagcu cacauauuuu u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 62
aaauauguga gcuguuucau u                                              21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 63
ugugaaaucu cauagcauau u                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 64
uaugcuauga gauuucacau u                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 65
cgaagagcca aauauaauau u                                              21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 66
uauuauauuu ggcucuucgu u                                              21

<210> SEQ ID NO 67

```
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 67
ccaaacgacc gacuuauucu u                                              21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 68
gaauaagucg gucguuuggu u                                              21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 69
gaacacgugu aaauuauugu u                                              21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 70
caauaauuua cacguguucu u                                              21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 71
gaucaucgcu ucuacagauu u                                              21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 72
aucuguagaa gcgaugaucu u                                              21

<210> SEQ ID NO 73
<211> LENGTH: 21
<212> TYPE: RNA
```

<213> ORGANISM: Artificial Sequence
<220> FEATURE:
<223> OTHER INFORMATION: Description of Artificial Sequence; note = synthetic construct

<400> SEQUENCE: 73
uaugggaacu cuuggauuau u                                        21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 74
uaauccaaga guucccauau u                                        21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 75
gaggaagcau cuaaaguuuu u                                        21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence; note = synthetic construct

<400> SEQUENCE: 76
aaacuuuaga ugcuuccucu u                                        21

<210> SEQ ID NO 77
<211> LENGTH: 3927
<212> TYPE: DNA
<213> ORGANISM: Artificial Sequence
<220> FEATURE:
<223> OTHER INFORMATION: Description of Artificial Sequence; note = synthetic construct

<400> SEQUENCE: 77
gcggcggcag gcctagcagc acgggaaccg tcccccgcgc gcatgcgcgc gccccctgaag      60 cgcctggggg acgggtatgg gcgggaggta gggcgcggc tccgcgtgcc agttgggtgc      120
ccgcgcgtca cgtggtgagg aaggaggcgg aggtctgagt ttcgaaggag gggggagag      180 aagagggaac gagcaaggga aggaaagcgg ggaaggagg aaggaaacga acgaggggga      240
gggaggtccc tgttttggag gagctaggag cgttgccggc ccctgaagtg gagcgagagg      300
gaggtgcttc gccgtttctc ctgccagggg aggtcccggc ttcccgtgga ggctccggac      360
caagcccctt cagcttctcc ctccggatcg atgtgctgct gttaacccgt gaggaggcgg      420
cggcggcggc agcggcagcg gaagatggtg ttgctgagag tgttaattct gctcctctcc      480
tgggcggcgg ggatgggagg tcagtatggg aatccttaa ataaatatat cagacattat      540
gaaggattat cttacaatgt ggattcatta caccaaaaac accagcgtgc caaaagagca      600
gtctcacatg aagaccaatt tttacgtcta gatttccatg cccatggaag acatttcaac      660

-continued

```
ctacgaatga agagggacac ttcccttttc agtgatgaat ttaaagtaga aacatcaaat    720
aaagtacttg attatgatac ctctcatatt tacactggac atatttatgg tgaagaagga    780
agttttagcc atgggtctgt tattgatgga agatttgaag gattcatcca gactcgtggt    840
ggcacatttt atgttgagcc agcagagaga tatattaaag accgaactct gccatttcac    900
tctgtcattt atcatgaaga tgatattaac tatccccata aatacggtcc tcagggggc     960 tgtgcagatc attcagtatt tgaaagaatg aggaaatacc agatgactgg tgtagaggaa   1020
gtaacacaga tacctcaaga agaacatgct gctaatggtc cagaacttct gaggaaaaaa   1080
cgtacaactt cagctgaaaa aaatacttgt cagctttata ttcagactga tcatttgttc   1140
tttaaatatt acggaacacg agaagctgtg attgcccaga tatccagtca tgttaaagcg   1200
attgatacaa tttaccagac cacagacttc tccggaatcc gtaacatcag tttcatggtg   1260
aaacgcataa gaatcaatac aactgctgat gagaaggacc ctacaaatcc tttccgtttc   1320
ccaaatattg gtgtggagaa gtttctggaa ttgaattctg agcagaatca tgatgactac   1380
tgtttggcct atgtcttcac agaccgagat tttgatgatg cgtacttgg tctggcttgg    1440 gttggagcac cttcaggaag ctctggagga atatgtgaaa aaagtaaact ctattcagat   1500
ggtaagaaga agtccttaaa cactggaatt attactgttc agaactatgg gtctcatgta   1560
cctcccaaag tctctcacat tacttttgct cacgaagttg acataacttt ggatcccca    1620 catgattctg gaacagagtg cacaccagga gaatctaaga atttgggtca aaagaaat    1680 ggcaattaca tcatgtatgc aagagcaaca tctggggaca aacttaacaa caataaattc   1740
tcactctgta gtattagaaa tataagccaa gttcttgaga agaagagaaa caactgtttt   1800
gttgaatctg ccaacctat ttgtggaaat ggaatggtag aacaaggtga agaatgtgat   1860
tgtggctata gtgaccagtg taaagatgaa tgctgcttcg atgcaaatca accagaggga   1920
agaaaatgca aactgaaacc tgggaaacag tgcagtccaa gtcaaggtcc ttgttgtaca   1980
gcacagtgtg cattcaagtc aaagtctgag aagtgtcggg atgattcaga ctgtgcaagg   2040
gaaggaatat gtaatggctt cacagctctc tgcccagcat ctgaccctaa accaaacttc   2100
acagactgta ataggcatac acaagtgtgc attaatgggc aatgtgcagg ttctatctgt   2160
gagaaatatg gcttagagga gtgtacgtgt gccagttctg atggcaaaga tgataaagaa   2220
ttatgccatg tatgctgtat gaagaaaatg gacccatcaa cttgtgccag tacagggtct   2280
gtgcagtgga gtaggcactt cagtggtcga accatcaccc tgcaacctgg atccccttgc   2340
aacgatttta gaggttactg tgatgttttc atgcggtgca gattagtaga tgctgatggt   2400
cctctagcta ggcttaaaaa agcaatttt agtccagagc tctatgaaaa cattgctgaa   2460
tggattgtgg ctcattggtg ggcagtatta cttatgggaa ttgctctgat catgctaatg   2520
gctggattta ttaagatatg cagtgttcat actccaagta gtaatccaaa gttgcctcct   2580
cctaaaccac ttccaggcac tttaaagagg aggagacctc acagcccat tcagcaaccc   2640 cagcgtcagc ggccccgaga gagttatcaa atgggacaca tgagacgcta actgcagctt   2700
ttgccttggt tcttcctagt gcctacaatg ggaaaacttc actccaaaga gaaacctatt   2760
aagtcatcat ctccaaacta aaccctcaca gtaacagtt gaagaaaaaa tggcaagaga   2820
tcatatcctc agaccaggtg gaattactta aatttttaaag cctgaaaatt ccaatttggg   2880
ggtgggaggt ggaaaaggaa cccaattttc ttatgaacag atattttta cttaatggca   2940 caaagtctta gaatattatt atgtgccccg tgttccctgt tcttcgttgc tgcatttct    3000 tcacttgcag gcaaacttgg ctctcaataa acttttacca caaattgaaa taaatatatt   3060
```

| | |
|---|---|
| tttttcaact gccaatcaag gctaggaggc tcgaccacct caacattgga gacatcactt | 3120 |
| gccaatgtac ataccttgtt atatgcagac atgtatttct tacgtacact gtacttctgt | 3180 |
| gtgcaattgt aaacagaaat tgcaatatgg atgtttcttt gtattataaa attttccgc | 3240 |
| tcttaattaa aaattactgt ttaattgaca tactcaggat aacagagaat ggtggtattc | 3300 |
| agtggtccag gattctgtaa tgctttacac aggcagtttt gaaatgaaaa tcaatttacc | 3360 |
| tttctgttac gatggagttg gttttgatac tcattttttc tttatcacat ggctgctacg | 3420 |
| ggcacaagtg actatactga agaacacagt taagtgttgt gcaaactgga catagcagca | 3480 |
| catactactt cagagttcat gatgtagatg tctggtttct gcttacgtct tttaaacttt | 3540 |
| ctaattcaat tccattttc aattaatagg tgaaatttta ttcatgcttt gatagaaatt | 3600 |
| atgtcaatga aatgattctt tttatttgta gcctacttat ttgtgttttt catatatctg | 3660 |
| aaatatgcta attatgtttt ctgtctgata tggaaaagaa aagctgtgtc tttatcaaaa | 3720 |
| tatttaaacg gttttttcag catatcatca ctgatcattg gtaaccacta agatgagta | 3780 |
| atttgcttaa gtagtagtta aaattgtaga taggccttct gacattttt ttcctaaaat | 3840 |
| ttttaacagc attgaaggtg aaacagcaca atgtcccatt ccaaatttat ttttgaaaca | 3900 |
| gatgtaaata attggcattt taaagag | 3927 |

<210> SEQ ID NO 78
<211> LENGTH: 3410
<212> TYPE: DNA
<213> ORGANISM: Artificial Sequence
<220> FEATURE:
<223> OTHER INFORMATION: Description of Artificial Sequence; note = synthetic construct

<400> SEQUENCE: 78

| | |
|---|---|
| gaattcgagg atccgggtac catgggcggc ggcaggccta gcagcacggg aaccgtcccc | 60 |
| cgcgcgcatg cgcgcgcccc tgaagcgcct ggggacggg tatgggcggg aggtaggggc | 120 |
| gcggctccgc gtgccagttg ggtgcccgcg cgtcacgtgg tgaggaagga ggcggaggtc | 180 |
| tgagtttcga gggaggggggg gagagaagag ggaacgagca agggaaggaa agcggggaaa | 240 |
| ggaggaagga acgaacgag ggggagggag gtccctgttt tggaggagct aggagcgttg | 300 |
| ccggcccctg aagtggagcg agagggaggt gcttcgccgt ttctcctgcc aggggaggtc | 360 |
| ccggcttccc gtggaggctc cggaccaagc cccttcagct tctccctccg gatcgatgtg | 420 |
| ctgctgttaa cccgtgagga ggcggcgcg gcggcagcgg cagcggaaga tggtgttgct | 480 |
| gagagtgtta attctgctcc tctcctgggc ggcggggatg ggaggtcagt atgggaatcc | 540 |
| tttaaataaa tatatcagac attatgaagg attatcttac aatgtggatt cattacacca | 600 |
| aaaacaccag cgtgccaaaa gagcagtctc acatgaagac caatttttac gtctagattt | 660 |
| ccatgcccat ggaagacatt tcaacctacg aatgaagagg acacttccc ttttcagtga | 720 |
| tgaatttaaa gtagaaacat caaataaagt acttgattat gatacctctc atatttacac | 780 |
| tggacatatt tatggtgaag aaggaagttt tagccatggg tctgttattg atggaagatt | 840 |
| tgaaggattc atccagactc gtggtggcac attttatgtt gagccagcag agagatatat | 900 |
| taaagaccga actctgccat ttcactctgt catttatcat gaagatgata ttaactatcc | 960 |
| ccataaatac ggtcctcagg ggggctgtgc agatcattca gtatttgaaa gaatgaggaa | 1020 |
| ataccagatg actggtgtag aggaagtaac acagatacct caagaagaac atgctgctaa | 1080 |
| tggtccagaa cttctgagga aaaacgtac aacttcagct gaaaaaaata cttgtcagct | 1140 |

-continued

```
ttatattcag actgatcatt tgttctttaa atattacgga acacgagaag ctgtgattgc      1200
ccagatatcc agtcatgtta aagcgattga tacaatttac cagaccacag acttctccgg      1260
aatccgtaac atcagtttca tggtgaaacg cataagaatc aatacaactg ctgatgagaa      1320
ggaccctaca aatcctttcc gtttcccaaa tattggtgtg gagaagtttc tggaattgaa      1380
ttctgagcag aatcatgatg actactgttt ggcctatgtc ttcacagacc gagattttga      1440
tgatggcgta cttggtctgg cttgggttgg agcaccttca ggaagctctg gaggaatatg      1500 tgaaaaagt aaactctatt cagatggtaa gaagaagtcc ttaaacactg gaattattac       1560
tgttcagaac tatgggtctc atgtacctcc caaagtctct cacattactt ttgctcacga      1620
agttggacat aactttggat ccccacatga ttctggaaca gagtgcacac caggagaatc      1680
taagaatttg ggtcaaaaag aaaatggcaa ttacatcatg tatgcaagag caacatctgg      1740
ggacaaactt aacaacaata aattctcact ctgtagtatt agaaatataa gccaagttct      1800
tgagaagaag agaaacaact gttttgttga atctggccaa cctatttgtg gaaatggaat      1860
ggtagaacaa ggtgaagaat gtgattgtgg ctatagtgac cagtgtaaag atgaatgctg      1920
cttcgatgca aatcaaccag agggaagaaa atgcaaactg aaacctggga acagtgcag       1980 tccaagtcaa ggtccttgtt gtacagcaca gtgtgcattc aagtcaaagt ctgagaagtg      2040 tcggatgat tcagactgtg caagggaagg aatatgtaat ggcttcacag ctctctgccc       2100
agcatctgac cctaaaccaa acttcacaga ctgtaatagg catacacaag tgtgcattaa      2160
tgggcaatgt gcaggttcta tctgtgagaa atatggctta gaggagtgta cgtgtgccag      2220
ttctgatggc aaagatgata agaattatg ccatgtatgc tgtatgaaga aaatggaccc       2280
atcaacttgt gccagtacag ggtctgtgca gtggagtagg cacttcagtg gtcgaaccat      2340
caccctgcaa cctggatccc cttgcaacga ttttagaggt tactgtgatg ttttcatgcg      2400
gtgcagatta gtagatgctg atggtcctct agctaggctt aaaaaagcaa tttttagtcc      2460
agagctctat gaaaacattg ctgaatggat tgtggctcat tggtgggcag tattacttat      2520
gggaattgct ctgatcatgc taatggctgg atttattaag atatgcagtg ttcatactcc      2580
aagtagtaat ccaaagttgc ctcctcctaa accacttcca ggcactttaa agaggaggag      2640
acctccacag cccattcagc aaccccagcg tcagcggccc cgagagagtt atcaaatggg      2700
acacatgaga cgctaactgc agcttttgcc ttggttcttc ctagtgccta caatgggaaa      2760
acttcactcc aaagagaaac ctattaagtc atcatctcca aactaaaccc tcacaagtaa      2820
cagttgaaga aaaaatggca agagatcata tcctcagacc aggtggaatt acttaaattt      2880
taaagcctga aaattccaat ttgggggtgg gaggtggaaa aggaacccaa ttttcttatg      2940
aacagatatt tttaacttaa tggcacaaag tcttagaata ttattatgtg ccccgtgttc      3000
cctgttcttc gttgctgcat tttcttcact tgcaggcaaa cttggctctc aataaacttt      3060
taccacaaat tgaaataaat atatttttt caactgccaa tcaaggctag gaggctcgac       3120 caccctcaaca ttggagacat cacttgccaa tgtacatacc ttgttatatg cagacatgta     3180
tttcttacgt acactgtact tctgtgtgca attgtaaaca gaaattgcaa tatgatgtt       3240 tctttgtatt ataaaattt tccgctctta attaaaaatt actgtttaat tgacatactc       3300
aggataacag agaatggtgg tattcagtgg tccaggattc tgtaatgctt tacacaggca      3360
gttttgaaat gaaaatcaat ttaccccatg gtacccggat cctcgaattc                 3410
```

<210> SEQ ID NO 79
<211> LENGTH: 748
<212> TYPE: PRT

<213> ORGANISM: Artificial Sequence
<220> FEATURE:
<223> OTHER INFORMATION: Description of Artificial Sequence; note = synthetic construct

<400> SEQUENCE: 79

```
Met Val Leu Leu Arg Val Leu Ile Leu Leu Ser Trp Ala Ala Gly
 1               5                   10                  15

Met Gly Gly Gln Tyr Gly Asn Pro Leu Asn Lys Tyr Ile Arg His Tyr
                20                  25                  30

Glu Gly Leu Ser Tyr Asn Val Asp Ser Leu His Gln Lys His Gln Arg
            35                  40                  45

Ala Lys Arg Ala Val Ser His Glu Asp Gln Phe Leu Arg Leu Asp Phe
        50                  55                  60

His Ala His Gly Arg His Phe Asn Leu Arg Met Lys Arg Asp Thr Ser
65                  70                  75                  80

Leu Phe Ser Asp Glu Phe Lys Val Glu Thr Ser Asn Lys Val Leu Asp
                85                  90                  95

Tyr Asp Thr Ser His Ile Tyr Thr Gly His Ile Tyr Gly Glu Glu Gly
            100                 105                 110

Ser Phe Ser His Gly Ser Val Ile Asp Gly Arg Phe Glu Gly Phe Ile
        115                 120                 125

Gln Thr Arg Gly Gly Thr Phe Tyr Val Glu Pro Ala Glu Arg Tyr Ile
    130                 135                 140

Lys Asp Arg Thr Leu Pro Phe His Ser Val Ile Tyr His Glu Asp Asp
145                 150                 155                 160

Ile Asn Tyr Pro His Lys Tyr Gly Pro Gln Gly Gly Cys Ala Asp His
                165                 170                 175

Ser Val Phe Glu Arg Met Arg Lys Tyr Gln Met Thr Gly Val Glu Glu
            180                 185                 190

Val Thr Gln Ile Pro Gln Glu Glu His Ala Ala Asn Gly Pro Glu Leu
        195                 200                 205

Leu Arg Lys Lys Arg Thr Thr Ser Ala Glu Lys Asn Thr Cys Gln Leu
    210                 215                 220

Tyr Ile Gln Thr Asp His Leu Phe Phe Lys Tyr Tyr Gly Thr Arg Glu
225                 230                 235                 240

Ala Val Ile Ala Gln Ile Ser Ser His Val Lys Ala Ile Asp Thr Ile
                245                 250                 255

Tyr Gln Thr Thr Asp Phe Ser Gly Ile Arg Asn Ile Ser Phe Met Val
            260                 265                 270

Lys Arg Ile Arg Ile Asn Thr Thr Ala Asp Glu Lys Asp Pro Thr Asn
        275                 280                 285

Pro Phe Arg Phe Pro Asn Ile Gly Val Glu Lys Phe Leu Glu Leu Asn
    290                 295                 300

Ser Glu Gln Asn His Asp Asp Tyr Cys Leu Ala Tyr Val Phe Thr Asp
305                 310                 315                 320

Arg Asp Phe Asp Asp Gly Val Leu Gly Leu Ala Trp Val Gly Ala Pro
                325                 330                 335

Ser Gly Ser Ser Gly Gly Ile Cys Glu Lys Ser Lys Leu Tyr Ser Asp
            340                 345                 350

Gly Lys Lys Lys Ser Leu Asn Thr Gly Ile Ile Thr Val Gln Asn Tyr
        355                 360                 365

Gly Ser His Val Pro Pro Lys Val Ser His Ile Thr Phe Ala His Glu
    370                 375                 380

Val Gly His Asn Phe Gly Ser Pro His Asp Ser Gly Thr Glu Cys Thr
```

```
            385                 390                 395                 400

Pro Gly Glu Ser Lys Asn Leu Gly Gln Lys Glu Asn Gly Asn Tyr Ile
                405                 410                 415

Met Tyr Ala Arg Ala Thr Ser Gly Asp Lys Leu Asn Asn Lys Phe
            420                 425                 430

Ser Leu Cys Ser Ile Arg Asn Ile Ser Gln Val Leu Glu Lys Lys Arg
            435                 440                 445

Asn Asn Cys Phe Val Glu Ser Gly Gln Pro Ile Cys Gly Asn Gly Met
450                 455                 460

Val Glu Gln Gly Glu Glu Cys Asp Cys Gly Tyr Ser Asp Gln Cys Lys
465                 470                 475                 480

Asp Glu Cys Cys Phe Asp Ala Asn Gln Pro Glu Gly Arg Lys Cys Lys
                485                 490                 495

Leu Lys Pro Gly Lys Gln Cys Ser Pro Ser Gln Gly Pro Cys Cys Thr
            500                 505                 510

Ala Gln Cys Ala Phe Lys Ser Lys Ser Glu Lys Cys Arg Asp Asp Ser
            515                 520                 525

Asp Cys Ala Arg Glu Gly Ile Cys Asn Gly Phe Thr Ala Leu Cys Pro
530                 535                 540

Ala Ser Asp Pro Lys Pro Asn Phe Thr Asp Cys Asn Arg His Thr Gln
545                 550                 555                 560

Val Cys Ile Asn Gly Gln Cys Ala Gly Ser Ile Cys Glu Lys Tyr Gly
                565                 570                 575

Leu Glu Glu Cys Thr Cys Ala Ser Ser Asp Gly Lys Asp Asp Lys Glu
            580                 585                 590

Leu Cys His Val Cys Cys Met Lys Lys Met Asp Pro Ser Thr Cys Ala
            595                 600                 605

Ser Thr Gly Ser Val Gln Trp Ser Arg His Phe Ser Gly Arg Thr Ile
610                 615                 620

Thr Leu Gln Pro Gly Ser Pro Cys Asn Asp Phe Arg Gly Tyr Cys Asp
625                 630                 635                 640

Val Phe Met Arg Cys Arg Leu Val Asp Ala Asp Gly Pro Leu Ala Arg
                645                 650                 655

Leu Lys Lys Ala Ile Phe Ser Pro Glu Leu Tyr Glu Asn Ile Ala Glu
            660                 665                 670

Trp Ile Val Ala His Trp Trp Ala Val Leu Leu Met Gly Ile Ala Leu
            675                 680                 685

Ile Met Leu Met Ala Gly Phe Ile Lys Ile Cys Ser Val His Thr Pro
690                 695                 700

Ser Ser Asn Pro Lys Leu Pro Pro Pro Lys Pro Leu Pro Gly Thr Leu
705                 710                 715                 720

Lys Arg Arg Arg Pro Pro Gln Pro Ile Gln Gln Pro Gln Arg Gln Arg
                725                 730                 735

Pro Arg Glu Ser Tyr Gln Met Gly His Met Arg Arg
            740                 745

<210> SEQ ID NO 80
<211> LENGTH: 748
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 80

Met Val Leu Leu Arg Val Leu Ile Leu Leu Leu Ser Trp Ala Ala Gly
```

-continued

```
             1               5                  10                 15
           Met Gly Gly Gln Tyr Gly Asn Pro Leu Asn Lys Tyr Ile Arg His Tyr
                         20                 25                 30

Glu Gly Leu Ser Tyr Asn Val Asp Ser Leu His Gln Lys His Gln Arg
                         35                 40                 45

Ala Lys Arg Ala Val Ser His Glu Asp Gln Phe Leu Arg Leu Asp Phe
            50                 55                 60

His Ala His Gly Arg His Phe Asn Leu Arg Met Lys Arg Asp Thr Ser
            65                 70                 75                 80

Leu Phe Ser Asp Glu Phe Lys Val Glu Thr Ser Asn Lys Val Leu Asp
                             85                 90                 95

Tyr Asp Thr Ser His Ile Tyr Thr Gly His Ile Tyr Gly Glu Glu Gly
                        100                105                110

Ser Phe Ser His Gly Ser Val Ile Asp Gly Arg Phe Glu Gly Phe Ile
                        115                120                125

Gln Thr Arg Gly Gly Thr Phe Tyr Val Glu Pro Ala Glu Arg Tyr Ile
                        130                135                140

Lys Asp Arg Thr Leu Pro Phe His Ser Val Ile Tyr His Glu Asp Asp
           145                150                155                160

Ile Asn Tyr Pro His Lys Tyr Gly Pro Gln Gly Gly Cys Ala Asp His
                        165                170                175

Ser Val Phe Glu Arg Met Arg Lys Tyr Gln Met Thr Gly Val Glu Glu
                        180                185                190

Val Thr Gln Ile Pro Gln Glu Glu His Ala Ala Asn Gly Pro Glu Leu
                        195                200                205

Leu Arg Lys Lys Arg Thr Thr Ser Ala Glu Lys Asn Thr Cys Gln Leu
                        210                215                220

Tyr Ile Gln Thr Asp His Leu Phe Phe Lys Tyr Tyr Gly Thr Arg Glu
           225                230                235                240

Ala Val Ile Ala Gln Ile Ser Ser His Val Lys Ala Ile Asp Thr Ile
                        245                250                255

Tyr Gln Thr Thr Asp Phe Ser Gly Ile Arg Asn Ile Ser Phe Met Val
                        260                265                270

Lys Arg Ile Arg Ile Asn Thr Thr Ala Asp Glu Lys Asp Pro Thr Asn
                        275                280                285

Pro Phe Arg Phe Pro Asn Ile Gly Val Glu Lys Phe Leu Glu Leu Asn
                        290                295                300

Ser Glu Gln Asn His Asp Asp Tyr Cys Leu Ala Tyr Val Phe Thr Asp
           305                310                315                320

Arg Asp Phe Asp Asp Gly Val Leu Gly Leu Ala Trp Val Gly Ala Pro
                        325                330                335

Ser Gly Ser Ser Gly Gly Ile Cys Glu Lys Ser Lys Leu Tyr Ser Asp
                        340                345                350

Gly Lys Lys Lys Ser Leu Asn Thr Gly Ile Ile Thr Val Gln Asn Tyr
                        355                360                365

Gly Ser His Val Pro Pro Lys Val Ser His Ile Thr Phe Ala His Glu
                        370                375                380

Val Gly His Asn Phe Gly Ser Pro His Asp Ser Gly Thr Glu Cys Thr
           385                390                395                400

Pro Gly Glu Ser Lys Asn Leu Gly Gln Lys Glu Asn Gly Asn Tyr Ile
                        405                410                415

Met Tyr Ala Arg Ala Thr Ser Gly Asp Lys Leu Asn Asn Asn Lys Phe
                        420                425                430
```

```
Ser Leu Cys Ser Ile Arg Asn Ile Ser Gln Val Leu Glu Lys Lys Arg
        435                 440                 445

Asn Asn Cys Phe Val Glu Ser Gly Gln Pro Ile Cys Gly Asn Gly Met
    450                 455                 460

Val Glu Gln Gly Glu Glu Cys Asp Cys Gly Tyr Ser Asp Gln Cys Lys
465                 470                 475                 480

Asp Glu Cys Cys Phe Asp Ala Asn Gln Pro Glu Gly Arg Lys Cys Lys
            485                 490                 495

Leu Lys Pro Gly Lys Gln Cys Ser Pro Ser Gln Gly Pro Cys Cys Thr
            500                 505                 510

Ala Gln Cys Ala Phe Lys Ser Lys Ser Glu Lys Cys Arg Asp Asp Ser
        515                 520                 525

Asp Cys Ala Arg Glu Gly Ile Cys Asn Gly Phe Thr Ala Leu Cys Pro
        530                 535                 540

Ala Ser Asp Pro Lys Pro Asn Phe Thr Asp Cys Asn Arg His Thr Gln
545                 550                 555                 560

Val Cys Ile Asn Gly Gln Cys Ala Gly Ser Ile Cys Glu Lys Tyr Gly
            565                 570                 575

Leu Glu Glu Cys Thr Cys Ala Ser Ser Asp Gly Lys Asp Asp Lys Glu
            580                 585                 590

Leu Cys His Val Cys Cys Met Lys Lys Met Asp Pro Ser Thr Cys Ala
        595                 600                 605

Ser Thr Gly Ser Val Gln Trp Ser Arg His Phe Ser Gly Arg Thr Ile
    610                 615                 620

Thr Leu Gln Pro Gly Ser Pro Cys Asn Asp Phe Arg Gly Tyr Cys Asp
625                 630                 635                 640

Val Phe Met Arg Cys Arg Leu Val Asp Ala Asp Gly Pro Leu Ala Arg
            645                 650                 655

Leu Lys Lys Ala Ile Phe Ser Pro Glu Leu Tyr Glu Asn Ile Ala Glu
            660                 665                 670

Trp Ile Val Ala His Trp Trp Ala Val Leu Leu Met Gly Ile Ala Leu
        675                 680                 685

Ile Met Leu Met Ala Gly Phe Ile Lys Ile Cys Ser Val His Thr Pro
        690                 695                 700

Ser Ser Asn Pro Lys Leu Pro Pro Pro Lys Pro Leu Pro Gly Thr Leu
705                 710                 715                 720

Lys Arg Arg Arg Pro Pro Gln Pro Ile Gln Gln Pro Gln Arg Gln Arg
            725                 730                 735

Pro Arg Glu Ser Tyr Gln Met Gly His Met Arg Arg
            740                 745
```